(12) United States Patent
Bougneres et al.

(10) Patent No.: US 12,195,767 B2
(45) Date of Patent: Jan. 14, 2025

(54) ADENO-ASSOCIATED VIRUS GENE THERAPY FOR 21-HYDROXYLASE DEFICIENCY

(71) Applicant: Adrenas Therapeutics, Inc., Palo Alto, CA (US)

(72) Inventors: Pierre Bougneres, Chaville (FR); Guangping Gao, Westborough, MA (US)

(73) Assignee: Adrenas Therapeutics, Inc., Palo Alto, CA (US)

(*) Notice: Subject to any disclaimer, the term of this patent is extended or adjusted under 35 U.S.C. 154(b) by 1034 days.

(21) Appl. No.: 16/962,552

(22) PCT Filed: Jan. 17, 2019

(86) PCT No.: PCT/US2019/013991
§ 371 (c)(1),
(2) Date: Jul. 16, 2020

(87) PCT Pub. No.: WO2019/143803
PCT Pub. Date: Jul. 25, 2019

(65) Prior Publication Data
US 2021/0277365 A1   Sep. 9, 2021

Related U.S. Application Data

(60) Provisional application No. 62/640,311, filed on Mar. 8, 2018, provisional application No. 62/618,307, filed on Jan. 17, 2018.

(51) Int. Cl.
| | |
|---|---|
| *C07H 21/02* | (2006.01) |
| *A61K 48/00* | (2006.01) |
| *C12N 7/00* | (2006.01) |
| *C12N 9/02* | (2006.01) |
| *C12N 15/86* | (2006.01) |

(52) U.S. Cl.
CPC .......... *C12N 9/0071* (2013.01); *A61K 48/005* (2013.01); *C12N 7/00* (2013.01); *C12N 15/86* (2013.01); *C12N 2750/14143* (2013.01); *C12Y 114/14* (2013.01)

(58) Field of Classification Search
CPC .................................................. C12N 15/86
See application file for complete search history.

(56) References Cited

U.S. PATENT DOCUMENTS

| | | | |
|---|---|---|---|
| 5,478,745 A | 12/1995 | Samulski et al. | |
| 6,136,597 A | 10/2000 | Hope et al. | |
| 6,287,814 B1 | 9/2001 | Hope et al. | |
| 7,198,951 B2 | 4/2007 | Gao et al. | |
| 7,282,199 B2 | 10/2007 | Gao et al. | |
| 7,906,111 B2 | 3/2011 | Wilson et al. | |
| 8,865,881 B2 * | 10/2014 | Balazs | A61P 31/12 435/320.1 |
| 9,587,250 B2 | 3/2017 | Gao et al. | |
| 9,677,089 B2 | 6/2017 | Gao et al. | |
| 9,840,719 B2 | 12/2017 | High et al. | |
| 10,385,376 B2 | 8/2019 | Lattemann et al. | |
| 11,078,247 B2 * | 8/2021 | Fotin-Mleczek | C07K 14/505 |

FOREIGN PATENT DOCUMENTS

| | | | |
|---|---|---|---|
| JP | 2002516092 A | 6/2002 | |
| WO | WO-9961601 A2 | 12/1999 | |
| WO | WO 2012/115980 A1 | 8/2012 | |
| WO | WO-2015041718 A1 | 3/2015 | |
| WO | WO 2017/008154 A1 * | 1/2017 | ............. C12N 15/86 |
| WO | WO-2022198038 A1 | 9/2022 | |

OTHER PUBLICATIONS

Fischer et al. (Molecular Therapy, 25, 8, 1954-1865, 2017).*
Zhang et al. (Cancer-Targeted Gene and Cell Therapy, 24, Supp 1, S84-S85, 2016).*
Perdomini et al. (Gene Therapy, 2017, 24, 275-281).*
Eclov, et al., Durable CYP21A2 Gene Therapy in Non-Human Primates for Treatment of Congenital Adrenal Hyperplasia, 2019 European Society of Gene & Cell Therapy, Poster, Jan. 1, 2019, 1 page, XP055934324. Retrieved from the Internet: URL: https://adrenastx.com/wp-content/uploads/BBIO-CAH-GTx-BBP-631-ESGCT-NHP.pdf [retrieved on Jun. 22, 2022].
Eclov, RJ, et al., Durable CYP21A2 Gene Therapy in Non-Human Primates for Treatment of Congenital Adrenal Hyperplasia, Poster, 1 page.
Majowicz et al., Successful Repeated Hepatic Gene Delivery in Mice and Non-human Primates Achieved by Sequential Administration of AAV5$^{ch}$ and AAV1, American Society of Gene & Cell Therapy, Molecular Therapy, Aug. 2017, pp. 1831-1842, vol. 25, No. 8.
Paneda et al., Safety and Liver Transduction Efficacy of rAAV5-cohPBGD in Nonhuman Primates: A Potential Therapy for Acute Intermittent Porphyria, Human Gene Therapy, Dec. 2013, pp. 1007-1017, vol. 24.
International Search Report and Written Opinion issued by the International Searching Authority for Application No. PCT/US2019/013991, dated Mar. 27, 2019, 9 pages.
Beltran et al., "rAAV2/5 gene-targeting to rods: dose-dependent efficiency and complications associated with different promoters," Gene Therapy, 17(9): 1162-1174 (2010).
Boshart et al., "A very strong enhancer is located upstream of an immediate early gene of human cytomegalovirus," Cell, 41:521-530 (1985).
Bruining et al., "Clinical Case Seminar Fertility and Body Composition after Laparoscopic Bilateral Adrenalectomy in a 30-Year-Old Female with Congenital Adrenal Hyperplasia," J Clin Endocrinol Metab 86(2):482-484 (2001).
El-Maouche et al., "Congenital adrenal hyperplasia", Lancet 390(10108):2194-2210 (2017).

(Continued)

*Primary Examiner* — Amy Rose Hudson
(74) *Attorney, Agent, or Firm* — COOLEY LLP

(57) ABSTRACT

Disclosed herein are recombinant adeno-associated viral vectors expressing 21-hydroxylase (21OH) protein and related uses for treating 21OH deficiency.

20 Claims, 79 Drawing Sheets

Specification includes a Sequence Listing.

(56) References Cited

OTHER PUBLICATIONS

Gastaud et al., "Impaired Sexual and Reproductive Outcomes in Women with Classical Forms of Congenital Adrenal Hyperplasia," J Clin Endocrinol Metab, 92(4), 1391-1396 (2007).

Gmyrek et al., "Bilateral Laparoscopic Adrenalectomy as a Treatment for Classic Congenital Adrenal Hyperplasia Attributable to 21-Hydroxylase Deficiency," Pediatrics, 109: E28 (2002), 6 pages.

Gray et al., "Optimizing Promoters for Recombinant Adeno-Associated Virus-Mediated Gene Expression in the Peripheral and Central Nervous System Using Self-Complementary Vectors," Hum Gene Ther, 22(9): 1143-1153 (2011).

Hahner et al., "High Incidence of Adrenal Crisis in Educated Patients with Chronic Adrenal Insufficiency: A Prospective Study," J Clin Endocrinol Metab, 100(2): 407-416 (2015).

Kurtoglu et al., "Non-Classical Congenital Adrenal Hyperplasia in Childhood," J Clin Res Pediatr Endocrinol, 9(1): 1-7 (2017).

Macapagal et al., "Gene Therapy of 21-Hydroxylase Deficient Mice Utilizing an Adeno-Associated Virus Vector," The Endocrine Society, Program & Abstracts, 84trh Annual Meeting, Jun. 19-22, 2002, Abstract P1-503, 4 pages.

Markmann et al., "Biology of the Adrenal Gland Cortex Obviates Effective Use of Adeno-Associated Virus Vectors to Treat Hereditary Adrenal Disorders," Human Gene Therapy 29(4):403-412 (2018).

Mussolino et al., "AAV-mediated photoreceptor transduction of the pig cone-enriched retina," Gene Therapy, 18(7): 637-645 (2011).

Naiki et al., "Extra-adrenal induction of Cyp21a1 ameliorates systemic steroid metabolism in a mouse model of congenital adrenal hyperplasia," Endocrine Journal 63(10):897-904 (2016).

Perdomini et al., "An AAVrh10-CAG-CYP21-HA vector allows persistent correction of 21-hydroxylase deficiency in a Cyp21-/- mouse model," Gene Therapy, 24(5):275-281 (2017).

Rabinowitz et al., "Cross-packaging of a single adeno-associated virus (AAV) type 2 vector genome into multiple AAV serotypes enables transduction with broad specificity," J Viral, 76(2):791-801 (2002).

Tajima et al., "Prenatal Dexamethasone Treatment Does Not Prevent Alterations of the Hypothalamic Pituitary Adrenal Axis in Steroid 21-Hydroxylase Deficient Mice," Endocrinology 140:3354-3362 (1999).

Tajima et al., "Restoration of adrenal steroidogenesis by adenovirus-mediated transfer of human cytochrome P450 21-hydroxylase into the adrenal gland of 21-hydroxylase-deficient mice," Gene Therapy 6:1898-1903 (1999).

Thakral and Ghoshal, "miR-122 is a Unique Molecule with Great Potential in Diagnosis, Prognosis of Liver Disease, and Therapy Both as miRNA Mimic and Antimir," Curr Gene Ther. 15(2): 142-150 (2015).

Yanase et al., "Differentiation and regeneration of adrenal tissues: An initial step toward regeneration therapy for steroid insufficiency," Endocrine Journal, Tokyo, JP 53(4):449-459 (2006).

Wang et al., "Sustained correction of bleeding disorder in hemophilia B mice by gene therapy," Proc. Natl. Acad Sci., USA, 96(7): 3906-3910 (1999).

Office Action and Search Report for Chinese Application No. CN20198008414 dated Jan. 18, 2023, 19 pages.

Office Action for Japanese Application No. JP20200537156 dated Jan. 6, 2023, 6 pages.

Office Action for Japanese Application No. JP20200537156 dated Jun. 21, 2023, 10 pages.

Vermeulen, et al., *Homo sapiens* cytochrome P450 family 21 subfamily A member 2 (CYP21A2), transcript 1, mRNA, Accession No. NM_000500.7, Genebank, 2017, 4 pages.

Mattar, et al., Stable human FIX expression after 0.9 G intrauterine gene transfer of self-complementary adeno-associated viral vector 5 and 8 in macaques, Molecular Therapy, Nov. 2011, pp. 1950-1960.

McLaughlin, et al., Adeno-associated virus general transduction vectors: analysis of proviral structures, Journal of virology, Jun. 1988, pp. 1963-1973.

Office Action for Japanese Application No. JP20200537156 mailed Jan. 19, 2024, 8 pages.

Tran, et al., Adrenal gland infection by serotype 5 adenovirus requires coagulation factors, PLoS One, Apr. 2013, 9 pages.

\* cited by examiner

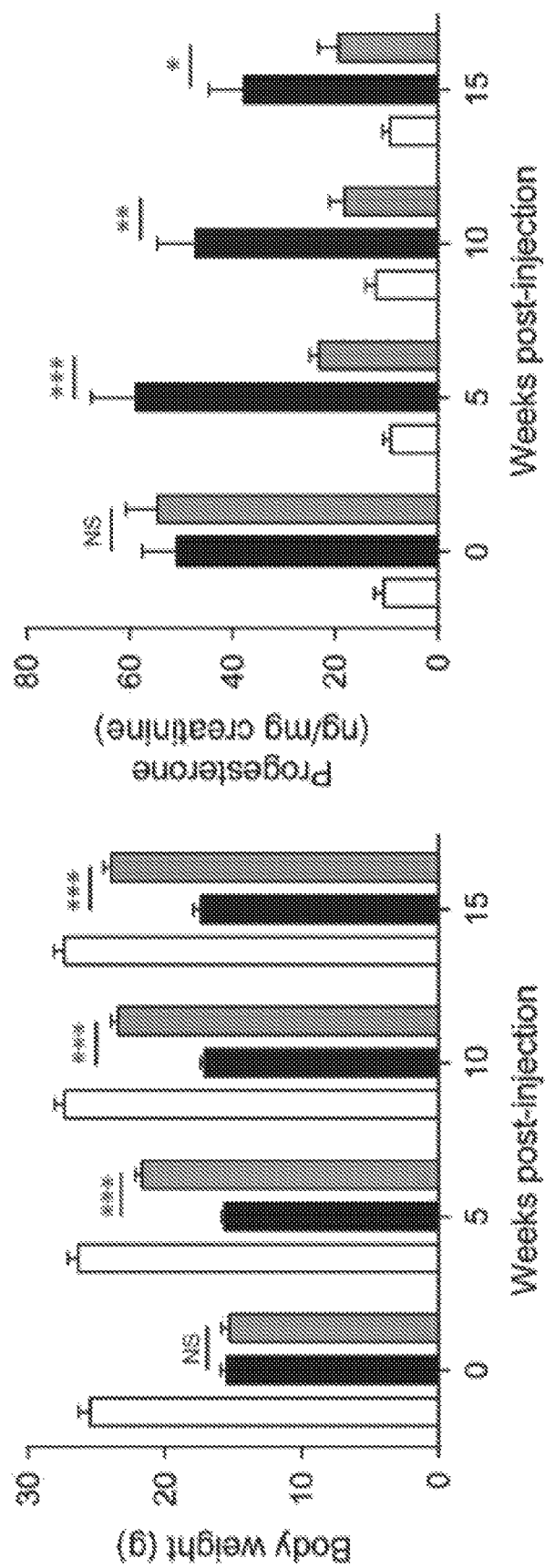

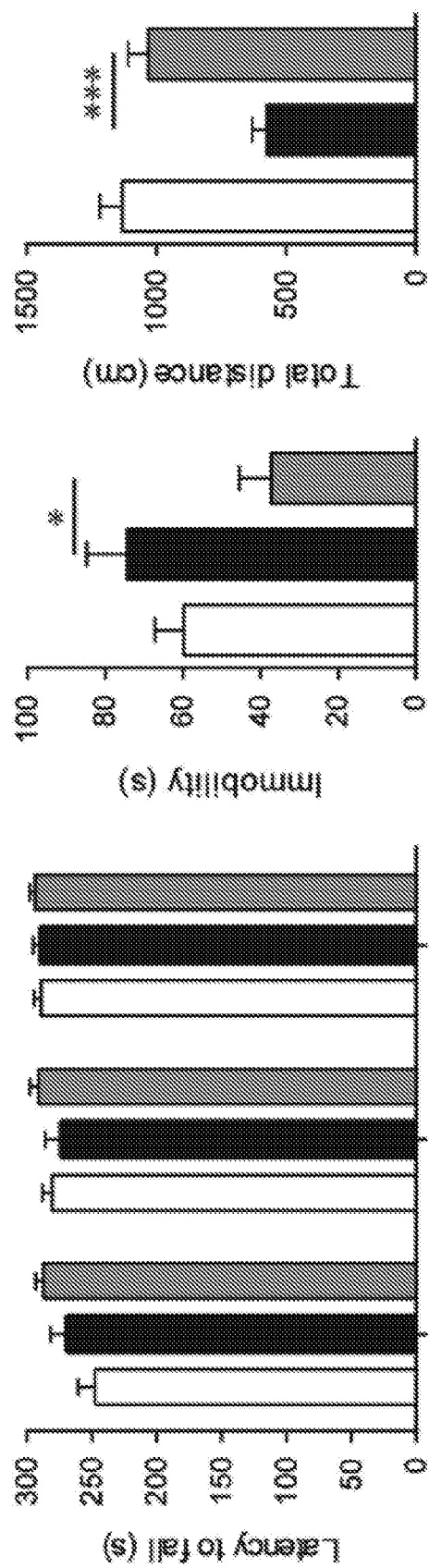

FIG. 18

| Intravenous | vg per kg: | $2.10^{13}$ | $5.10^{13}$ | $2.10^{14}$ |
|---|---|---|---|---|
| VGC | Mean: | 0.2 | 3.2 | 16.6 |
| | Range: | 0.1-0.3 | 2-4.4 | 15.3-17.8 |
| | Slices ≥ 0.2 vgc * | 62% | 100% | 100% |
| | Slices ≥ 1 vgc | 0% | 100% | 100% |

IF

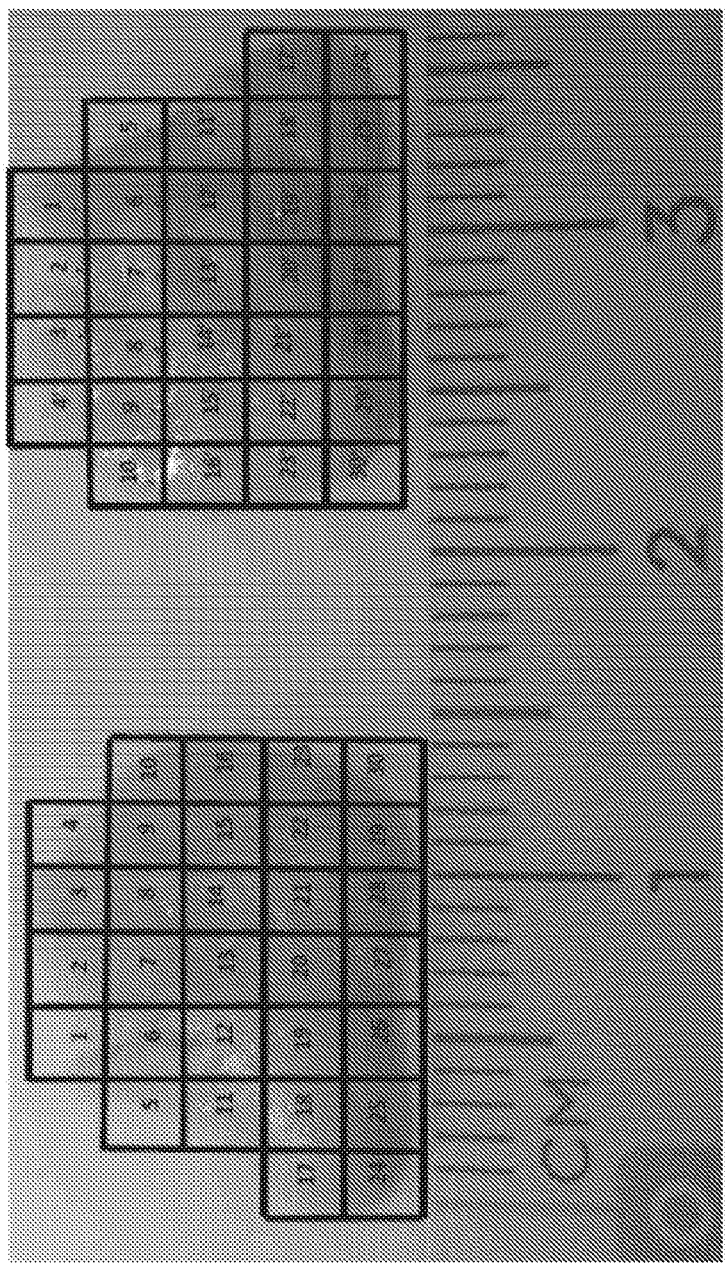
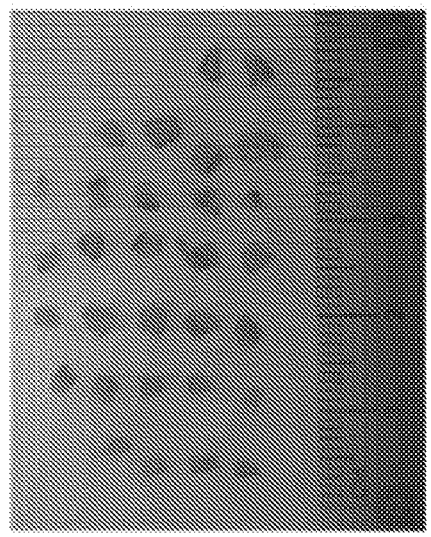
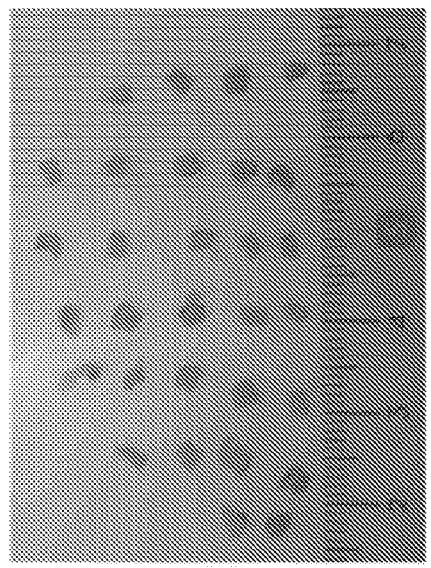
FIG. 27

FIG. 28

Liver NHP02 & NHP04

VGC Mean: 10.3/10 (ES) and 0.8/3.5 (Eu)

5.10$^{13}$ vg per kg intravenous
Mean 62.4
Range 47-111
VGC GFP:

VGC Mean : 0.02 (ES) and 0.9 (Eu)

$1.5 \cdot 10^{11}$ (= $5 \cdot 10^{13}$ per kg) Intravenous

VGC GFP

Mean: 81

Range: 62-114

VGC  Mean : 1.5 (ES) and 2.9 (Eu)

VGC CYP21 :  Mean  220
Range : 191-293

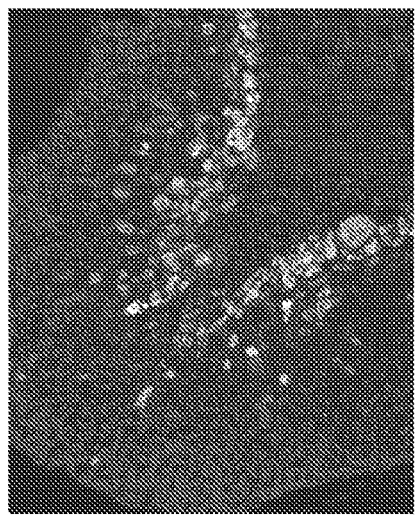
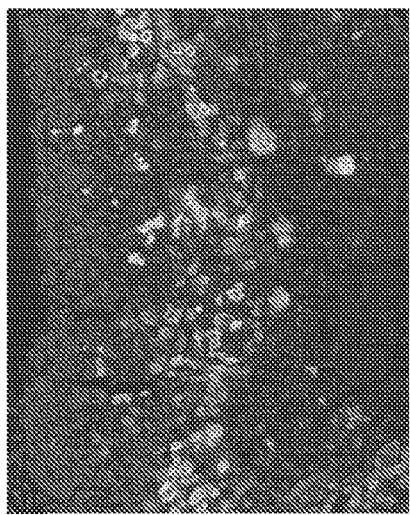
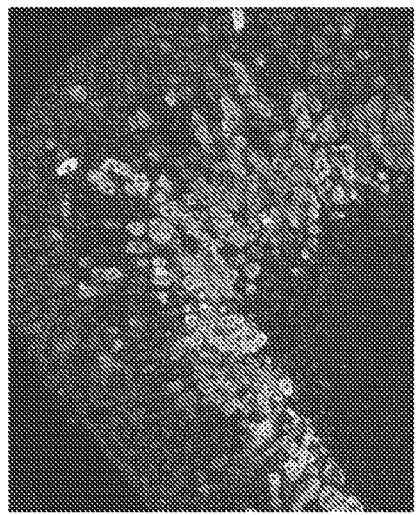
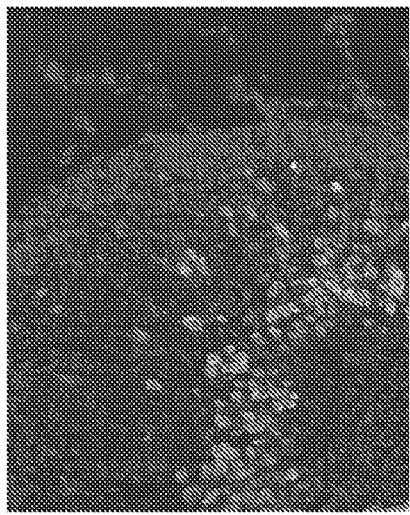
FIG. 43

Treated males

247

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 359 | 27 | 191 | 391 | 108 | 487 | 219 | 209 | 228 | 130 | 118 | 284 | 136 | 106 | 114 |

248

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 88 | 208 | 656 | 538 | 658 | 634 | 247 | 199 | 193 | 142 | 100 | 181 | 170 | 151 | 179 |

841

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 1040 | 279 | 363 | 281 | 79 | 124 | 90 | 70 | 147 | 309 | 262 | 210 | 166 | 197 | 162 |

869

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 1381 | 1171 | 762 | 237 | 125 | 398 | 250 | 264 | 152 | x | 151 | 103 | 76 | 50 | x |

Treated females

319

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 793 | 557 | 544 | 290 | 188 | 196 | 128 | 473 | 1096 | 1070 | 385 | 271 | 316 | 289 | 307 |

836

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 933 | 146 | 297 | 196 | 186 | 217 | 166 | 269 | 294 | 164 | 255 | 249 | 218 | 252 | 218 |

873

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 924 | 225 | 231 | 342 | 214 | 310 | 525 | 183 | 226 | 139 | 166 | 156 | 118 | 105 | 169 |

FIG. 46A

Untreated male

326

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 587 | 443 | 1073 | 462 | 440 | 724 | 820 | 503 | 537 | 750 | 807 | 1009 | 1255 | 1435 | x |

Untreated females

340

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 234 | 2515 | 1001 | 515 | 364 | 695 | 417 | 1058 | 546 | 914 | 566 | 938 | 883 | 1099 | 690 |

855

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 1680 | 701 | 1052 | 892 | 439 | 902 | 747 | 674 | 1373 | 975 | 947 | 756 | 474 | 267 | 565 |

870

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 444 | 413 | 635 | 1149 | 555 | 895 | 970 | 634 | x | 627 | 902 | 1297 | 797 | 807 | 521 |

FIG. 46B

Wt males (sham injected)

810

| w0 | w2 | w3 | w4 | w5 | w6 | w7 | w8 | w9 | w10 | w11 | w12 | w13 | w14 | w15 |
|---|---|---|---|---|---|---|---|---|---|---|---|---|---|---|
| 71 | 51 | 41 | 62 | 57 | 90 | 126 | 71 | 118 | 60 | 143 | 97 | 111 | 90 | 123 |

246

| w0 | w2 | w3 | w4 | w5 | w6 | w7 | w8 | w9 | w10 | w11 | w12 | w13 | w14 | w15 |
|---|---|---|---|---|---|---|---|---|---|---|---|---|---|---|
| 25 | 49 | 71 | 65 | 20 | 170 | 63 | 74 | 30 | 27 | 84 | 141 | 34 | 149 | 95 |

Wt females (sham injected)

824

| w0 | w2 | w3 | w4 | w5 | w6 | w7 | w8 | w9 | w10 | w11 | w12 | w13 | w14 | w15 |
|---|---|---|---|---|---|---|---|---|---|---|---|---|---|---|
| 127 | 143 | 313 | 157 | 112 | 201 | 411 | 327 | 159 | 216 | 122 | 162 | 284 | 275 | 227 |

4764

| w0 | w2 | w3 | w4 | w5 | w6 | w7 | w8 | w9 | w10 | w11 | w12 | w13 | w14 | w15 |
|---|---|---|---|---|---|---|---|---|---|---|---|---|---|---|
| 265 | 103 | 135 | 166 | 259 | 183 | 361 | 355 | 149 | 147 | 271 | 199 | 110 | 98 | 165 |

FIG. 46C

Treated males

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 321 | 139 | 200 | 261 | 193 | 180 | 106 | 103 | 163 | 143 | 160 | 162 | 155 | 201 | 135 |

379

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 477 | 1318 | 320 | 475 | 257 | 192 | 209 | 274 | 121 | 73 | 88 | 61 | 71 | 61 | 67 |

486

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 575 | 178 | 532 | 408 | 107 | 311 | 112 | 158 | 94 | 56 | 118 | 37 | 27 | 54 | 40 |

545

Treated females

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 455 | 634 | 384 | 183 | 253 | 527 | 243 | 454 | 218 | 210 | 445 | 138 | 267 | 373 | 580 |

394

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 425 | 743 | 323 | 261 | 213 | 551 | 323 | 341 | 451 | 484 | 342 | 147 | 594 | 200 | 261 |

409

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 417 | 524 | 505 | 241 | 172 | 142 | 213 | 225 | 280 | 238 | 295 | 274 | 224 | 215 | 221 |

420

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 358 | 671 | 923 | 258 | 225 | 215 | 315 | 269 | 246 | 239 | 129 | 111 | 153 | 139 | 196 |

431

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 376 | 520 | 794 | 261 | 247 | 189 | 341 | 263 | 339 | 335 | 589 | 243 | 521 | 284 | 282 |

Untreated males

514:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 801 | 1356 | 511 | 711 | 1068 | 2198 | 1937 | 728 | 759 | 606 | 489 | 314 | 303 | 216 | 328 |

525:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 631 | 1142 | 756 | 596 | 841 | 731 | 1197 | 2413 | 677 | 491 | 433 | 337 | 344 | 351 | 417 |

544:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 486 | 840 | 1536 | 1490 | 630 | 889 | 1099 | 831 | 646 | 673 | 322 | 232 | 247 | 636 | 124 |

Untreated females

410:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 396 | 308 | 1015 | 487 | 644 | 606 | 664 | 659 | 549 | 438 | 997 | 434 | 561 | 1040 | 424 |

421:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 782 | 379 | 819 | 586 | 412 | 349 | 929 | 463 | 873 | 477 | 1069 | 532 | 644 | 273 | 628 |

436:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 360 | 310 | 498 | 477 | 371 | 307 | 647 | 1250 | 617 | 705 | 582 | 289 | 432 | 493 | 282 |

457:

| W0 | W2 | W3 | W4 | W5 | W6 | W7 | W8 | W9 | W10 | W11 | W12 | W13 | W14 | W15 |
|---|---|---|---|---|---|---|---|---|---|---|---|---|---|---|
| 510 | 476 | 672 | 686 | 582 | 588 | 433 | 813 | 501 | 177 | 461 | 371 | 229 | 426 | 630 |

FIG. 49B

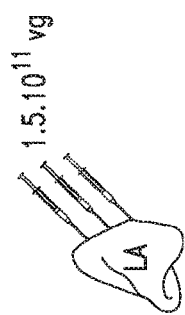
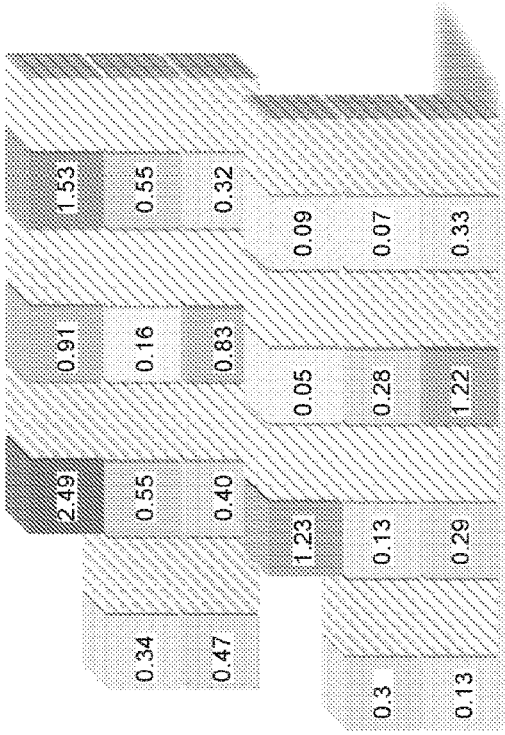
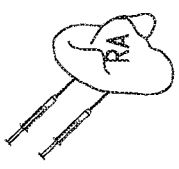
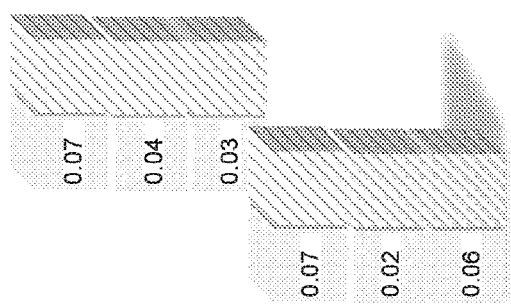
FIG. 52A

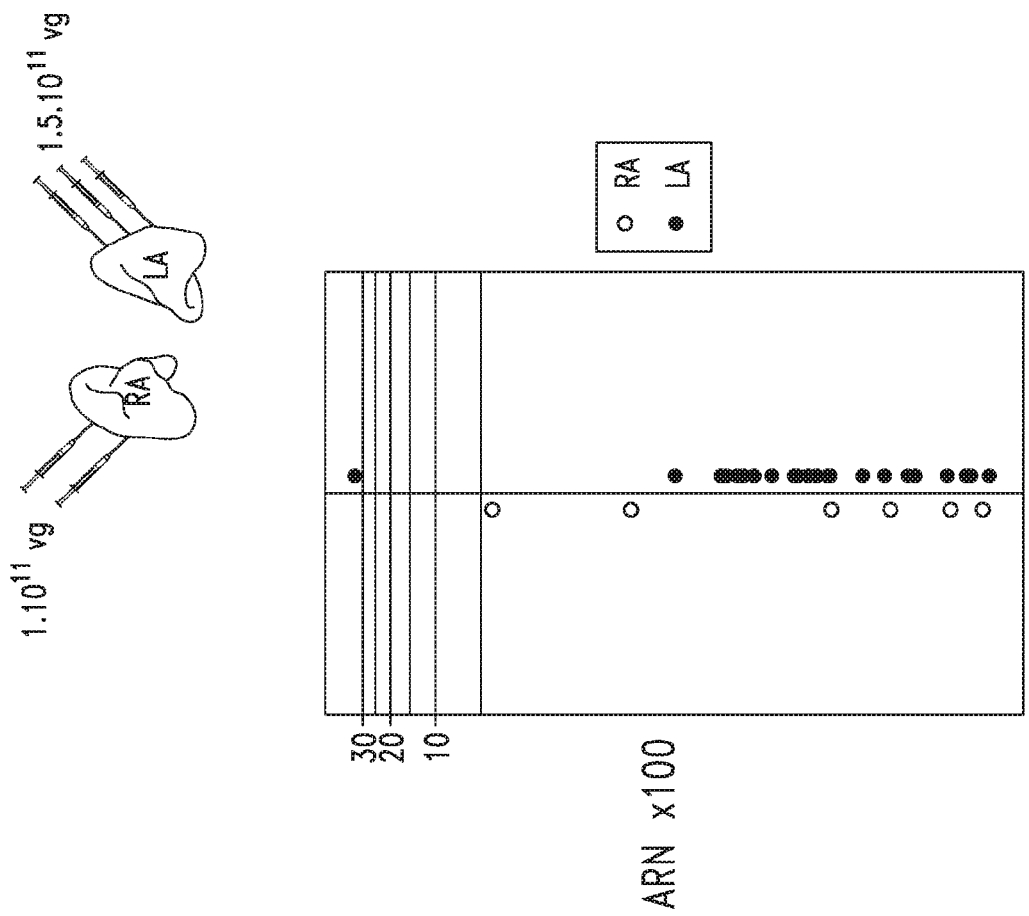
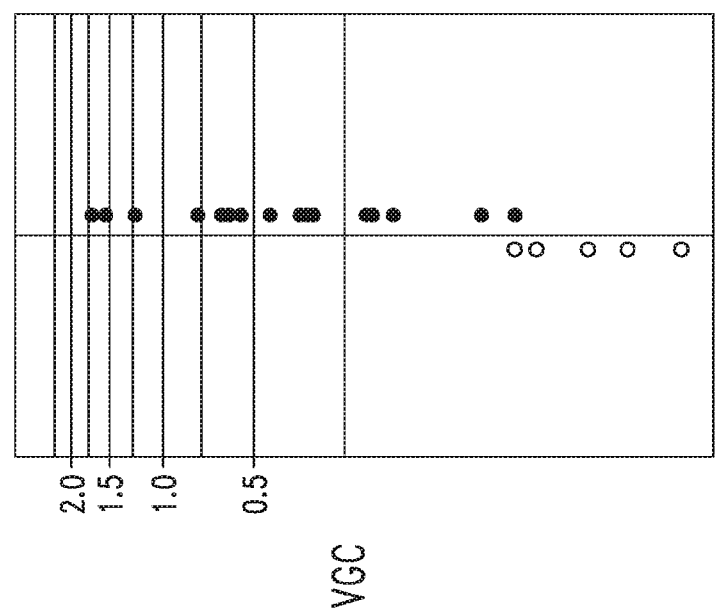
FIG. 52B

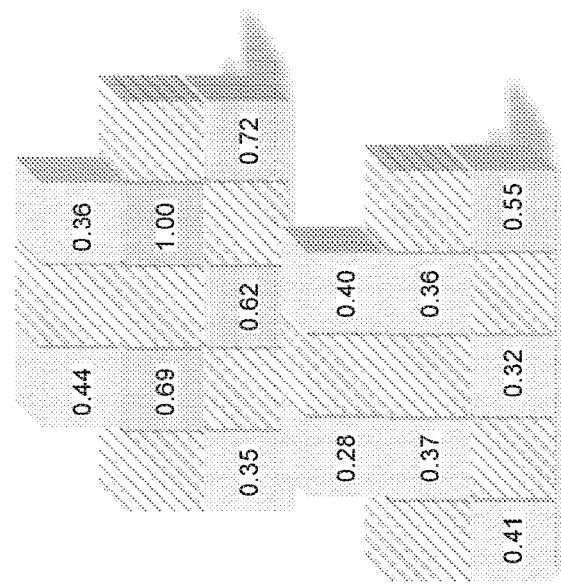
$5 \cdot 10^{11}$ vg/kg = $1.2 \cdot 10^{12}$ vg
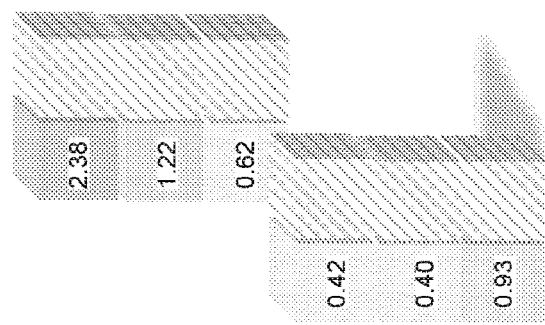
Mean VGC/cell = 0.99 (0.4-2.38)
6 pieces
Mean VGC/cell = 0.49 (0.28-1)
14 pieces
FIG. 53A

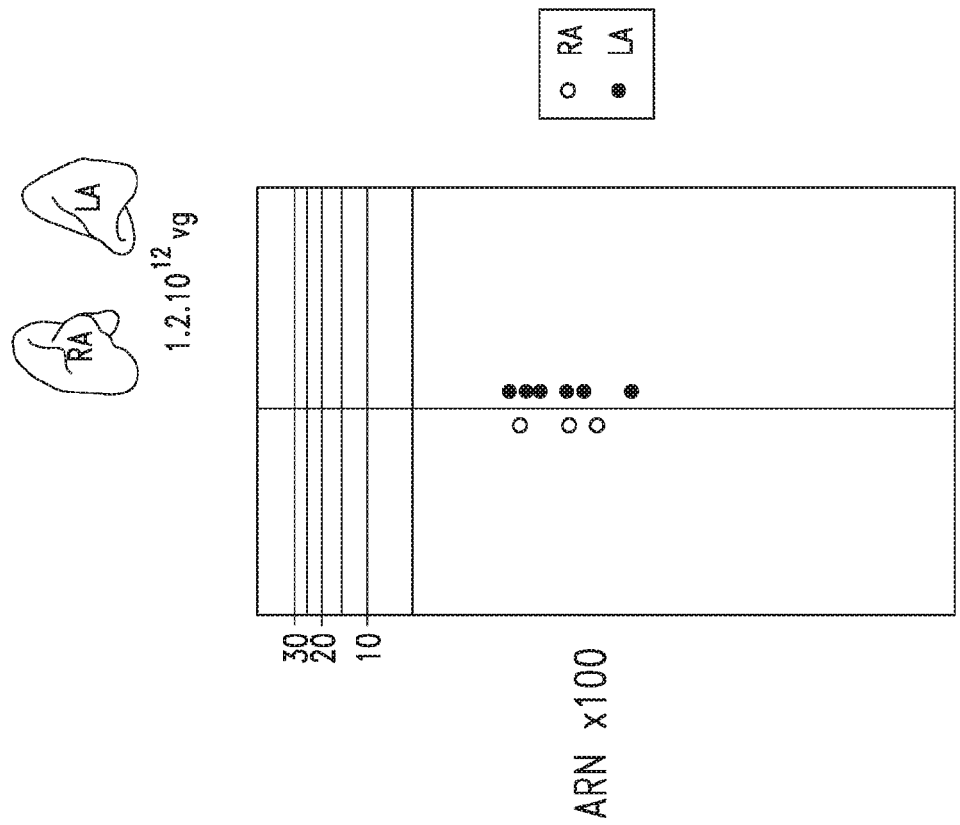
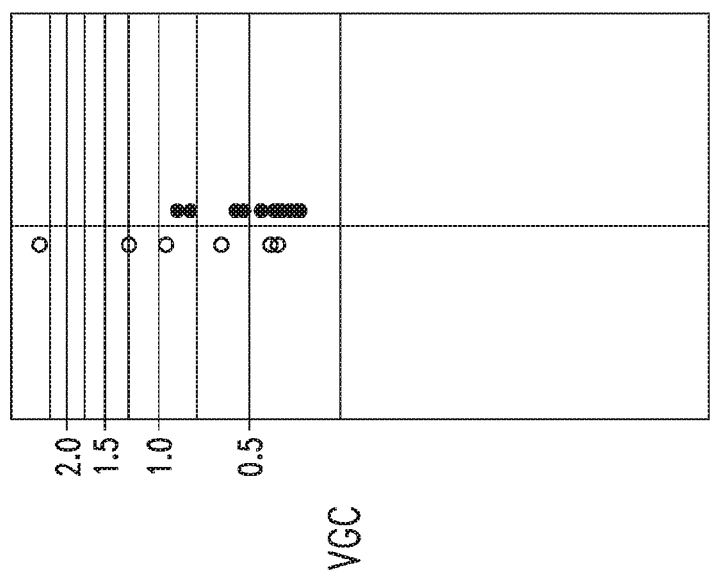
FIG. 53B

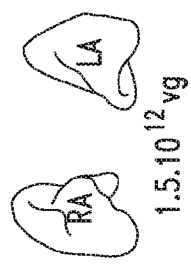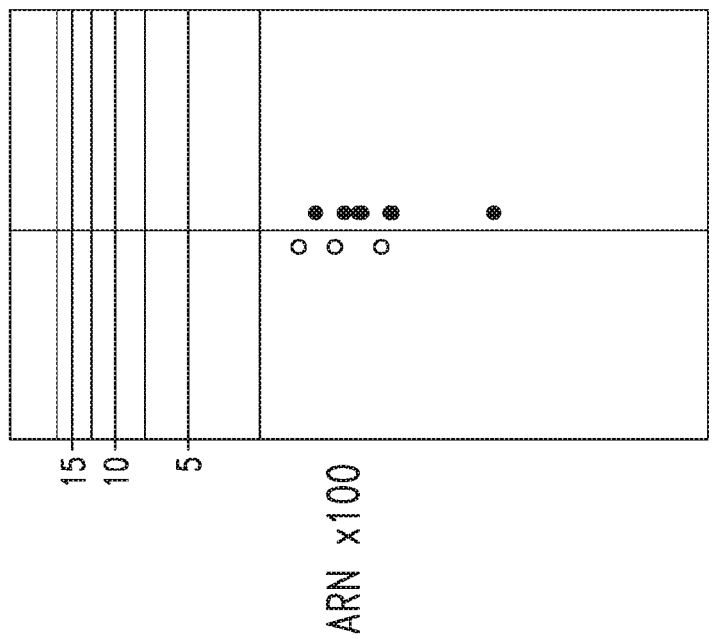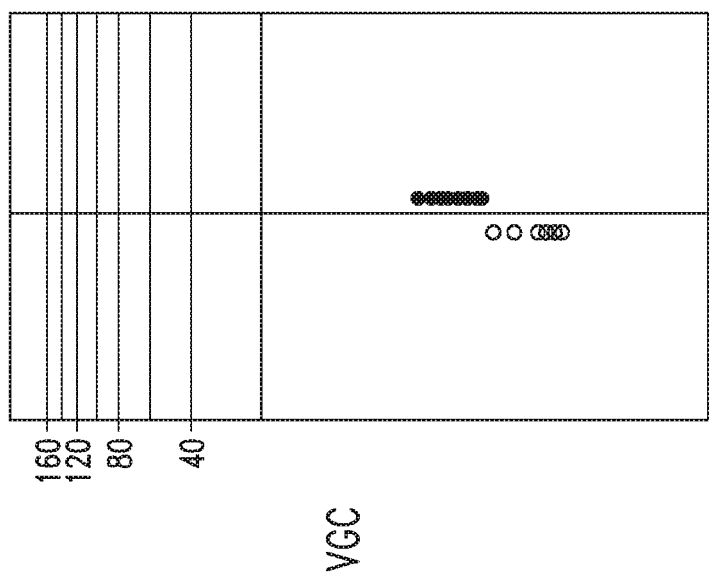
FIG. 55B

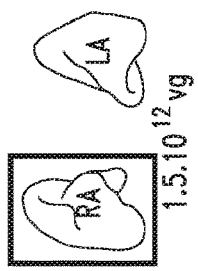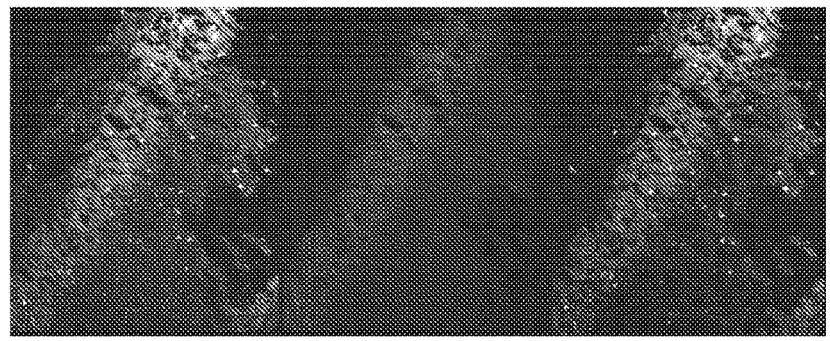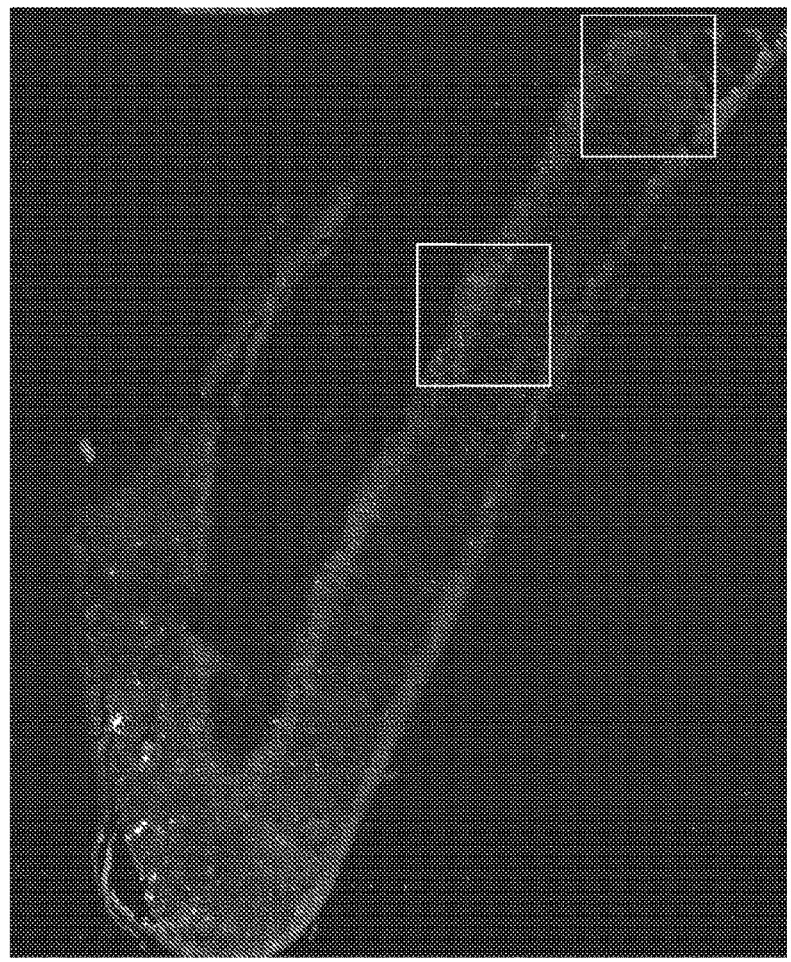
FIG. 55C

| | ROA | Vector dose per kg | VGC |
|---|---|---|---|
| AAV1–PGK–CYP21HA | | | |
| Inj RA | IA | $1.7 \cdot 10^{11}$ | 1 (0.14–6.5) |
| AAV5–PGK–CYP21HA | | | |
| Inj RA | IA | $0.68 \cdot 10^{11}$ | 1.9 (0.08–5.6) |
| Inj RA | IA | $4.7 \cdot 10^{11}$ | 82 (0.3–795) |
| Inj RA | IA | $3.3 \cdot 10^{11}$ | 60 (1.6–584) |
| AAV6–CAG–GFP | | | |
| Inj RA | LA | $1 \cdot 10^{11}$ | 0.065 (0–0.22) |
| Inj RA | LA | $0.83 \cdot 10^{11}$ | 0.84 (0.03–8.6) |
| AAV1–CB6–GFP | | | |
| Inj RA | LA | $0.9 \cdot 10^{11}$ | 0.56 (0.14–2.6) |
| AAV5–PGK–GFP | | | |
| Inj RA | LA | $4.6 \cdot 10^{11}$ | 1.2 (0.15–5.5) |

| AAV5-WT-miR | AAV5-CO-miR | AAV5-cyno |
|---|---|---|

| NHP11 | F28 mo, 2.15 kg, AAV5-CBA-Kozak-hCYP21-miR122 3.10¹² vg/kg IV (10 min) |
| NHP12 | F28 mo, 2 kg, AAV5-CBA-Kozak-hCYP21-miR122 3.10¹² vg/kg IV (10 min) |
| NHP13 | F28 mo, 2.15 kg, AAV5-CBA-Kozak-hCYP21-miR122 3.10¹² vg/kg IV (10 min) |
| NHP14 | F28 mo, 2.3 kg, AAV5-CBA-Kozak-hCYP21-miR122 3.10¹² vg/kg IV (10 min) |

| NHP15 | F32 mo, 2.45 kg, AAV5-CBA-Kozak-COhCYP21-miR122 3.10¹² vg/kg IV (10 min) |
| NHP16 | F32 mo, 2.75 kg, AAV5-CBA-Kozak-COhCYP21-miR122 3.10¹² vg/kg IV (10 min) |
| NHP17 | F28 mo, 2.65 kg, AAV5-CBA-Kozak-COhCYP21-miR122 3.10¹² vg/kg IV (10 min) |
| NHP18 | F29 mo, 2.55 kg, AAV5-CBA-Kozak-COhCYP21-miR122 3.10¹² vg/kg IV (10 min) |

| NHP19 | F32 mo, 3.35 kg, AAV5-CBA-Kozak-cynoCYP21 3.10¹² vg/kg IV (10 min) |
| NHP20 | F32 mo, 3.15 kg, AAV5-CBA-Kozak-cynoCYP21 3.10¹² vg/kg IV (10 min) |

| | AAV5-WT-miR | AAV5-CO-miR | AAV5-cyno |
|---|---|---|---|
| CYP21 VGC | 3.8 (0.1–24.3) | 2.2 (0.5–9.5) | 4.1 (1.2–9.5) |
| h mRNA/GADPH mRNA | $2.3 \cdot 10^{-2}$ ($1.7 \cdot 10^{-3} - 1.0 \cdot 10^{-1}$) | $3.6 \cdot 10^{-2}$ ($6.5 \cdot 10^{-3} - 1.8 \cdot 10^{-1}$) | $11.2 \cdot 10^{-2}$ ($1.4 \cdot 10^{-2} - 3.2 \cdot 10^{-1}$) |
| h mRNA/cyno mRNA | $2.7 \cdot 10^{-3}$ ($7.3 \cdot 10^{-4} - 1.1 \cdot 10^{-2}$) | $2.5 \cdot 10^{-3}$ ($4.5 \cdot 10^{-4} - 2.7 \cdot 10^{-2}$) | $9.0 \cdot 10^{-3}$ ($1.0 \cdot 10^{-3} - 2.7 \cdot 10^{-2}$) |
| cyno mRNA/GAPDH mRNA | 9.3 (0.9–23.5) | 18.1 (4.1–44.2) | 12.3 (6.9–18.0) |
| Sal-human/Sal-cyno peptide ratio (mass spec proteomics) | $1.28 \cdot 10^{-2}$ | $2.38 \cdot 10^{-2}$ | — |

FIG. 63

SEQUENCE LISTING

<160> NUMBER OF SEQ ID NOS: 51

<210> SEQ ID NO 1
<211> LENGTH: 495
<212> TYPE: PRT
<213> ORGANISM: Homo sapiens

<400> SEQUENCE: 1

```
Met Leu Leu Leu Gly Leu Leu Leu Leu Pro Leu Leu Ala Gly Ala
1               5                   10                  15

Arg Leu Leu Trp Asn Trp Trp Lys Leu Arg Ser Leu His Leu Pro Pro
            20                  25                  30

Leu Ala Pro Gly Phe Leu His Leu Leu Gln Pro Asp Leu Pro Ile Tyr
            35                  40                  45

Leu Leu Gly Leu Thr Gln Lys Phe Gly Pro Ile Tyr Arg Leu His Leu
50                  55                  60

Gly Leu Gln Asp Val Val Leu Asn Ser Lys Arg Thr Ile Glu Glu
65                  70                  75                  80

Ala Met Val Lys Lys Trp Ala Asp Phe Ala Gly Arg Pro Glu Pro Leu
                85                  90                  95

Thr Tyr Lys Leu Val Ser Arg Asn Tyr Pro Asp Leu Ser Leu Gly Asp
            100                 105                 110

Tyr Ser Leu Leu Trp Lys Ala His Lys Lys Leu Thr Arg Ser Ala Leu
            115                 120                 125

Leu Leu Gly Ile Arg Asp Ser Met Glu Pro Val Val Glu Gln Leu Thr
130                 135                 140

Gln Glu Phe Cys Glu Arg Met Arg Ala Gln Pro Gly Thr Pro Val Ala
145                 150                 155                 160

Ile Glu Glu Glu Phe Ser Leu Leu Thr Cys Ser Ile Ile Cys Tyr Leu
                165                 170                 175

Thr Phe Gly Asp Lys Ile Lys Asp Asp Asn Leu Met Pro Ala Tyr Tyr
            180                 185                 190

Lys Cys Ile Gln Glu Val Leu Lys Thr Trp Ser His Trp Ser Ile Gln
            195                 200                 205

Ile Val Asp Val Ile Pro Phe Leu Arg Phe Phe Pro Asn Pro Gly Leu
210                 215                 220

Arg Arg Leu Lys Gln Ala Ile Glu Lys Arg Asp His Ile Val Glu Met
225                 230                 235                 240

Gln Leu Arg Gln His Lys Glu Ser Leu Val Ala Gly Gln Trp Arg Asp
                245                 250                 255

Met Met Asp Tyr Met Leu Gln Gly Val Ala Gln Pro Ser Met Glu Glu
            260                 265                 270

Gly Ser Gly Gln Leu Leu Glu Gly His Val His Met Ala Ala Val Asp
            275                 280                 285

Leu Leu Ile Gly Gly Thr Glu Thr Thr Ala Asn Thr Leu Ser Trp Ala
            290                 295                 300

Val Val Phe Leu Leu His His Pro Glu Ile Gln Gln Arg Leu Gln Glu
305                 310                 315                 320

Glu Leu Asp His Glu Leu Gly Pro Gly Ala Ser Ser Ser Arg Val Pro
                325                 330                 335

Tyr Lys Asp Arg Ala Arg Leu Pro Leu Leu Asn Ala Thr Ile Ala Glu
            340                 345                 350

Val Leu Arg Leu Arg Pro Val Val Pro Leu Ala Leu Pro His Arg Thr
            355                 360                 365
```

```
Thr Arg Pro Ser Ser Ile Ser Gly Tyr Asp Ile Pro Glu Gly Thr Val
    370             375                 380

Ile Ile Pro Asn Leu Gln Gly Ala His Leu Asp Glu Thr Val Trp Glu
385             390                 395                 400

Arg Pro His Glu Phe Trp Pro Asp Arg Phe Leu Glu Pro Gly Lys Asn
            405                 410                 415

Ser Arg Ala Leu Ala Phe Gly Cys Gly Ala Arg Val Cys Leu Gly Glu
            420                 425             430

Pro Leu Ala Arg Leu Glu Leu Phe Val Val Leu Thr Arg Leu Leu Gln
            435             440                 445

Ala Phe Thr Leu Leu Pro Ser Gly Asp Ala Leu Pro Ser Leu Gln Pro
450                 455                 460

Leu Pro His Cys Ser Val Ile Leu Lys Met Gln Pro Phe Gln Val Arg
465             470                 475                 480

Leu Gln Pro Arg Gly Met Gly Ala His Ser Pro Gly Gln Ser Gln
                485                 490                 495

<210> SEQ ID NO 2
<211> LENGTH: 584
<212> TYPE: DNA
<213> ORGANISM: Unknown
<220> FEATURE:
<223> OTHER INFORMATION: CAG promoter

<400> SEQUENCE: 2
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggtcga ggtgagcccc acgttctgct tcactctccc catctccccc cctccccac    360 ccccaatttt gtatttattt attttttaat tattttgtgc agcgatgggg gcgggggggg   420 gggggggggcg cgcgccaggc ggggcgggc ggggcgaggg gcgggcggg gcgaggcgga   480 gaggtgcggc ggcagccaat cagagcggcg cgctccgaaa gtttccttttt atggcgaggc   540 ggcggcggcg gcggccctat aaaaagcgaa gcgcgcggcg ggcg                    584

<210> SEQ ID NO 3
<211> LENGTH: 399
<212> TYPE: DNA
<213> ORGANISM: Unknown
<220> FEATURE:
<223> OTHER INFORMATION: PGK promoter

<400> SEQUENCE: 3
ccggtaggcg ccaaccggct ccgttctttg gtggccccct tcgcgccacct tctactcctc    60 ccctagtcag gaagttcccc cccgccccgc agctcgcgtc gtgcaggacg tgacaaatgg   120
aagtagcacg tctcactagt ctcgtgcaga tggacagcac cgctgagcaa tggaagcggg   180
taggcctttg gggcagcggc caatagcagc tttgctcctt cgctttctgg gctcagaggc   240
tgggaagggg tgggtccggg ggcgggctca ggggcgggct caggggcggg gcgggcgccc   300
gaaggtcctc cggaggcccg gcattctgca cgcttcaaaa gcgcacgtct gccgcgctgt   360
tctcctcttc ctcatctccg ggcctttcga cctgcagcc                          399
```

-continued

```
<210> SEQ ID NO 4
<211> LENGTH: 23
<212> TYPE: DNA
<213> ORGANISM: Artificial Sequence
<220> FEATURE:
<223> OTHER INFORMATION: CYP21A2 transgene primer

<400> SEQUENCE: 4
acagtcatca ttccgaacct cca                                               23

<210> SEQ ID NO 5
<211> LENGTH: 23
<212> TYPE: DNA
<213> ORGANISM: Artificial Sequence
<220> FEATURE:
<223> OTHER INFORMATION: CYP21A2 transgene primer

<400> SEQUENCE: 5
aaggccagag ctctggagtt ctt                                               23

<210> SEQ ID NO 6
<211> LENGTH: 23
<212> TYPE: DNA
<213> ORGANISM: Artificial Sequence
<220> FEATURE:
<223> OTHER INFORMATION: mouse brain-derived neurotrophic factor primer

<400> SEQUENCE: 6
tgctggatga ggaccagaag gtt                                               23

<210> SEQ ID NO 7
<211> LENGTH: 22
<212> TYPE: DNA
<213> ORGANISM: Artificial Sequence
<220> FEATURE:
<223> OTHER INFORMATION: mouse brain-derived neurotrophic factor primer

<400> SEQUENCE: 7
aggaggctcc aaaggcactt ga                                                22

<210> SEQ ID NO 8
<211> LENGTH: 20
<212> TYPE: DNA
<213> ORGANISM: Artificial Sequence
<220> FEATURE:
<223> OTHER INFORMATION: Mc2r primer

<400> SEQUENCE: 8
tttctcagtc atcttgccga                                                   20

<210> SEQ ID NO 9
<211> LENGTH: 20
<212> TYPE: DNA
<213> ORGANISM: Artificial Sequence
<220> FEATURE:
<223> OTHER INFORMATION: Mc2r primer

<400> SEQUENCE: 9
atgctcctct ccttggcttt                                                   20

<210> SEQ ID NO 10
<211> LENGTH: 21
<212> TYPE: DNA
<213> ORGANISM: Artificial Sequence
<220> FEATURE:
<223> OTHER INFORMATION: Prkar1a primer
```

```
<400> SEQUENCE: 10
gcattccttc gggaatactt t                                        21

<210> SEQ ID NO 11
<211> LENGTH: 20
<212> TYPE: DNA
<213> ORGANISM: Artificial Sequence
<220> FEATURE:
<223> OTHER INFORMATION: Prkar1a primer

<400> SEQUENCE: 11
ccctcgagtc agtacggatg                                          20

<210> SEQ ID NO 12
<211> LENGTH: 20
<212> TYPE: DNA
<213> ORGANISM: Artificial Sequence
<220> FEATURE:
<223> OTHER INFORMATION: Prkar2a primer

<400> SEQUENCE: 12
gagtgactcg gactcggaag                                          20

<210> SEQ ID NO 13
<211> LENGTH: 20
<212> TYPE: DNA
<213> ORGANISM: Artificial Sequence
<220> FEATURE:
<223> OTHER INFORMATION: Prkar2a primer

<400> SEQUENCE: 13
cctcctcttc ttcatcaggg                                          20

<210> SEQ ID NO 14
<211> LENGTH: 18
<212> TYPE: DNA
<213> ORGANISM: Artificial Sequence
<220> FEATURE:
<223> OTHER INFORMATION: Prkarca primer

<400> SEQUENCE: 14
aagaagggca gcgagcag                                            18

<210> SEQ ID NO 15
<211> LENGTH: 20
<212> TYPE: DNA
<213> ORGANISM: Artificial Sequence
<220> FEATURE:
<223> OTHER INFORMATION: Prkarca primer

<400> SEQUENCE: 15
attctgagaa ggggtctccc                                          20

<210> SEQ ID NO 16
<211> LENGTH: 19
<212> TYPE: DNA
<213> ORGANISM: Artificial Sequence
<220> FEATURE:
<223> OTHER INFORMATION: Prkarcb primer

<400> SEQUENCE: 16
caagaaaggc agcgaagtg                                           19

<210> SEQ ID NO 17
<211> LENGTH: 20
```

```
<212> TYPE: DNA
<213> ORGANISM: Artificial Sequence
<220> FEATURE:
<223> OTHER INFORMATION: Prkarcb primer

<400> SEQUENCE: 17
tcctcaagcc cagcattact                                              20

<210> SEQ ID NO 18
<211> LENGTH: 20
<212> TYPE: DNA
<213> ORGANISM: Artificial Sequence
<220> FEATURE:
<223> OTHER INFORMATION: Sf1 primer

<400> SEQUENCE: 18
gccaggagtt cgtctgtctc                                              20

<210> SEQ ID NO 19
<211> LENGTH: 19
<212> TYPE: DNA
<213> ORGANISM: Artificial Sequence
<220> FEATURE:
<223> OTHER INFORMATION: Sf1 primer

<400> SEQUENCE: 19
tttcctgggc gtcctttac                                               19

<210> SEQ ID NO 20
<211> LENGTH: 20
<212> TYPE: DNA
<213> ORGANISM: Artificial Sequence
<220> FEATURE:
<223> OTHER INFORMATION: Star primer

<400> SEQUENCE: 20
gggcatactc aacaaccagg                                              20

<210> SEQ ID NO 21
<211> LENGTH: 20
<212> TYPE: DNA
<213> ORGANISM: Artificial Sequence
<220> FEATURE:
<223> OTHER INFORMATION: Star primer

<400> SEQUENCE: 21
gaaacacctt gcccacatct                                              20

<210> SEQ ID NO 22
<211> LENGTH: 20
<212> TYPE: DNA
<213> ORGANISM: Artificial Sequence
<220> FEATURE:
<223> OTHER INFORMATION: Cyp11a1 primer

<400> SEQUENCE: 22
caggccaaca ttaccgagat                                              20

<210> SEQ ID NO 23
<211> LENGTH: 20
<212> TYPE: DNA
<213> ORGANISM: Artificial Sequence
<220> FEATURE:
<223> OTHER INFORMATION: Cyp11a1 primer
```

<400> SEQUENCE: 23
ccttcaagtt gtgtgccatc                                           20

<210> SEQ ID NO 24
<211> LENGTH: 20
<212> TYPE: DNA
<213> ORGANISM: Artificial Sequence
<220> FEATURE:
<223> OTHER INFORMATION: Hsd3b1 primer

<400> SEQUENCE: 24
gttgtcatcc acactgctgc                                           20

<210> SEQ ID NO 25
<211> LENGTH: 20
<212> TYPE: DNA
<213> ORGANISM: Artificial Sequence
<220> FEATURE:
<223> OTHER INFORMATION: Hsd3b1 primer

<400> SEQUENCE: 25
caggcctcca ataggttctg                                           20

<210> SEQ ID NO 26
<211> LENGTH: 24
<212> TYPE: DNA
<213> ORGANISM: Artificial Sequence
<220> FEATURE:
<223> OTHER INFORMATION: Cyp11b1 primer

<400> SEQUENCE: 26
atggactttc agtccagtgt gttc                                      24

<210> SEQ ID NO 27
<211> LENGTH: 18
<212> TYPE: DNA
<213> ORGANISM: Artificial Sequence
<220> FEATURE:
<223> OTHER INFORMATION: Cyp11b1 primer

<400> SEQUENCE: 27
gccgctcccc aaaaagaa                                             18

<210> SEQ ID NO 28
<211> LENGTH: 20
<212> TYPE: DNA
<213> ORGANISM: Artificial Sequence
<220> FEATURE:
<223> OTHER INFORMATION: Cyp17a1 primer

<400> SEQUENCE: 28
gaagtgctcg tgaagaaggg                                           20

<210> SEQ ID NO 29
<211> LENGTH: 20
<212> TYPE: DNA
<213> ORGANISM: Artificial Sequence
<220> FEATURE:
<223> OTHER INFORMATION: Cyp17a1 primer

<400> SEQUENCE: 29
ctactatccg caaaggcgac                                           20

<210> SEQ ID NO 30

```
<211> LENGTH: 20
<212> TYPE: DNA
<213> ORGANISM: Artificial Sequence
<220> FEATURE:
<223> OTHER INFORMATION: Cyp11b2 primer

<400> SEQUENCE: 30
gagacgtggt gtgttcttgc                                              20

<210> SEQ ID NO 31
<211> LENGTH: 20
<212> TYPE: DNA
<213> ORGANISM: Artificial Sequence
<220> FEATURE:
<223> OTHER INFORMATION: Cyp11b2 primer

<400> SEQUENCE: 31
tcccttgcta ccatgtccac                                              20

<210> SEQ ID NO 32
<211> LENGTH: 23
<212> TYPE: DNA
<213> ORGANISM: Artificial Sequence
<220> FEATURE:
<223> OTHER INFORMATION: CYP21 primer

<400> SEQUENCE: 32
acagtcatca ttccgaacct cca                                          23

<210> SEQ ID NO 33
<211> LENGTH: 23
<212> TYPE: DNA
<213> ORGANISM: Artificial Sequence
<220> FEATURE:
<223> OTHER INFORMATION: CYP21 primer

<400> SEQUENCE: 33
aaggccagag ctctggagtt ctt                                          23

<210> SEQ ID NO 34
<211> LENGTH: 20
<212> TYPE: DNA
<213> ORGANISM: Artificial Sequence
<220> FEATURE:
<223> OTHER INFORMATION: Renin primer

<400> SEQUENCE: 34
ctctgggcac tcttgttgct                                              20

<210> SEQ ID NO 35
<211> LENGTH: 20
<212> TYPE: DNA
<213> ORGANISM: Artificial Sequence
<220> FEATURE:
<223> OTHER INFORMATION: Renin primer

<400> SEQUENCE: 35
agaaggcatt ttcttgagcg                                              20

<210> SEQ ID NO 36
<211> LENGTH: 23
<212> TYPE: DNA
<213> ORGANISM: Artificial Sequence
<220> FEATURE:
<223> OTHER INFORMATION: Tbp primer
```

```
<400> SEQUENCE: 36 ccccttgtacc cttcaccaat gac                                      23

<210> SEQ ID NO 37
<211> LENGTH: 28
<212> TYPE: DNA
<213> ORGANISM: Artificial Sequence
<220> FEATURE:
<223> OTHER INFORMATION: Tbp primer

<400> SEQUENCE: 37
tcacggtaga tacaatattt tgaagctg                                  28

<210> SEQ ID NO 38
<211> LENGTH: 21
<212> TYPE: DNA
<213> ORGANISM: Homo sapiens

<400> SEQUENCE: 38
aaattcgggc ccatctacag g                                         21

<210> SEQ ID NO 39
<211> LENGTH: 21
<212> TYPE: DNA
<213> ORGANISM: Homo sapiens

<400> SEQUENCE: 39
atggcttcct caatggtcct c                                         21

<210> SEQ ID NO 40
<211> LENGTH: 23
<212> TYPE: DNA
<213> ORGANISM: Macaca fascicularis

<400> SEQUENCE: 40
ctgtcatgct gctgctgaga ctt                                       23

<210> SEQ ID NO 41
<211> LENGTH: 24
<212> TYPE: DNA
<213> ORGANISM: Macaca fascicularis

<400> SEQUENCE: 41
ctttggcata gcattcatga ggat                                      24

<210> SEQ ID NO 42
<211> LENGTH: 23
<212> TYPE: DNA
<213> ORGANISM: Mus musculus

<400> SEQUENCE: 42
tgctggatga ggaccagaag gtt                                       23

<210> SEQ ID NO 43
<211> LENGTH: 22
<212> TYPE: DNA
<213> ORGANISM: Mus musculus

<400> SEQUENCE: 43
aggaggctcc aaaggcactt ga                                        22

<210> SEQ ID NO 44
```

```
<211> LENGTH: 7
<212> TYPE: RNA
<213> ORGANISM: Unknown
<220> FEATURE:
<223> OTHER INFORMATION: Kozak sequence

<400> SEQUENCE: 44 accaugg                                                                    7

<210> SEQ ID NO 45
<211> LENGTH: 13
<212> TYPE: RNA
<213> ORGANISM: Unknown
<220> FEATURE:
<223> OTHER INFORMATION: Kozak sequence

<400> SEQUENCE: 45
gccgccacca ugg                                                            13

<210> SEQ ID NO 46
<211> LENGTH: 8
<212> TYPE: RNA
<213> ORGANISM: Unknown
<220> FEATURE:
<223> OTHER INFORMATION: Kozak sequence

<400> SEQUENCE: 46 ccaccaug                                                                   8

<210> SEQ ID NO 47
<211> LENGTH: 9
<212> TYPE: RNA
<213> ORGANISM: Unknown
<220> FEATURE:
<223> OTHER INFORMATION: Kozak sequence

<400> SEQUENCE: 47 ccaccaugg                                                                  9

<210> SEQ ID NO 48
<211> LENGTH: 260
<212> TYPE: DNA
<213> ORGANISM: Unknown
<220> FEATURE:
<223> OTHER INFORMATION: CB6 Promoter

<400> SEQUENCE: 48
ccacgttctg cttcactctc cccatctccc cccccteccc accccaatt ttgtatttat           60 ttatttttta attatttttgt gcagcgatgg gggcggggg ggggggcgcg cgccaggcgg         120
ggcggggcgg ggcgaggggc ggggcgggc gaggcggaga ggtgcggcgg cagccaatca          180
gagcggcgcg ctccgaaagt ttccttttat ggcgaggcgg cggcggcggc ggccctataa         240
aaagcgaagc gcgcggcggg                                                    260

<210> SEQ ID NO 49
<211> LENGTH: 282
<212> TYPE: DNA
<213> ORGANISM: Unknown
<220> FEATURE:
<223> OTHER INFORMATION: CBA Promoter

<400> SEQUENCE: 49
tggtcgaggt gagccccacg ttctgcttca ctctccccat ctccccccc tccccacccc           60 caattttgta tttatttatt ttttaattat tttgtgcagc gatggggcg gggggggggg         120
```

```
ggggggcgcgc gccaggcggg gcggggcggg gcgaggggcg gggcggggcg aggcggagag    180
gtgcggcggc agccaatcag agcggcgcgc tccgaaagtt tccttttatg gcgaggcggc    240
ggcggcggcg gccctataaa aagcgaagcg cgcggcgggc gg                       282
```

<210> SEQ ID NO 50
<211> LENGTH: 1488
<212> TYPE: DNA
<213> ORGANISM: Artificial Sequence
<220> FEATURE:
<223> OTHER INFORMATION: Codon Optimized CYP21a2 gene sequence

<400> SEQUENCE: 50

```
atgctgctgc tggggctgct gctgctgctg cctctgctgg ctggggctcg actgctgtgg     60
aactggtgga aactgcggtc cctgcacctg ccacctctgg caccaggctt cctgcacctg    120
ctgcagccag acctgcccat ctacctgctg ggcctgaccc agaagtttgg ccctatctat    180
aggctgcacc tgggcctgca ggacgtggtg gtgctgaact ctaagcgcac catcgaggag    240
gccatggtga agaagtgggc agatttcgca ggccggccag agccactgac atacaagctg    300
gtgagcagaa attatcctga cctgtccctg ggcgattact ctctgctgtg gaaggcccac    360
aagaagctga caaggagcgc cctgctgctg ggcatccgcg actccatgga gccagtggtg    420
gagcagctga cccaggagtt ttgcgagagg atgagggcac agcctggaac accagtggcc    480
atcgaggagg agttcagcct gctgacctgc tccatcatct gttatctgac atttggcgat    540
aagatcaagg acgataacct gatgccagcc tactataagt gtatccagga ggtgctgaag    600
acctggagcc actggagcat ccagatcgtg gacgtgatcc ccttcctgag gttctttcct    660
aatccaggcc tgcggagact gaagcaggcc atcgagaaga gggatcacat cgtggagatg    720
cagctgaggc agcacaagga gtccctggtg gcaggacagt ggagggacat gatggattac    780
atgctgcagg gagtggcaca gccatctatg gaggagggaa gcggacagct gctggaggga    840
cacgtgcaca tggcagcagt ggatctgctg atcggaggaa ccgagacaac agccaacaca    900
ctgagctggg ccgtggtgtt tctgctgcac caccctgaga tccagcagcg gctgcaggag    960
gagctggacc acgagctggg aacctggagca agctcctcta gagtgccata caaggatcgg   1020
gccagactgc ccctgctgaa tgccaccatc gccgaggtgc tgaggctgcg ccccgtggtg   1080
cctctggccc tgcctcacag gaccacaaga ccaagctcca tctccggcta tgacatccca   1140
gagggcaccg tgatcatccc aaacctgcag ggagcacacc tggacgagac agtgtgggag   1200
cggccacacg agttctggcc cgatagattt ctggagcctg caagaacag ccgggccctg   1260 gccttcggct gcggagcccg ggtgtgcctg ggcgagccac tggccaggct ggagctgttc   1320
gtggtgctga cccgcctgct gcaggccttt acactgctgc cctccggcga tgccctgcct   1380
tctctgcagc cactgcctca ctgctccgtg atcctgaaga tgcagcccct tcaggtccgc   1440
ctgcagccaa gggggatggg ggcacatagt ccagggcagt ctcagtaa                1488
```

<210> SEQ ID NO 51
<211> LENGTH: 592
<212> TYPE: DNA
<213> ORGANISM: Marmota monax

<400> SEQUENCE: 51

```
aatcaacctc tggattacaa aatttgtgaa agattgactg atattcttaa ctatgttgct     60
ccttttacgc tgtgtggata tgctgcttta atgcctctgt atcatgctat tgcttcccgt    120
```

```
acggctttcg ttttctcctc cttgtataaa tcctggttgc tgtctcttta tgaggagttg    180
tggcccgttg tccgtcaacg tggcgtggtg tgctctgtgt ttgctgacgc aaccccact     240 ggctggggca ttgccaccac ctgtcaactc ctttctggga ctttcgcttt cccctcccg     300 atcgccacgg cagaactcat cgccgcctgc cttgcccgct gctggacagg ggctaggttg    360
ctgggcactg ataattccgt ggtgttgtcg gggaagctga cgtcctttcc atggctgctc    420
gcctgtgttg ccaactggat cctgcgcggg acgtccttct gctacgtccc ttcggctctc    480
aatccagcgg acctcccttc ccgaggcctt ctgccggttc tgcggcctct cccgcgtctt    540
cgctttcggc ctccgacgag tcggatctcc ctttgggccg cctccccgcc tg            592
```

ADENO-ASSOCIATED VIRUS GENE THERAPY FOR 21-HYDROXYLASE DEFICIENCY

This application is a 35 U.S.C. § 371 national phase application of International Patent Application No. PCT/US2019/013991, filed on Jan. 17, 2019, which claims priority to and benefit of U.S. Provisional Patent Application No. 62/640,311, filed on Mar. 8, 2018, and U.S. Provisional Patent Application No. 62/618,307, filed on Jan. 17, 2018. The contents of each of these applications are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ADRE_001_02US_SeqList_ST25.txt, date recorded: Jul. 16, 2019, file size ~18,067 bytes).

FIELD OF THE INVENTION

The present disclosure relates generally to the field of gene therapy. In particular, the disclosure describes recombinant adeno-associated virus (rAAV) vectors and particles that express 21-hydroxylase (21OH) protein. The rAAV vectors and particles may be used to treat 21OH deficiency.

BACKGROUND OF THE INVENTION 21-hydroxylase (21OH) is a cytochrome P450 enzyme, encoded by the CYP21A2 gene, that is involved with the biosynthesis of the steroid hormones aldosterone and cortisol. These syntheses take place in the adrenal cortex. The high rate of recombination between the functional CYP21A2 gene and the closely linked, non-functional CYP21A1P pseudogene results in the high incidence of congenital adrenal hyperplasia (CAH) and its unusual genetics, driven by gene conversions rather than by point mutations. Defects in CYP21A2 cause 21-hydroxylase deficiency (21OHD), which leads either to i) CAH with fetal masculinization of external genitals, low or absent glucocorticoid and mineralocorticoid production, and large excess of androgens ("classical" 21OHD) or ii) milder forms of the disease without fetal masculinization, without cortisol and aldosterone deficits, but with increased production of androgens ("non-classical" 21OHD).

After decades of therapeutic strategies, management of severe forms of 21OHD remains clinically challenging. While patients can be treated with exogenous steroids, infant and adult patients remain at risk for adrenal crisis—the inability of their adrenal glands to respond to bodily stress such as routine infection, trauma, or intense exertion. Adrenal crisis can lead rapidly to severe shock and death even in well-educated patients who are compliant with therapy. See, Hahner et al., *J Clin Endocrinol Metab*, February; 100(2): 407-416 (2015). Additionally, there are significant consequences related to growth, gender, and sexuality. In female patients, there is an inherent difficulty of suppressing adrenal androgen production using supra-physiological glucocorticoid doses. As a result, alternating cycles of androgen versus glucocorticoid excess may lead to short stature, obesity, repeated genital surgery during childhood, alterations in puberty and chronic virilization. Hyperandrogenism remains the main cosmetic burden for female patients affected with classical and non-classical forms of the disease through hirsutism, male muscular development, enlarged clitoris size and impaired sexuality. See, Gastaud et al., *J Clin Endocrinol Metab*, 92(4), 1391-1396 (2007). Male patients are at risk for short stature and premature virilization. Therapeutic failure may even lead to bilateral adrenalectomy in some patients (Gmyrek et al., *Pediatrics*, 109: E28 (2002); Bruining et al., *J Clin Endocrinol Metab*, 86: 482-484 (2001)).

There remains a need for therapies that allow for persistent correction of 21OHD.

SUMMARY OF THE INVENTION

The invention encompasses a recombinant adeno-associated virus (rAAV) vector comprising a nucleic acid molecule comprising at least one AAV inverted terminal repeat (ITR) and a non-AAV nucleotide sequence encoding a 21-hydroxylase (21OH) protein, the non-AAV nucleotide sequence operably linked to a promoter.

In certain cases, a rAAV vector encodes a 21OH protein that is human 21OH protein. In some embodiments, a non-AAV nucleotide sequence encoding a 21OH protein comprises or consists of the human 21OH (CYP21A2) cDNA. In certain embodiments, a non-AAV nucleotide sequence encoding a 21OH protein encodes the amino acid sequence of SEQ ID NO:1 or an amino acid sequence at least 95%, at least 96%, at least 97%, at least 98% or at least 99% identical to SEQ ID NO: 1.

A rAAV vector may comprise a nucleic acid molecule comprising at least one AAV inverted terminal repeat (ITR) and a non-AAV nucleotide sequence encoding a 21-hydroxylase (21OH) protein, the non-AAV nucleotide sequence operably linked to a promoter, wherein the promoter directs expression of the 21OH protein in a host cell (e.g., an adrenal gland cell or an adrenal cortex cell). Non-limiting examples of suitable promoters include a cytomegalovirus/0-actin hybrid promoter, PGK promoter or a promoter specific for expression in an adrenal cortex cell. In some embodiments, a cytomegalovirus/β-actin hybrid promoter is a CAG, CB6 or CBA promoter. In some embodiments, a promoter comprises or consists of the nucleotide sequence of SEQ ID NO:2, SEQ ID NO:3, SEQ ID NO:48 or SEQ ID NO:49.

In some aspects, a rAAV vector comprises at least one ITR sequence. In certain embodiments, an ITR is an AAV1, AAV2, AAV3, AAV4, AAV5, AAV6, AAV7, AAV8, AAV9, AAV10, AAV11, AAV12, rh10 or rh74 serotype ITR.

In certain cases, a rAAV vector of the invention is an AAV1, AAV2, AAV3, AAV4, AAV5, AAV6, AAV7, AAV8, AAV9, AAV10, AAV11, AAV12, rh10 or rh74 serotype.

The invention further provides a recombinant adeno-associated virus (rAAV) vector comprising a nucleic acid molecule comprising a non-AAV nucleotide sequence encoding a 21-hydroxylase (21OH) protein, the non-AAV nucleotide sequence operably linked to a promoter, wherein the rAAV vector comprises at least one AAV inverted terminal repeat (ITR), wherein the ITR is from an AAV of serotype AAV1, AAV2, AAV3, AAV4, AAV5, AAV6, AAV7, AAV8, AAV9, AAV10, AAV11, AAV12, rh10 or rh74; and wherein the promoter is a cytomegalovirus/0-actin hybrid promoter, a PGK promoter or a promoter specific for expression in an adrenal cortex cell. In some embodiments, a cytomegalovirus/β-actin hybrid promoter is a CAG, CB6 or CBA promoter.

In some aspects, the invention encompasses a rAAV particle comprising a rAAV vector described herein. In certain embodiments, a rAAV particle further comprises at least one capsid protein from AAV serotype AAV1, AAV2, AAV3, AAV4, AAV5, AAV6, AAV7, AAV8, AAV9, AAV10, AAV11, AAV12, rh10 or rh74.

The invention also encompasses a pharmaceutical composition comprising a rAAV vector or a rAAV particle described herein and a pharmaceutically acceptable carrier, diluent or excipient. Additionally, the invention contemplates a method of producing an rAAV particle, the method comprising culturing a host cell containing: (a) a rAAV vector described herein; (b) a nucleic acid molecule encoding an AAV rep; (c) a nucleic acid molecule encoding at least one AAV capsid protein and (d) sufficient helper functions for packaging the rAAV particle.

In certain cases, the invention provides a method of expressing 21-hydroxylase (21OH) in a subject in need thereof, comprising administering to the subject a therapeutically effective amount of a rAAV particle comprising a rAAV vector comprising a nucleic acid molecule comprising at least one AAV inverted terminal repeat (ITR) and a non-AAV nucleotide sequence encoding a 21-hydroxylase (21OH) protein, the non-AAV nucleotide sequence operably linked to a promoter, or a pharmaceutical composition comprising such a rAAV particle, thereby expressing 21OH in the subject. In some cases, 21OH may be expressed in the subject's adrenal cortex, adrenal medulla, adrenal stem cells, adrenal progenitor cells, liver or ovary.

The invention further provides a method of treating a subject with 21-hydroxylase deficiency (21OHD), comprising administering to the subject a therapeutically effective amount of a rAAV particle comprising a rAAV vector comprising a nucleic acid molecule comprising at least one AAV inverted terminal repeat (ITR) and a non-AAV nucleotide sequence encoding a 21-hydroxylase (21OH) protein, the non-AAV nucleotide sequence operably linked to a promoter, or a pharmaceutical composition comprising such a rAAV particle, thereby treating 21OHD in the subject. This method may further comprise selecting a subject with 21OHD before the administering step.

In some cases, a rAAV vector or a rAAV particle or a pharmaceutical composition comprising such a rAAV vector or rAAV particle is administered to the subject intravenously, by direct injection into the adrenal gland via open surgery or laparoscopy or by injection into an adrenal artery via catheterization. Direct injection into the adrenal gland may be direct injection into the adrenal cortex.

A subject treated by the methods or the compositions of the invention may be affected with the Prader stage IV or V form of 21OHD. In some cases, a subject is affected with congenital adrenal hyperplasia (CAH).

The invention also contemplates a use of a rAAV vector comprising a nucleic acid molecule comprising at least one AAV inverted terminal repeat (ITR) and a non-AAV nucleotide sequence encoding a 21-hydroxylase (21OH) protein or a rAAV particle comprising such a vector, the non-AAV nucleotide sequence operably linked to a promoter, in the manufacture of a medicament for treating 21-hydroxylase deficiency.

BRIEF DESCRIPTION OF THE DRAWINGS

FIG. 1A-FIG. 1C show the evolution of body weight and urinary progesterone in Cyp21$^{-/-}$ mice injected with CYP21 vector (gray, n=16) or sham vector (black, n=9) compared with Cyp21$^{-/-}$ and Cyp21$^{+/+}$ considered as 'control' mice (white, n=21). FIG. 1A is a bar graph showing that Cyp21$^{-/-}$ mice injected with the sham vector remained smaller than control mice at all times (P<0.001). Mice injected with the CYP21 vector had a substantial recovery of body weight 5 and 10 weeks post-injection (P<0.001) and 15 weeks post-injection (P<0.01). FIG. 1B shows pictures of Cyp21$^{-/-}$ mice injected with the sham vector (left) or CYP21 vector (middle) and a control mouse (right) before vector injection and at the time of killing. FIG. 1C is a bar graph showing that Cyp21$^{-/-}$ mice injected with the sham vector had a much higher urinary progesterone concentration than control mice (P<0.001) at all times. Gene therapy with the CYP21 vector induced a major decrease in urinary progesterone. Correction, however, was not complete. Progesterone levels remained twofold higher, approximatively in the CYP21 treated Cyp21$^{-/-}$ mice compared with the control mice (P<0.001 at 5 weeks post-injection, nonsignificant at 10 weeks post-injection and P<0.05 at 15 weeks post-injection). Data are presented as mean±s.e.m. *P<0.05, P<0.01, *P<0.001.

FIG. 2A-FIG. 2F are bar graphs showing the results of studies of locomotion and stress response in Cyp21$^{-/-}$ mice injected with CYP21 vector (gray, n=14) or sham vector (black, n=13) compared with controls (white, n=19). FIG. 2A shows that Cyp21$^{-/-}$ mice injected with the CYP21 or sham vectors and control mice had comparable locomotor performances as assessed by rotarod. FIG. 2B shows that Cyp21$^{-/-}$ mice injected with the sham vector were more immobile in the tail suspension test than control mice (P=0.21 between control and sham vector mice). Cyp21$^{-/-}$ mice treated with the CYP21 vector recovered a normal response to the test (P<0.05 between control and CYP21 vector mice). FIG. 2C-2F show that Cyp21$^{-/-}$ mice injected with the sham vector traveled on a smaller distance (P<0.001 between control and sham vector mice) (FIG. 2C), spent less time in open arms (non-significant between control and sham vector mice) (FIG. 2D), performed less head-dipping (P<0.05 between control and sham vector mice) (FIG. 2E) and rearing movements (P<0.01 between control and sham vector mice) (FIG. 2F) compared with Cyp21$^{-/-}$ mice injected with the CYP21 vector and control mice in the elevated plus-maze test. Differences were non-significant between controls and CYP21 vector for all the elevated plus-maze parameters. Data are presented as mean±s.e.m. *P<0.05, ***P<0.001.

FIG. 3A shows that mRNA content was decreased in adrenals of CYP21-injected mice versus sham vector for the ACTH receptor (Mc2r), protein kinase A regulatory subunit (Prkar2a), Steroidogenic factor 1 (SF-1) (P<0.01), Steroidogenic acute regulatory protein (Star) and steroidogenic enzymes Cyp17a1 and Cyp11b2 (P<0.05). mRNA content in CYP21-injected mice compared with controls remained increased, although to a lower level for SF-1, Star, Hsd3b1 (P<0.05), Prkar1a, Cyp11b1 (P<0.01), Mc2r, Prkar2a and Cyp11b2 (P<0.001) and was not changed for Prkarca, Prkarcb, Cyp11a1 and Cyp17a1. FIG. 3B shows that Renin mRNA content was decreased in kidneys of CYP21-injected mice versus sham vector (P<0.001) although it remained increased (P<0.001) when CYP21-injected mice were compared with controls. Data are normalized to Tbp and presented as mean s.e.m. *P<0.05, P<0.01, *P<0.001.

FIG. 4A shows that Y1 cells transfected with pCYP21 expressed the 21-hydroxylase as assessed by western blot in contrast to Y1 cells transfected with pLuc. FIG. 4B shows that Y1 cells transfected with pCYP21 had a lower progesterone concentration in supernatant than Y1 cells transfected with pLuc (P=0.10). Data are presented as mean±s.e.m.

FIG. 5A is an image showing the GFP fluorescence pattern of AAVrh10 in adrenal glands following intravenous injection in control mice. FIG. 5B is an immunoblot showing mouse and human 21-hydroxylase expression in adrenal glands of control and Cyp21$^{-/-}$ mice treated with CYP21 vector.

FIG. 8A shows the heart. FIG. 8B shows the liver.

Figure 18:
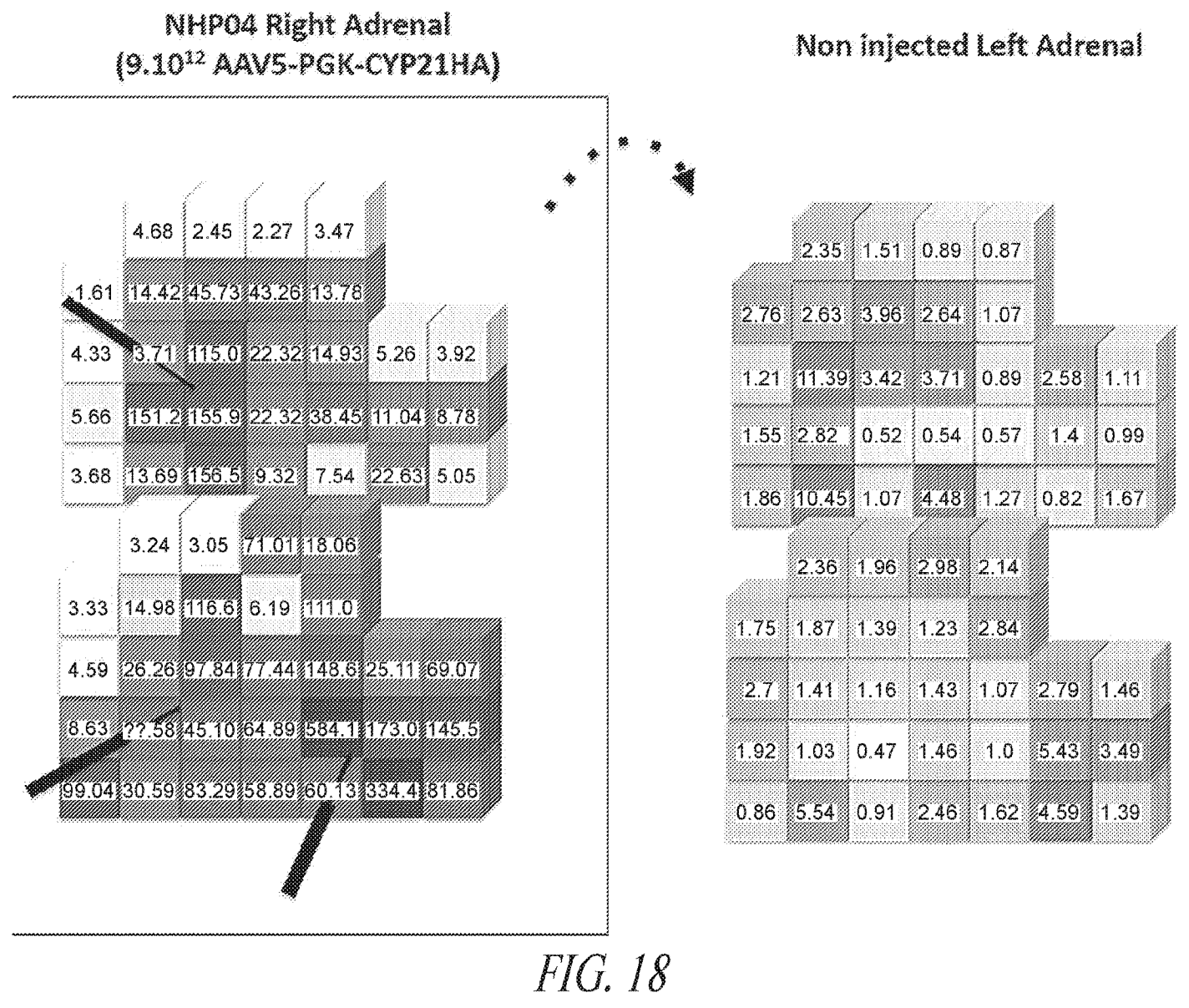

FIG. 18 shows a schematic view of CYP21HA viral genome copy (VGC) measurement spatial distribution in the adrenal glands cut into small pieces from non-human primate number 4 (NHP04) injected with ssAAV5-PGK-CYP21HA in the right adrenal gland. Putative injection sites are indicated as black arrows.

FIG. 19 also shows HA immunofluorescence images of the livers of NHP01, NHP02 and NHP04 injected with ssAAV5-PGK-CYP21HA.

FIG. 20 also shows an immunofluorescence image of an adrenal gland of a wild-type mouse treated with ssAAV5-PGK-GFP intravenously.

FIG. 27 shows a schematic and photographs of the dissection details of the left adrenal of non-human primate number 4 (NHP04) after injection with ssAAV6-CAG-GFP in the left adrenal gland.

Figure 28:
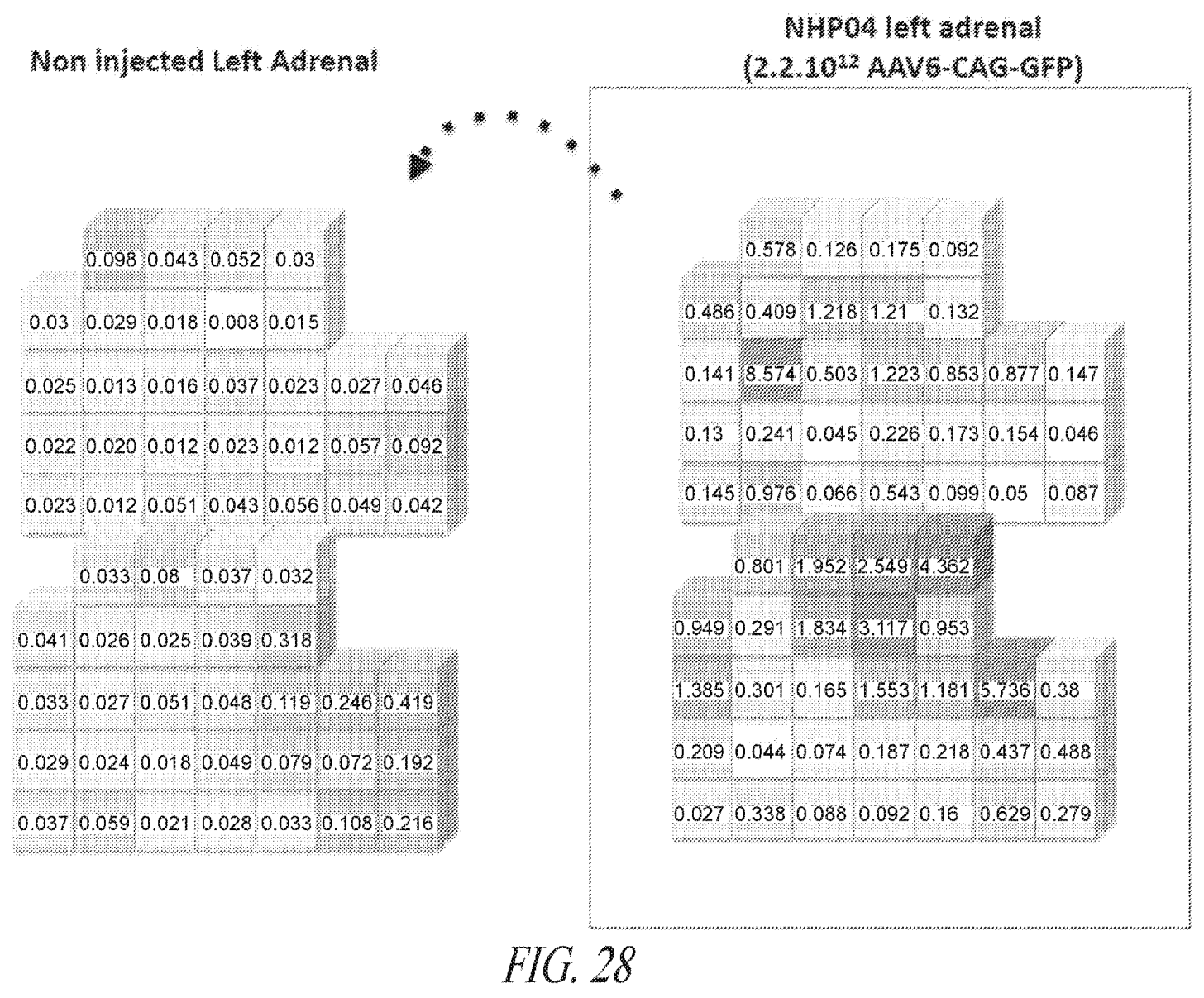

FIG. 28 shows the distribution of GFP VGC measurements spatial distribution in the two adrenal glands cut into small pieces from non-human primate number 4 (NHP04) injected with ssAAV6-CAG-GFP in the left adrenal.

FIG. 29 also shows a GFP immunofluorescence image of the liver of NHP04 injected with ssAAV6-CAG-GFP in the left adrenal.

FIG. 31 also shows a GFP immunofluorescence image of an adrenal gland of a wild-type mouse treated with ssAAV6-CAG-GFP intravenously.

FIG. 35 also shows a GFP immunofluorescence image of the liver of NHP03 injected with ssAAV1-CB6-GFP in the left adrenal.

FIG. 36 also shows a GFP immunofluorescence image of an adrenal gland of a wild-type mouse treated with ssAAV1-CB6-GFP intravenously.

FIG. 39 also shows an HA immunofluorescence image of the liver of NHP03 injected with ssAAV1-PGK-CYP21HA in the right adrenal.

FIG. 43 shows HA-FITC immunofluorescence images of adrenal glands of 7-month-old Cyp21$^{-/-}$ mice treated with ssAAV10-CAG-CYP21HA at 15 weeks post-treatment. "TF" refers to "treated female". "TM" refers to "treated male". The figure includes identification numbers for the mice used to generate the images.

FIG. 46A and FIG. 46B show measurements of urinary progesterone levels (ng/mg creatinine) over 15 weeks in 7-month-old Cyp21$^{-/-}$ mice treated with ssAAV10-CAG-CYP21HA (FIG. 46A) and untreated Cyp21$^{-/-}$ mice (FIG. 46B). FIG. 46C shows measurements of urinary progesterone levels (ng/mg creatinine) over 15 weeks in 7-month-old wild-type mice treated with ssAAV10-CAG-CYP21HA and untreated wild-type mice. The figures include identification numbers for the mice used to generate the data.

FIG. 48 also shows corresponding immunofluorescence images of CYP21HA expression in adrenal glands of the treated mice. "TF" refers to "treated female". "TM" refers to "treated male". The figure includes identification numbers for the mice used to generate the images and data.

FIG. 49A and FIG. 49B show measurements of urinary progesterone levels (ng/mg creatinine) over 15 weeks in 2-3-month-old Cyp21$^{-/-}$ mice treated with ssAAV10-CAG-CYP21HA (FIG. 49A) and untreated Cyp21$^{-/-}$ mice (FIG. 49B). The figures include identification numbers for the mice used to generate the data.

FIG. 52A-FIG. 52C show results obtained after intra-adrenal administration of AAV1-CAG-hCYP21HA to non-human primate number 5 (NHP05), a 28-month-old female weighing 2.65 kg. The animal screened negative for neutralizing antibodies for AAV1, AAV5 and AAV6 about two months before the rAAV administration. The animal screened negative for neutralizing antibodies for AAV1 and AAV5 and screened positive for AAV6 (1/5) about two weeks before the rAAV administration. FIG. 52A shows a schematic view of spatial distribution for CYP21HA vector genome copies (VGC) measurements in different sections of the adrenal glands (left and center). FIG. 52A also shows VGC measurements for each liver lobe (right). FIG. 52B shows distribution of the VGC (left) and mRNA relative to housekeeping gene (ARN) measurements. FIG. 52C shows CYP21HA immunofluorescence images at low (left) and high (right) magnification of the right adrenal gland with CYP21HA positive cell staining (green) indicating wide expression of the vector. "RA" stands for right adrenal. "LA" stands for left adrenal.

FIG. 53A-FIG. 53C show results obtained after intravenous administration of AAV1-CAG-hCYP21HA to non-human primate number 8 (NHP08), a 28-month-old female weighing 2.35 kg. The animal screened negative for neutralizing antibodies for AAV1, AAV5 and AAV6 about two months before the rAAV administration. The animal screened negative for neutralizing antibodies for AAV1 and AAV6 and screened positive for AAV5 (1/5) about two weeks before the rAAV administration. FIG. 53A shows a schematic view of spatial distribution for CYP21HA vector genome copies (VGC) measurements in different sections of the adrenal glands (left and center). FIG. 53A also shows VGC measurements for each liver lobe (right). FIG. 53B shows distribution of the VGC (left) and mRNA relative to housekeeping gene (ARN) measurements. FIG. 53C shows CYP21HA immunofluorescence images at low (left) and high (right) magnification of the right adrenal gland with CYP21HA positive cell staining (green) indicating low expression of the vector. "RA" stands for right adrenal. "LA" stands for left adrenal.

FIG. 54A shows a schematic view of spatial distribution for CYP21HA vector genome copies (VGC) measurements in different sections of the adrenal glands (left and center). FIG. 54A also shows VGC measurements for each liver lobe (right). FIG. 54B shows distribution of the VGC (left) and mRNA relative to housekeeping gene (ARN) measurements. FIG. 54C shows CYP21HA immunofluorescence images at low (large image) and high (smaller images) magnification of the right adrenal gland with CYP21HA positive cell staining (green) indicating wide expression of the vector. "RA" stands for right adrenal. "LA" stands for left adrenal.

FIG. 55A-FIG. 55C show results obtained after intravenous administration of AAV5-CAG-hCYP21HA to non-human primate number 9 (NHP09), a 28-month-old female weighing 2.5 kg. The animal screened negative for neutralizing antibodies for AAV1, AAV5 and AAV6 about two months before the rAAV administration. The animal screened negative for neutralizing antibodies for AAV1, AAV5 and AAV6 about two weeks before the rAAV administration. FIG. 55A shows a schematic view of spatial distribution for CYP21HA vector genome copies (VGC) measurements in different sections of the adrenal glands (left and center). FIG. 55A also shows VGC measurements for each liver lobe (right). FIG. 55B shows distribution of the VGC (left) and mRNA relative to housekeeping gene (ARN) measurements. FIG. 55C shows CYP21HA immunofluorescence images at low (center) and high (left and right) magnification of the right adrenal gland with CYP21HA positive cell staining (green) indicating wide expression of the vector. "RA" stands for right adrenal. "LA" stands for left adrenal.

FIG. 56A shows a schematic view of spatial distribution for CYP21HA vector genome copies (VGC) measurements in different sections of the adrenal glands (left and center). FIG. 56A also shows VGC measurements for each liver lobe (right). FIG. 56A also shows VGC measurements for each liver lobe (right). FIG. 56B shows distribution of the VGC (left) and mRNA relative to housekeeping gene (ARN) measurements. FIG. 56C shows CYP21HA immunofluorescence images at low (left) and high (right) magnification of the right adrenal gland with CYP21HA positive cell staining (green) indicating wide expression of the vector. "RA" stands for right adrenal. "LA" stands for left adrenal.

FIG. 57A shows a schematic view of spatial distribution for CYP21HA vector genome copies (VGC) measurements in different sections of the adrenal glands (left and center). FIG. 57A also shows VGC measurements for each liver lobe (right). FIG. 57B shows distribution of the VGC (left) and mRNA relative to housekeeping gene (ARN) measurements. FIG. 57C shows CYP21HA immunofluorescence images at low (left) and high (right) magnification of the right adrenal gland with CYP21HA positive cell staining (green) indicating minimal expression of the vector. "RA" stands for right adrenal. "LA" stands for left adrenal.

FIG. 58 is a table summarizing data from non-human primates (NHP) with intra-adrenal administered rAAV vector. Listed data includes injection into the right adrenal (RA) or left adrenal (LA), vector identity and dose per kilogram (kg) and the resulting vector genome copies (VGC) measured in the respectively dosed adrenal gland.

FIG. 62 summarizes dosing and treatment groups for non-human primates (NHPs) treated with recombinant serotype AAV5 vectors containing either a wild-type (WT) human CYP21 transgene, a codon-optimized (CO) human CYP21 transgene, or a wild-type cynomolgus CYP21 transgene. All vectors included a CBA promoter and a Kozak sequence. The vectors containing the human CYP21 transgenes further included a miR-122 miRNA binding site for detargeting. The vector containing the wild-type human CYP21 transgene is referred to as "AAV5-CBA-Kozak-hCYP21-miR122". The vector containing the codon-optimized human CYP21 transgene is referred to as "AAV5-CBA-Kozak-COhCYP21-miR122". The vector containing the wild-type cynomolgus CYP21 transgene is referred to as "AAV5-CBA-Kozak-cynoCYP21".

FIG. 63 is a table showing CYP21 vector genome copy (VGC) measurements, mRNA measurements and a Sal-human to Sal-cynomolgus peptide ratio for each non-human primate (NHP) treatment group described in FIG. 62 and Example 13. For the VGC and mRNA rows, the top number in each row is the mean, and the two bottom numbers are the range for the mean. The peptide ratio should not be taken as the exact protein to protein ratio. "h mRNA" refers to human CYP21 mRNA. "cyno mRNA" refers to cynomolgus CYP21 mRNA. The numeric format for exponential numbers is interpreted as shown in the following example: "$1.28 \cdot 10^{-2}$" refers to "$1.28 \times 10^{-2}$".

DETAILED DESCRIPTION OF THE INVENTION

Figure 1B:
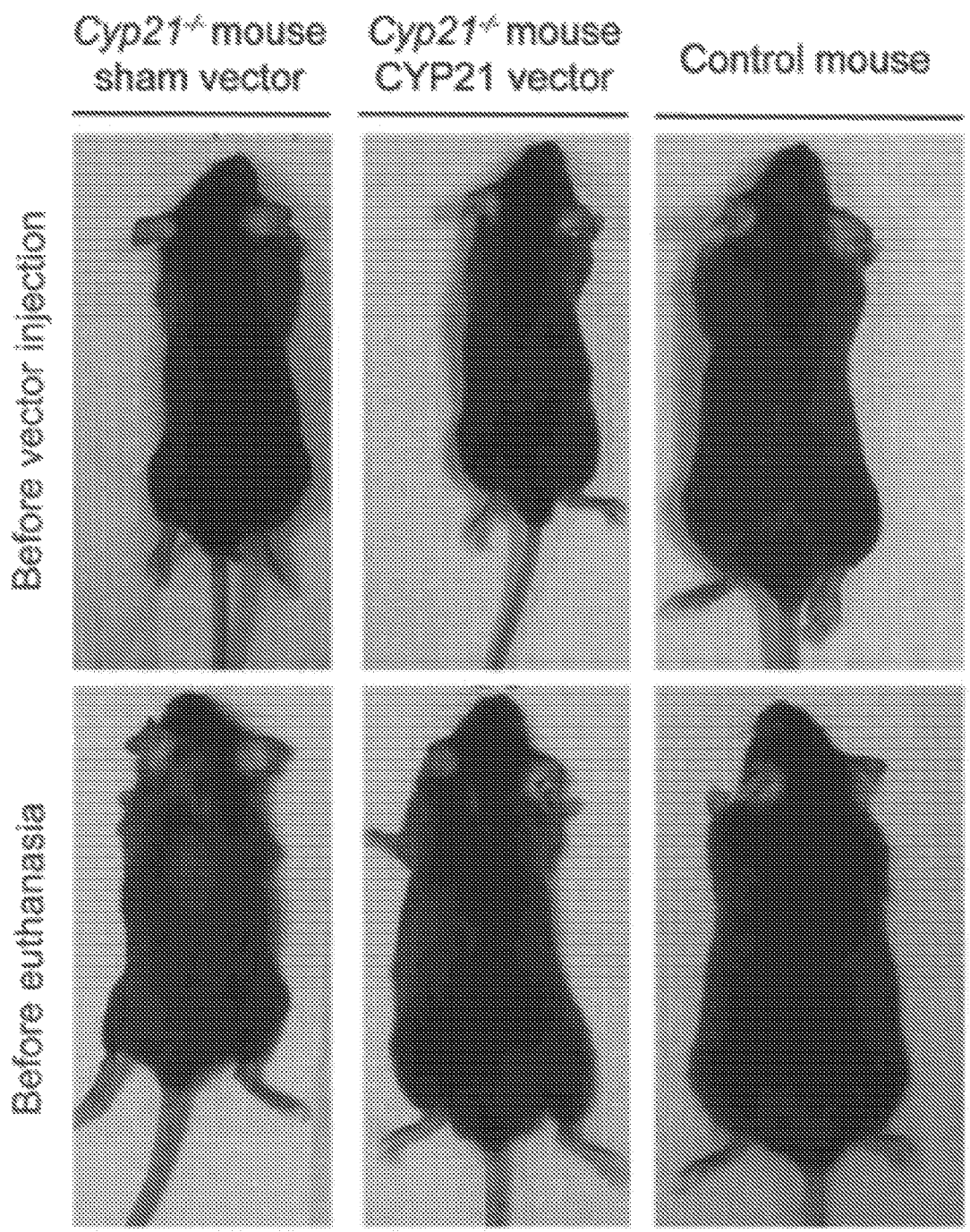

The invention relates to recombinant adeno-associated virus (AAV) vectors that are engineered to express 21-hydroxylase (21OH) and can be used to treat 21-hydroxylase deficiency (21OHD). In some aspects, the invention provides a recombinant adeno-associated virus (rAAV) vector comprising a non-AAV nucleotide sequence encoding a 21OH protein, an rAAV particle comprising such a vector and methods of using such vectors and particles to treat 21OHD in subjects in need thereof.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. The term "about", when immediately preceding a number or numeral, means that the number or numeral ranges plus or minus 10%. It should be understood that the terms "a" and "an" as used herein refer to "one or more" of the enumerated components unless otherwise indicated. The use of the alternative (e.g., "or") should be understood to mean either one, both, or any combination thereof of the alternatives. The term "and/or" should be understood to mean either one, or both of the alternatives. As used herein, the terms "include" and "comprise" are used synonymously.

Recombinant AAV Vectors and Particles

In one aspect, the invention provides a viral vector for delivery of a 21-hydroxylase (21OH) nucleic acid sequence to cells in need of treatment. Thus, in one embodiment, the invention relates to a recombinant adeno-associated virus (rAAV) vector comprising a nucleic acid molecule comprising at least one AAV inverted terminal repeat (ITR) and a non-AAV nucleotide sequence (also referred to as a heterologous polynucleotide) encoding a 21OH protein, the non-AAV nucleotide sequence operably linked to a promoter. As used herein, the term "operable linkage" or "operably linked" refers to a physical or functional juxtaposition of the components so described as to permit them to function in their intended manner. In the example of an expression control element (such as a promoter or enhancer) in operable linkage with a polynucleotide, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence. "Operably linked" may mean that the nucleic acid sequences being linked are contiguous, or substantially contiguous, and, where necessary to join two protein coding regions, contiguous and in reading frame.

In some embodiments, a rAAV vector expresses a 21OH protein that is a human 21OH protein. The CYP21A2 gene encodes 21OH protein. As used herein, 21OH may refer to the 21OH protein or nucleic acid sequence encoding said protein. In some cases, the 21OH protein expressed by a rAAV vector described herein is a native (e.g., wild-type) 21OH protein. The 21OH protein or polypeptide encoded by the nucleotide sequence includes full-length native sequences, as with a naturally occurring 21OH protein, as well as functional subsequences, modified forms or sequence variants so long as the subsequence, modified form or variant retains some degree of functionality of the native full-length 21OH protein. In methods and uses of the invention, 21OH proteins and polypeptides encoded by the nucleotide sequences in a rAAV vector can be, but are not required to be, identical to the endogenous 21OH protein that is defective, or whose expression is insufficient, or deficient in the treated subject.

In some embodiments, the non-AAV nucleotide sequence (e.g., heterologous sequence) encoding a 21OH protein is the wild-type CYP21 gene sequence. In some embodiments, the non-AAV nucleotide sequence (e.g., heterologous sequence) encoding a 21OH protein has been codon-optimized with respect to the wild-type CYP21 gene sequence. In some embodiments, a 21OH-encoding nucleotide sequence of the invention is a codon-optimized sequence and comprises or consists of SEQ ID NO:50.

Codon optimization takes advantage of redundancies in the genetic code to enable a nucleotide sequence to be altered while maintaining the same amino acid sequence of the encoded protein. In some embodiments, codon optimization is carried out to facilitate an increase or decrease in the expression of an encoded protein. This is effected by tailoring codon usage in a nucleotide sequence to that of a specific cell type, thus taking advantage of cellular codon bias corresponding to a bias in the relative abundance of particular tRNAs in the cell type. By altering the codons in the nucleotide sequence so that they are tailored to match the relative abundance of corresponding tRNAs, it is possible to increase expression. Conversely, it is possible to decrease expression by selecting codons for which the corresponding tRNAs are known to be rare in the particular cell type.

In some embodiments, a codon-optimized nucleotide sequence encoding a 21OH protein is more stable than the wild-type cDNA sequence, thereby avoiding generating alternatively spliced variants or truncated proteins if the non-AAV nucleotide sequence is introduced into the transcriptional machinery through gene therapy.

In some embodiments, the non-AAV nucleotide sequence (e.g., heterologous sequence) encoding a 21OH protein encodes the amino acid sequence of SEQ ID NO:1 (see Table 10). In other embodiments, the non-AAV nucleotide sequence encoding a 21OH protein encodes an amino acid sequence at least 90%, at least 91%, at least 92%, at least 93%, at least 94%, at least 95%, at least 96%, at least 97%, at least 98% or at least 99% identical to SEQ ID NO:1. In some embodiments, the non-AAV nucleotide sequence (e.g., heterologous sequence) encoding a 21OH protein is the human 21OH cDNA, optionally linked to a nucleotide sequence encoding a hemagglutinin (HA) tag. In certain cases, the non-AAV nucleotide sequence (e.g., heterologous sequence) encoding a 21OH protein is linked to a nucleotide sequence encoding a tag, for example hemagglutinin (HA), UA, cMyc, or any suitable tag. "CYPHA" may refer to a 21OH transgene fused to a sequence encoding an HA tag.

The terms "identity," "homology" and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions they share identity within that region. An "aligned" sequence refers to multiple polynucleotide or protein (amino acid) sequences, often containing corrections for missing or additional bases or amino acids (gaps) as compared to a reference sequence.

The identity can extend over the entire sequence length or a portion of the sequence. In particular aspects, the length of the sequence sharing the percent identity is 2, 3, 4, 5 or more contiguous polynucleotide or amino acids, e.g., 6, 7, 8, 9, 10, 11, 12, 13, 14, 15, 16, 17, 18, 19, 20, etc. contiguous amino acids. In additional particular aspects, the length of the sequence sharing identity is 20 or more contiguous polynucleotide or amino acids, e.g., 20, 21, 22, 23, 24, 25, 26, 27, 28, 29, 30, 31, 32, 33, 34, 35, etc. contiguous amino acids. In further particular aspects, the length of the sequence sharing identity is 35 or more contiguous polynucleotide or amino acids, e.g., 35, 36, 37, 38, 39, 40, 41, 42, 43, 44, 45, 46, 47, 48, 49, 50, etc., contiguous amino acids. In yet further particular aspects, the length of the sequence sharing identity is 50 or more contiguous polynucleotide or amino acids, e.g., 50-55, 55-60, 60-65, 65-70, 70-75, 75-80, 80-85, 85-90, 90-95, 95-100, 100-110, etc. contiguous polynucleotide or amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology.

The extent of identity (homology) between two sequences can be ascertained using a computer program and mathematical algorithm. Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Vector genome sequences, including rAAV vector genome sequences described herein, can include one or more "expression control elements". Typically, expression control elements are nucleic acid sequences that influence expression of an operably linked polynucleotide. Control elements, including expression control elements as set forth herein, such as promoters and enhancers, present within a vector are included to facilitate proper heterologous polynucleotide (e.g., 21OH gene) transcription and/or translation (e.g., a promoter, enhancer, splicing signal for introns, maintenance of the correct reading frame of the gene to permit in-frame translation of mRNA, etc.). Expression control elements include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product (e.g., 21OH). In some embodiments, a rAAV vector genome sequence of the invention comprises a Kozak sequence (for example, a DNA sequence transcribed to an RNA Kozak sequence). In some embodiments, a rAAV vector genome sequence of the invention comprises a Kozak sequence upstream of the nucleotide sequence encoding a 21OH protein. In some embodiments, an RNA Kozak sequence comprises or consists of ACCAUGG (SEQ ID NO:44), GCCGCCAC-CAUGG (SEQ ID NO:45), CCACCAUG (SEQ ID NO:46) or CCACCAUGG (SEQ ID NO:47).

Expression control can be carried out at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the nucleotide sequence expressing 21OH), even at considerable distances. Nevertheless, owing to the polynucleotide length limitations, for AAV vectors, such expression control elements will typically be within 1 to 1000 nucleotides from the nucleotide sequence encoding 21OH.

Functionally, expression of an operably linked nucleotide sequence encoding 21OH is at least in part controllable by the element (e.g., promoter) such that the element modulates transcription of the nucleotide sequence and, as appropriate, translation of the transcript. A specific example of an expression control element is a promoter, which is usually located 5' of the transcribed sequence. Another example of an expression control element is an enhancer, which can be located 5' of the transcribed sequence, 3' of the transcribed sequence, or within the transcribed sequence.

A "promoter" as used herein can refer to a nucleic acid sequence that is located adjacent to a nucleic acid sequence (e.g., heterologous polynucleotide) that encodes a recombinant product (e.g., 21OH). A promoter is typically operatively linked to an adjacent sequence, e.g., heterologous polynucleotide. A promoter typically increases an amount expressed from a heterologous polynucleotide as compared to an amount expressed when no promoter exists.

An "enhancer" as used herein can refer to a sequence that is located adjacent to a nucleotide sequence encoding 21OH. Enhancer elements are typically located upstream of a promoter element but also function and can be located downstream of or within a DNA sequence (e.g., a nucleotide sequence encoding 21OH). Hence, an enhancer element can be located 100 base pairs, 200 base pairs, or 300 or more base pairs upstream or downstream of a heterologous polynucleotide. Enhancer elements typically increase expression of a heterologous polynucleotide above the level of increased expression afforded by a promoter element.

In some embodiments, expression control elements include ubiquitous, constitutive or promiscuous promoters and/or enhancers which are capable of driving expression of a polynucleotide in many different cell types. Such elements include, but are not limited to, a cytomegalovirus/β-actin hybrid (e.g., CAG, CB6 or CBA) promoter, a phosphoglycerol kinase (PGK) promoter, cytomegalovirus (CMV) immediate early promoter and/or enhancer sequences, the Rous sarcoma virus (RSV) promoter and/or enhancer sequences and other viral promoters and/or enhancers active in a variety of mammalian cell types, or synthetic elements that are not present in nature (see, e.g., Boshart et al, *Cell,* 41:521-530 (1985)), the SV40 promoter, the dihydrofolate reductase promoter, the chicken β-actin (CBA) promoter, the EF 1 promoter (Invitrogen), the immediate early CMV enhancer coupled with the CBA promoter (Beltran et al., *Gene Therapy,* 17(9): 1162-1174 (2010)), and the CBh promoter (Gray et al., *Hum Gene Ther,* 22(9): 1143-1153 (2011)). In certain aspects, a rAAV of the invention comprises a synthetic CASI promoter which contains a portion of the CMV enhancer, a portion of the chicken beta-actin promoter, and a portion of the UBC enhancer. See, e.g., WO 2012/115980. In some embodiments, a rAAV vector comprises a CAG promoter sequence comprising SEQ ID NO:2 or a nucleotide sequence at least 90%, at least 91%, at least 92%, at least 93%, at least 94%, at least 95%, at least 96%, at least 97%, at least 98% or at least 99% identical to SEQ ID NO:2. In some embodiments, a rAAV vector comprises a PGK promoter sequence comprising SEQ ID NO:3 or a nucleotide sequence at least 90%, at least 91%, at least 92%, at least 93%, at least 94%, at least 95%, at least 96%, at least 97%, at least 98% or at least 99% identical to SEQ ID NO:3. In some embodiments, a rAAV vector comprises a CB6 promoter sequence comprising SEQ ID NO:48 or a nucleotide sequence at least 90%, at least 91%, at least 92%, at least 93%, at least 94%, at least 95%, at least 96%, at least 97%, at least 98% or at least 99% identical to SEQ ID NO:48. In some embodiments, a rAAV vector comprises a CBA promoter sequence comprising SEQ ID NO:49 or a nucleotide sequence at least 90%, at least 91%, at least 92%, at least 93%, at least 94%, at least 95%, at least 96%, at least 97%, at least 98% or at least 99% identical to SEQ ID NO:49. See Table 10 for non-limiting examples of promoter sequences.

Inducible promoters allow regulation of gene expression and can be regulated by exogenously supplied compounds, environmental factors such as temperature, or the presence of a specific physiological state, acute phase, a particular differentiation state of the cell, or in replicating cells only. Inducible promoters and inducible systems are available from a variety of commercial sources, including, without limitation, Invitrogen and Clontech. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Any type of inducible promoter which is tightly regulated and is specific for the particular target cell type in which 21OH expression is desired may be used.

Expression control elements (e.g., promoters) include those active in a particular tissue or cell type, referred to herein as "tissue-specific expression control elements/promoters." Tissue-specific expression control elements are typically active in specific cell or tissue (e.g., adrenal gland, adrenal cortex, liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type. Thus, in some cases, a rAAV vector of the invention comprises a promoter that directs expression of the nucleotide sequence encoding 21OH protein in a host cell (e.g., an adrenal gland cell). In certain embodiments, an adrenal gland cell is an adrenal cortex cell. In some embodiments, a rAAV vector of the invention comprises a non-AAV nucleotide sequence encoding a 21OH protein, the non-AAV nucleotide sequence operably linked to a promoter specific for expression in an adrenal cortex cell or an adrenal medulla cell. In some embodiments, a rAAV vector of the invention comprises a non-AAV nucleotide sequence encoding a 21OH protein, the non-AAV nucleotide sequence operably linked to a promoter specific for expression in a subject's adrenal gland (e.g., adrenal cortex or adrenal medulla), liver or ovary. In certain embodiments, a rAAV vector of the invention comprises a non-AAV nucleotide sequence encoding a 21OH protein, the non-AAV nucleotide sequence operably linked to a promoter specific for expression in an adrenal stem cell (e.g., an adrenocortical stem cell) or an adrenal progenitor cell.

The regulatory sequences useful in the rAAV vectors of the present invention may also contain an intron, desirably located between the promoter/enhancer sequence and the 21OH gene. One desirable intron sequence is derived from SV-40, and is a 100 bp mini-intron splice donor/splice acceptor referred to as SD-SA. In one aspect, a rAAV vector comprises a posttranscriptional regulatory element. One example of a posttranscriptional regulatory element is the woodchuck hepatitis virus post-transcriptional element (WPRE). (See, e.g., Wang and Verma, *Proc. Natl. Acad. Sci., USA*, 96: 3906-3910 (1999)). In certain embodiments, a posttranscriptional regulatory element is a hepatitis B virus posttranscriptional regulatory element (HBVPRE) or a RNA transport element (RTE). In some embodiments, the WPRE or HBVPRE sequence is any of the WPRE or HBVPRE sequences disclosed in U.S. Pat. No. 6,136,597 or U.S. Pat. No. 6,287,814. In some embodiments, a WPRE sequence comprises or consists of:

```
                                              (SEQ ID NO: 51)
aatcaacctc tggattacaa aatttgtgaa agattgactg atattcttaa ctatgttgct ccttttacgc tgtgtggata tgctgcttta atgcctctgt atcatgctat tgcttcccgt acggctttcg ttttctcctc cttgtataaa tcctggttgc tgtctcttta tgaggagttg tggcccgttg tccgtcaacg tggcgtggtg tgctctgtgt ttgctgacgc aaccccact ggctggggca ttgccaccac ctgtcaacte cttctggga ctttcgcttt cccctcccg atcgccacgg cagaactcat cgccgcctgc cttgcccgct gctggacagg ggctaggttg ctgggcactg ataattccgt ggtgttgtcg gggaagctga cgtcctttcc atggctgctc gcctgtgttg ccaactggat cctgcgcggg acgtccttct gctacgtccc ttcggctctc aatccagcgg acctccctte ccgaggcctt ctgccggttc tgcggcctct cccgcgtctt cgctttcggc ctccgacgag tcggatctcc ctttgggccg cctccccgcc tg.
```

In some embodiments, a rAAV vector comprises a polyA signal. PolyA signals may be derived from many suitable species, including, without limitation SV-40, human and bovine.

Another useful regulatory component that may be included in a rAAV vector is an internal ribosome entry site (IRES). An IRES sequence, or other suitable systems, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence. The IRES may be located 5' or 3' to the 21OH transgene in the rAAV vector. In other embodiments, a rAAV vector may comprise a nucleotide sequence encoding a 2A peptide that allows for expression of multiple polypeptides from a single promoter.

A recombinant "vector" or "rAAV vector" is derived from the wild type genome of a virus such as AAV by using molecular methods to remove the wild type genome from the virus, and replace it with a non-native nucleic acid, such as a heterologous polynucleotide sequence (e.g., a therapeutic gene expression cassette expressing 21OH). Typically, for AAV, one or both inverted terminal repeat (ITR) sequences of the wild-type AAV genome are retained in the AAV vector. A rAAV vector can be distinguished from a viral genome, because all (or a part) of the viral genome has been replaced with a non-native sequence with respect to the viral genomic nucleic acid. Incorporation of a non-native sequence such as a heterologous polynucleotide therefore defines the viral vector as a "recombinant" vector, which in the case of AAV can be referred to as a "rAAV vector". A rAAV vector comprising a nucleic acid molecule encoding 21OH may also be referred to as a "CYP21 vector" or a "21OH vector". As will be apparent from context, "vector" may refer to an isolated recombinant nucleotide sequence or an AAV particle or virion comprising a recombinant nucleotide sequence.

In some embodiments, a rAAV vector does not comprise any binding sites for miRNA (microRNA). In some embodiments, a rAAV vector comprises one, two, three, four, five or more binding sites for an miRNA that is expressed in cells where expression of the 21OH protein is not desired (i.e., detargeting). In some embodiments, a rAAV vector comprises one or more binding sites for miR-122. Binding of miR-122 to the 21OH-encoding sequence may reduce expression of this sequence in liver cells, where miR-122 is highly prevalent (Thakral and Ghoshal, Curr Gene Ther. 2015; 15(2): 142-150).

A rAAV nucleic acid sequence can be packaged into a virus (also referred to herein as a "particle" or "virion") for subsequent infection (transformation) of a cell, ex vivo, in vitro or in vivo. Where a recombinant vector sequence is encapsidated or packaged into an AAV particle, the particle can be referred to as a "rAAV". Such particles or virions will typically include proteins that encapsidate or package the vector genome. Particular examples include viral envelope proteins, and, in the case of AAV, capsid proteins.

The AAV components of the rAAV vectors and particles described herein may be selected from various AAV serotypes. In certain cases, a rAAV vector may comprise an AAV nucleic acid sequence from a rh10, AAV1, AAV2, AAV3, AAV4, AAV5, AAV6, AAV7, AAV8, AAV9, AAV10, AAV11, AAV12 or rh74 serotype. These AAV components may be readily isolated using techniques available to those of skill in the art from an AAV serotype. Such AAV may be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank™, PubMed, or the like.

In certain embodiments, a rAAV vector or rAAV particle comprises an AAV nucleic acid sequence or AAV protein as disclosed in U.S. Pat. No. 7,906,111 or U.S. Pat. No. 7,629,322, incorporated herein by reference in their entirety. In some embodiments, a rAAV vector or rAAV particle comprises an AAV nucleic acid sequence or AAV protein from AAV serotype AAV8 or its variants, as disclosed in U.S. Pat. Nos. 7,282,199, 9,587,250 or U.S. Pat. No. 9,677,089, incorporated herein by reference in their entirety. In some embodiments, a rAAV vector or rAAV particle comprises an AAV nucleic acid sequence or AAV protein from AAV serotype AAV9 or its variants, as disclosed in U.S. Pat. No. 7,198,951, incorporated herein by reference in its entirety. In some embodiments, a rAAV vector or rAAV particle comprises an AAV nucleic acid sequence or AAV protein from AAV serotype rh74 or its variants, as disclosed in U.S. Pat. No. 9,840,719, incorporated herein by reference in its entirety.

In some aspects, a rAAV vector of the invention comprises a nucleic acid molecule comprising at least one AAV ITR sequence. In certain embodiments, a rAAV vector comprises two ITR sequences. In certain cases, AAV ITRs may be selected from among any AAV serotype, including, without limitation, rh10, AAV1, AAV2, AAV3, AAV4, AAV5, AAV6, AAV7, AAV8, AAV9, AAV10, AAV11, AAV12, rh74 or other AAV serotypes. In some embodiments, a rAAV vector described herein comprises a genome comprising a sequence of one or two AAV2 ITRs.

The invention further provides a rAAV particle comprising a rAAV vector described herein. Thus, in some aspects, the invention relates to a rAAV particle comprising a nucleic acid molecule comprising at least one AAV ITR and a non-AAV nucleotide sequence (also referred to as a heterologous polynucleotide) encoding a 21OH protein, the non-AAV nucleotide sequence operably linked to a promoter. In some embodiments, a rAAV particle comprises at least one capsid protein from AAV serotype rh10, AAV1, AAV2, AAV3, AAV4, AAV5, AAV6, AAV7, AAV8, AAV9, AAV10, AAV11, AAV12 or rh74 or other AAV serotypes.

In one embodiment, a rAAV vector is an rh10 AAV vector comprising human 21OH cDNA, an ITR from AAV2, and a CAG promoter consisting of the enhancer from the cytomegalovirus immediate-early gene, the promoter, splice donor and intron from the chicken β-actin gene, and the splice acceptor from the rabbit β-globin gene. In a further embodiment, a rAAV vector comprises a nucleic acid sequence encoding a 21OH protein comprising SEQ ID NO:1 and a CAG promoter comprising or consisting of SEQ ID NO:2. In one embodiment, a rAAV vector is an rh10 AAV vector comprising human 21OH cDNA, an ITR from AAV2, and a PGK promoter. In another embodiment, a rAAV vector comprises a nucleic acid sequence encoding a 21OH protein comprising SEQ ID NO: 1 and a PGK promoter comprising or consisting of SEQ ID NO:3.

In some embodiments, a rAAV vector or particle comprises AAV1 capsid and a nucleic acid molecule comprising human 21OH cDNA, a CAG, PGK, CBA or CB6 promoter and, optionally, one or two AAV2 ITR sequences. In one embodiment, a rAAV vector or particle is the ssAAV1-PGK-CYP21HA vector described in Example 9. In some embodiments, a rAAV vector or particle is an AAV1-CAG-CYP21, AAV1-PGK-CYP21, AAV1-CBA-CYP21 or AAV1-CB6-CYP21 vector. In other embodiments, a rAAV vector or particle comprises AAV5 capsid and a nucleic acid molecule comprising human 21OH cDNA, a CAG, PGK, CBA or CB6 promoter and, optionally, one or two AAV2 ITR sequences. In one embodiment, a rAAV vector or particle is the ssAAV5-PGK-CYP21HA vector described in Example 7. In some embodiments, a rAAV vector or particle is an AAV5-CAG-CYP21, AAV5-PGK-CYP21, AAV5-CBA-CYP21 or AAV5-CB6-CYP21 vector. In yet other embodiments, a rAAV vector or particle is an AAV6 vector comprising human 21OH cDNA, a CAG, PGK, CBA or CB6 promoter and, optionally, one or two AAV2 ITR sequences. In some embodiments, a rAAV vector or particle is an AAV6-CAG-CYP21, AAV6-PGK-CYP21, AAV6-CBA-CYP21 or AAV6-CB6-CYP21 virus. In further embodiments, a rAAV vector or particle comprises AAV8 capsid and a nucleic acid molecule comprising human 21OH cDNA, a CAG, PGK, CBA or CB6 promoter and, optionally, one or two AAV2 ITR sequences. In some embodiments, a rAAV vector or particle is an AAV8-CAG-CYP21, AAV8-PGK-CYP21, AAV8-CBA-CYP21 or AAV8-CB6-CYP21 virus. In some embodiments, a rAAV vector or particle is an AAV9 vector comprising human 21OH cDNA, a CAG, PGK, CBA or CB6 promoter and, optionally, one or two AAV2 ITR sequences. In some embodiments, a rAAV vector or particle is an AAV9-CAG-CYP21, AAV9-PGK-CYP21, AAV9-CBA-CYP21 or AAV9-CB6-CYP21 vector. In additional embodiments, a rAAV vector or particle comprises AAV10 capsid and a nucleic acid molecule comprising human 21OH cDNA, a CAG, PGK, CBA or CB6 promoter and, optionally, one or two AAV2 ITR sequences. In some embodiments, a rAAV vector or particle is an AAV10-CAG-CYP21, AAV10-PGK-CYP21, AAV10-CBA-CYP21 or AAV10-CB6-CYP21 virus. In some embodiments, a rAAV vector or particle comprises rh10 AAV capsid and a nucleic acid molecule comprising human 21OH cDNA, a CAG, PGK, CBA or CB6 promoter and, optionally, one or two AAV2 ITR sequences. In one embodiment, a rAAV vector or particle is the AAVrh10-CAG-CYP21A2-HA virus described in Example 1. In some embodiments, a rAAV vector or particle is an AAVrh10-CAG-CYP21, AAVrh10-PGK-CYP21, AAVrh10-CBA-CYP21 or AAVrh10-CB6-CYP21 vector. In any of these embodiments, a promoter may comprise or consist of SEQ ID NO:2, 3, 48 or 49 or a nucleotide sequence at least 90%, at least 91%, at least 92%, at least 93%, at least 94%, at least 95%, at least 96%, at least 97%, at least 98% or at least 99% identical to SEQ ID NO:2, 3, 48 or 49. In any of these embodiments, a rAAV vector may comprise a Kozak sequence. In some embodiments, a Kozak sequence may comprise or be transcribed to SEQ ID NO:44, SEQ ID NO:45, SEQ ID NO:46 or SEQ ID NO:47. In any of these embodiments, a rAAV vector may further comprise an HBVPRE sequence or a WPRE sequence (e.g., SEQ ID NO:51).

In some embodiments, a rAAV vector or particle is an AAV5 serotype vector or particle comprising a codon-optimized nucleotide sequence encoding human 21OH under the control of a CBA promoter, comprising a Kozak sequence and further with or without an miR-122 binding sequence. In one embodiment, a rAAV vector or particle is the AAV5-CBA-Kozak-COhCYP21-miR122 vector described in Example 13. In some embodiments, a rAAV vector or particle is an AAV5-CBA-Kozak-hCYP21, AAV5-CBA-Kozak-hCYP21-miR122 or AAV5-CBA-Kozak-COhCYP21 vector. In any of these embodiments, the codon-optimized nucleotide sequence may comprise SEQ ID NO:50 and the Kozak sequences may comprise or be transcribed to SEQ ID NO:44, SEQ ID NO:45, SEQ ID NO:46 or SEQ ID NO:47. In any of these embodiments, a rAAV vector may further comprise an HBVPRE sequence or a WPRE sequence (e.g., SEQ ID NO:51).

A rAAV vector or rAAV particle may comprise the cap proteins, including the vp1, vp2, vp3 and hypervariable regions, the rep proteins, including rep 78, rep 68, rep 52, and rep 40, and the sequences encoding these proteins. These AAV components may be readily utilized in a variety of vector systems and host cells. Such components may be used alone, in combination with other AAV serotype sequences or components, or in combination with elements from non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from anon-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, the AAV is AAV2/5. In another embodiment, the AAV is AAV2/8. See, e.g., Mussolino et al., *Gene Therapy*, 18(7): 637-645 (2011); Rabinowitz et al., *J Virol*, 76(2): 791-801 (2002).

In some embodiments, vectors useful in compositions and methods described herein contain, at a minimum, sequences encoding a selected AAV serotype capsid, or a fragment thereof. In some embodiments, useful vectors contain, at a minimum, sequences encoding a selected AAV serotype rep protein, or a fragment thereof. Optionally, such vectors may contain both AAV cap and rep proteins. In vectors in which both AAV rep and cap are provided, the AAV rep and AAV cap sequences can both be of one serotype. Alternatively, vectors may be used in which the rep sequences are from one AAV serotype and the cap sequences are from a different AAV serotype. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, incorporated herein by reference in its entirety.

A suitable rAAV can be generated by culturing a host cell which contains a nucleic acid sequence encoding an AAV serotype capsid protein, or fragment thereof, as defined herein; a functional rep gene; a nucleic acid molecule composed of, at a minimum, AAV inverted terminal repeats (ITRs) and a 21OH (CYP21A2) nucleic acid sequence; and sufficient helper functions to permit packaging of the nucleic acid molecule into the AAV capsid protein. In some aspects, the invention provides a host cell comprising a rAAV vector or a rAAV particle disclosed herein. The components required to be present in the host cell to package a rAAV vector in an AAV capsid may be provided to the host cell in trans. Alternatively, any one or more of the required components (e.g., vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion above of regulatory elements suitable for use with a non-AAV nucleotide sequence, i.e., 21OH. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The rAAV vector, rep sequences, cap sequences, and helper functions required for producing the rAAV of the invention may be delivered to the packaging host cell in the form of any genetic element which transfers the sequences carried thereon. The selected genetic element may be delivered by any suitable method, including those described herein. The methods used to construct any embodiment of this invention are known to those with skill in nucleic acid manipulation and include genetic engineering, recombinant engineering and synthetic techniques. See, e.g., Sambrook et al, Molecular Cloning: A Laboratory Manual, Cold Spring Harbor Press, Cold Spring Harbor, N.Y. Similarly, methods of generating rAAV particles are well known. See, e.g., Fisher et al, *J. Virol.*, 70:520-532 (1993) and U.S. Pat. No. 5,478,745, incorporated herein by reference in their entirety.

In one aspect, the invention provides a method of producing an rAAV particle, the method comprising culturing a host cell containing: (a) a nucleic acid molecule comprising or consisting of a rAAV vector genome expressing 21OH as described herein; (b) a nucleic acid molecule encoding an AAV rep; (c) a nucleic acid molecule encoding at least one AAV capsid protein and (d) sufficient helper functions for packaging the rAAV vector genome into the rAAV particle.

rAAV particles of the invention may be purified by any method known in the art. In one embodiment, a rAAV virus may be purified by anion exchange chromatography. See, e.g., US 2018/0163183 A1.

Uses of Recombinant AAV Vectors and Particles

The invention encompasses methods and uses of the rAAV comprising a nucleic acid molecule encoding 21OH as described herein for providing a therapeutic benefit to a subject with a disorder or a disease characterized by a deficiency or malfunction of 21OH. In some aspects, a method comprises administering to a subject in need a therapeutically effective amount of a rAAV described herein, thereby treating said disorder or said disease characterized by a deficiency or malfunction of 21OH in the subject.

In some cases, the invention provides a method of expressing 21OH in a subject in need thereof, comprising administering to the subject a therapeutically effective amount of a rAAV particle described herein or pharmaceutical composition comprising said particle, thereby expressing 21OH in the subject. In certain embodiments, the invention provides a method of increasing the expression of 21OH in a subject in need thereof, comprising administering to the subject a therapeutically effective amount of a rAAV particle described herein or pharmaceutical composition comprising said particle, thereby increasing expression of 21OH in the subject. In some embodiments, a rAAV described herein causes expression of 21OH or increases the expression of 21OH in the subject's adrenal gland (e.g., adrenal cortex or adrenal medulla), liver or ovary. In certain embodiments, a rAAV described herein causes expression of 21OH or increases the expression of 21OH in the subject's adrenal stem cells (e.g., adrenocortical stem cells) or adrenal progenitor cells.

The invention contemplates a method of treating a subject with 21-hydroxylase deficiency (21OHD), comprising administering to the subject a therapeutically effective amount of a rAAV particle described herein or pharmaceutical composition comprising said particle, thereby treating 21OHD in the subject. A treatment method may further comprise selecting a subject with 21OHD before the administering step. In some embodiments, a subject may be screened and identified or diagnosed as having 21OHD (e.g., by genetic or physiological testing) even though the subject does not have one or more symptoms of the disease. In other embodiments, a subject has one or more symptoms of 21OHD. In certain embodiments, a subject has a mutation in a CYP21A2 gene. In one embodiment, a subject has a loss-of-function mutation in a CYP21A2 gene. In certain embodiments, a subject has a defect in a CYP21A2 gene caused by gene conversion or recombination between the functional CYP21A2 gene and the closely linked, non-functional CYP21A1P pseudogene.

In some embodiments, the invention provides a method of treating, reducing, improving, slowing the progression of or preventing a symptom of 21OHD (or congenital adrenal hyperplasia, CAH) in a subject having 21OHD (or CAH), the method comprising administering to the subject a therapeutically effective amount of a rAAV particle described herein or pharmaceutical composition comprising said particle, thereby treating, reducing, improving, slowing the progression of or preventing a symptom of 21OHD in a subject. Non-limiting examples of symptoms of 21OHD (or CAH) include genital and muscle mass virilization, salt wasting and dehydration in infancy, impaired sexuality (classical forms) and hirsutism, acne, and decreased fertility (classical and non-classical forms). In a male patient, non-limiting examples of symptoms of 21OHD (or CAH) include short stature and premature virilization. The Prader classification system is used to measure the degree of virilization of the genitalia of the human body. In some embodiment, a subject treated by the methods of the invention is affected with the Prader stage IV or V form of 21OHD (or CAH).

In any of the treatment methods described herein, a rAAV particle comprising a nucleic acid molecule encoding 21OH or a pharmaceutical composition comprising said particle may be administered to a subject by any means of introducing said rAAV particle into the adrenal cortex vasculature or the adrenal cortex itself. In some embodiments, a rAAV particle comprising a nucleic acid molecule encoding 21OH or a pharmaceutical composition comprising said particle may be administered to a subject intravenously; by direct injection into the adrenal gland via open surgery or laparoscopy; by injection into an adrenal artery via catheterization. In some embodiments, the direct injection into the adrenal gland is direct injection into the adrenal cortex.

In certain aspects, a rAAV particle comprising a nucleic acid molecule encoding 21OH as described herein or a pharmaceutical composition comprising said particle may be used to treat a subject suffering from congenital adrenal hyperplasia (CAH). Deficiency of 21OH often leads to CAH, a family of inherited disorders affecting the adrenal glands. CAH may be present in a subject in a severe or a mild form. The severe form, called classical CAH, is usually detected in the newborn period or in early childhood. The milder form, called non-classical CAH (NCAH or NCCAH) or late-onset CAH, may cause symptoms at any time from infancy through adulthood (see, e.g., Kurtoglu et al., *J Clin Res Pediatr Endocrinol*, 9(1): 1-7 (2017)). The rAAV of the invention may be used to treat a subject with classical CAH or non-classical CAH. Subjects with classical CAH may experience fetal masculinization of external genitals, low or absent glucocorticoid and mineralocorticoid production and produce a large excess of androgens. Subjects with non-classical CAH may experience increased production of androgens without fetal masculinization and without cortisol and aldosterone deficits.

Cortisol is a steroid produced by the adrenal glands. Cortisol is used in the body to respond to physical and emotional stress, and maintain adequate energy supply and blood sugar levels. The adrenal glands are controlled by the pituitary gland, a small pea-sized gland at the base of the brain. In healthy individuals, the pituitary gland releases adrenocorticotropic hormone (ACTH) when there is insufficient cortisol present in the bloodstream. ACTH stimulates the adrenals to produce more cortisol. However, those with CAH have insufficient amounts of 21OH, which is needed to convert the precursor 17-hydroxyprogesterone (17-OHP) into cortisol. As a result, the pituitary gland continues to sense the need for cortisol and releases more ACTH. This leads to an overabundance of 17-OHP, which is then converted in the adrenals into excess androgens (masculinizing steroid hormones). As such, a subject may be diagnosed with CAH by determining increased circulating levels of the affected steroid hormones. Neonatal screening for 21OHD is typically accomplished using a 17-OHP measurement. Additionally, a subject with CAH may be monitored by tracking circulating levels of 17-OHP. Thus, in some embodiments, the circulating levels of the affected steroid hormones may be measured in a subject with CAH before, during and/or after treatment with a rAAV particle comprising a nucleic acid molecule encoding 21OH as described herein or a pharmaceutical composition comprising said particle. The circulating levels of 17-OHP in a subject may be used for diagnosis of a subject and to inform a decision about whether to begin or to continue treatment of the subject with a rAAV particle or pharmaceutical composition described herein.

In certain embodiments, a subject may be a human, a non-human primate, a pig, a horse, a cow, a dog, a cat, a rabbit, a guinea pig, a hamster, a mouse or a rat. A subject may be a human female or a human male. In some embodiments, a subject is a human infant. In certain cases, a subject is a human infant about 1 month old, about 2 months old, about 3 months old, about 4 months old, about 5 months old, about 6 months old, about 7 months old, about 8 months old, about 9 months old, about 10 months old, about 11 months old or about 1 year old. In some embodiments, a subject may be a human infant less than 3 months old, less than 6 months old, less than 9 months old, less than 1 year old or less than 18 months old.

As used herein, the term "patient in need" or "subject in need" refers to a patient or subject at risk of, or suffering from, a disease, disorder or condition that is amenable to treatment or amelioration with a rAAV comprising a nucleic acid sequence encoding 21OH or a composition comprising such a rAAV provided herein. A patient or subject in need may, for instance, be a patient or subject diagnosed with a disease associated with the malfunction of 21OH, such as 21OHD. A subject may have a mutation or a malfunction in a 21OH gene or protein. "Subject" and "patient" are used interchangeably herein.

As used herein, the term "effective amount" or "therapeutically effective amount" refers to the amount of a pharmaceutical agent, e.g., a rAAV, which is sufficient to reduce or ameliorate the severity and/or duration of a disorder, e.g., 21OHD, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of a rAAV may, for example, increase the expression of 21OH, and/or relieve to some extent one or more of the symptoms associated with 21OHD.

The invention further contemplates a use of a pharmaceutical agent (e.g., a rAAV or a pharmaceutical composition comprising a rAAV) described herein in the manufacture of a medicament for treating a disorder or a disease characterized by a malfunction or a deficiency of 21OH in a subject. The invention also includes a use of a pharmaceutical agent (e.g., a rAAV or a pharmaceutical composition comprising a rAAV) described herein for treating a disorder or a disease characterized by a malfunction or a deficiency of 21OH in a subject.

Pharmaceutical Compositions and Routes of Administration

The rAAV vectors or particles of the invention can be incorporated into pharmaceutical compositions suitable for administration. In one aspect, the invention provides a pharmaceutical composition comprising a rAAV vector or a rAAV particle disclosed herein (e.g., a rAAV particle comprising a nucleic acid sequence encoding 21OH) and a pharmaceutically acceptable carrier, diluent or excipient. As used herein, the term "pharmaceutically acceptable" refers to molecular entities and compositions that do not generally produce allergic or other serious adverse reactions when administered using routes well known in the art. Molecular entities and compositions approved by a regulatory agency of the U.S. Federal or a U.S. state government or listed in the U.S. Pharmacopeia or other generally recognized pharmacopeia for use in animals, and more particularly in humans are considered to be "pharmaceutically acceptable". As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Some examples of such carriers or diluents include, but are not limited to, water, saline, buffered saline, Ringer's solutions, dextrose solution, 5% human serum albumin and other buffers, e.g., HEPES, to maintain pH at appropriate physiological levels. The use of such media and agents for pharmaceutically active substances (e.g., recombinant virus particles) is well known in the art. Except insofar as any conventional media or agent is incompatible with the active compound, use thereof in the compositions is contemplated. Supplementary active compounds can also be incorporated into the compositions.

Throughout this description, "vg" may refer to "viral genomes" or "vector genomes".

Examples of pharmaceutical compositions and delivery systems that may be used for administration of the rAAV disclosed herein can be found in Remington: The Science and Practice of Pharmacy (2003) 20$^{th}$ ed., Mack Publishing Co., Easton, Pa.; Remington's Pharmaceutical Sciences (1990) 18$^{th}$ ed., Mack Publishing Co., Easton, Pa.; The Merck Index (1996) 12$^{th}$ ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11$^{th}$ ed., Lippincott Williams & Wilkins, Baltimore, Md.; and Poznansky et al., Drug Delivery Systems (1980), R. L. Juliano, ed., Oxford, N.Y., pp. 253-315.

A pharmaceutical composition of the invention may be formulated to be compatible with its intended route of administration. Examples of routes of administration include parenteral administration, e.g., intravenous administration, or injection. Injection may include direct injection into the adrenal gland via open surgery or laparoscopy or injection into an adrenal artery via catheterization. Solutions or suspensions used for parenteral (e.g., intravenous or via injection) application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For injection, a pharmaceutically acceptable carrier can be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference in its entirety. In one embodiment, the carrier is an isotonic sodium chloride solution. In another embodiment, the carrier is balanced salt solution. In one embodiment, the carrier includes TWEEN® (polysorbate). If the rAAV is to be stored long-term, it may be frozen in the presence of glycerol or TWEEN® (polysorbate) 20.

It is especially advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of active agent (e.g., rAAV) calculated to produce the desired therapeutic effect in association with the required pharmaceutical carrier. The specification for the dosage unit forms of the invention are dictated by and directly dependent on the unique characteristics of the active agent (e.g., rAAV) and the particular therapeutic effect to be achieved, and the limitations inherent in the art of compounding such an active agent (e.g., rAAV) for the treatment of individuals. Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Recombinant vector (e.g., rAAV) sequences, plasmids, vector genomes, recombinant virus particles (e.g., rAAV), and pharmaceutical compositions thereof can be packaged in single or multiple unit dosage form for ease of administration and uniformity of dosage.

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

In some embodiments, an effective concentration of a rAAV carrying a nucleic acid sequence encoding the desired transgene (e.g., 21OH) under the control of a promoter sequence ranges between about $10^8$ and about $10^{13}$ vector genomes per milliliter (vg/mL). For example, the rAAV infectious units may be measured as described in McLaughlin et al, *J. Virol.*, 62:1963 (1988). In some embodiments, the concentration is from about $1.5 \times 10^9$ vg/mL to about $1.5 \times 10^{12}$ vg/mL. In some embodiments, the concentration is from about $1.5 \times 10^9$ vg/mL to about $1.5 \times 10^{11}$ vg/mL. In one embodiment, the effective concentration is about $1.5 \times 10^{10}$ vg/mL. In another embodiment, the effective concentration is about $1.5 \times 10^{11}$ vg/mL. In another embodiment, the effective concentration is about $2.8 \times 10^{11}$ vg/mL. In yet another embodiment, the effective concentration is about $1.5 \times 10^{12}$ vg/mL. In a further embodiment, the effective concentration is about $1.5 \times 10^{13}$ vg/mL. In some embodiments, it is desirable that the lowest effective concentration of virus be utilized in order to reduce the risk of undesirable effects, such as toxicity or adverse immune response. Still other dosages in these ranges may be selected by the attending physician, taking into account the physical state of the subject (e.g., human) being treated, the age of the subject, the particular 21OH deficiency disorder and the degree to which the disorder, if progressive, has developed.

In some embodiments, rAAV vectors or rAAV particles comprising a nucleic acid sequence encoding 21OH are administered to a subject at a dose ranging from about $10^{11}$ to about $10^{14}$ vg/kg body weight of the subject. In some embodiments, rAAV vectors or rAAV particles comprising a nucleic acid sequence encoding 21OH are administered to a subject at a dose of about $1.5 \times 10^{12}$ vg/kg or $3 \times 10^{12}$ vg/kg.

A pharmaceutical composition comprising a rAAV vector or a rAAV particle comprising a nucleic acid sequence encoding 21OH can be included in a container, pack, or dispenser together with instructions for administration.

The invention will be further described in the following examples, which do not limit the scope of the invention described in the claims.

EXAMPLES

Example 1: Construction and Production of Recombinant Adeno-Associated Virus Vector and Particle and Treatment of Cells In Vitro The human 21-hydroxylase (CYP21A2) cDNA was fused to a hemagglutinin (HA) tag and was subcloned into a pAAV2-CAG plasmid to produce a pAAV2-CAG-CYP21A2-HA plasmid which included the viral inverted terminal repeat from AAV2 and the cytomegalovirus/β-actin hybrid (CAG) promoter. The CAG promoter consisted of the enhancer from the cytomegalovirus immediate-early gene, the promoter, splice donor and intron from the chicken β-actin gene, and the splice acceptor from the rabbit β-globin gene. A sham plasmid was constructed with a noncoding sequence of the β-galactosidase cDNA under the CAG promoter, which was used to generate a sham vector. The AAVrh10-CAG-CYP21A2-HA ("CYP21") and sham vectors were produced as previously described in the Vector Core at the University Hospital of Nantes. See, e.g., Gao, G. P., and Sena-Esteves, M. (2012). Introducing Genes into Mammalian Cells: Viral Vectors. In *Molecular Cloning, Vol 2: A Laboratory Manual* (M. R. Green and J. Sambrook eds.) pp. 1209-1313. Cold Spring Harbor Laboratory Press, New York; Rabinowitz et al., *J Virol,* 76(2):791-801 (2002). The AAVrh10-CAG-CYP21A2-HA virus contains a genome with AAV2 ITR sequences and encodes rh10 capsid proteins.

Mouse Y1 adrenocortical tumor cells were maintained with Ham's F10 medium supplemented with 2.5% fetal bovine serum, 15% horse serum, 1% glutamin, penicillin-streptomycin 1%. Cells were transfected with pAAV2-CAG-CYP21A2-HA ("pCYP21") or pAAV2-CAG-Luciferase ("pLuc") using FuGENE HD (Promega, Charbonnieres les Bains, France). Supernatant and cells were harvested 48 h after transfection.

Examples 1-6 and related figures are also described in Perdomini et al., *Gene Therapy,* 24(5): 275-281 (2017).

Example 2: General Description of 21-Hydroxylase Deficiency in a Murine Model and Procedures for Animal Treatment A mouse model of 21-hydroxylase deficiency (21OHD) is provided by H-2$^{aw18}$ mice (Cyp21$^{-/-}$) that lack 21OH activity. The genetic defect is caused by an unequal crossing over between the active Cyp21a1 gene and the pseudogene, resulting in a hybrid Cyp21a1-Cyp21a2-p gene that includes a partial deletion of Cyp21a1 (Riepe et al., *Endocrinology* 2005; 146: 2563-2574). Cyp21$^{-/-}$ mice are known to have an abnormal hypothalamic-pituitary-adrenal feedback, alterations in the structure and function of the adrenal medulla and cortex (Tajima et al., *Endocrinology* 1999; 140: 3354-3362; Bornstein et al., *FASEB J* 1999; 13: 1185-1194). Without glucocorticoid administration, the deletion of the Cyp21a1 gene in this mouse model is known to be lethal. Cyp21$^{-/-}$ mice remain extremely vulnerable despite early glucocorticoid administration to mothers and pups. Frailty remains the rule in the adult Cyp21$^{-/-}$ mice that survive the neonatal period (Tajima et al., *Endocrinology* 1999; 140: 3354-3362).

Heterozygous mice were bred to generate mice homozygous for the mutation. Homozygous (Cyp21$^{-/-}$) mice, heterozygous (Cyp21$^{+/-}$) and wild-type (Cyp21$^{+/+}$) littermates were used for the experiments and analyses. The genotypes of the mice were confirmed using a PCR-based assay with genomic DNA from tail biopsy. All dams received injections of 5 g dexamethasone from gestational day 20 until postnatal day 7 of newborns. Pups were treated every 2 days with corticosterone (5 μg per day) and fludrocortisone (0.025 μg per day) until day 14. After this age, mice were maintained in a temperature- and humidity-controlled animal facility with a 12-h light-dark cycle, free access to regular rodent diet pellets and water ad libitum. Both male and female mice were used in all experiments. All animal procedures and experiments were approved by the local ethical committee (Ethical Committee of CEA, the CEtEA) and the French Ministry of National Education, Higher Education and Research (20150401 1101 8958 (APAF1S #410). 01), and were performed in accordance with the Guide for the Care and Use of Laboratory Animals (US National Institutes of Health).

Example 3: Experimental Methods

Animal Procedures

For biodistribution study, adult control mice were anesthetized with isoflurane (3%) to allow intravenous administration by retro-orbital injection of AAVrh10-CAG-GFP at a dose of 2×10$^{10}$ vector genomes per gram of body weight. Three weeks after treatment, mice were injected intraperitoneally with pentobarbital and perfused with cooled saline solution.

For gene therapy studies, Cyp21$^{-/-}$ mice received the CYP21 vector at a dose of 2×10$^{10}$ vector genomes per gram of body weight. Cyp21$^{-/-}$, Cyp21$^{-/-}$ and Cyp21$^{+/+}$ mice littermates were injected with a dose of 2×10$^{10}$ vector genomes per gram of body weight of the sham vector.

Urine was collected (following bladder massage) between 9:00 and 11:00 am. Care was taken to ensure that urine was not contaminated with feces or other material from the animal's cage. All samples were aliquoted and frozen immediately at −20° C.

Eighteen weeks after treatment, mice were intraperitoneally injected with pentobarbital and perfused with cooled saline solution. Blood was collected by intracardiac puncture. Tissues samples for biochemical and molecular analyses were immediately frozen in liquid nitrogen. For histological analysis, tissues were post-fixed in PFA 4%, cryoprotected in sucrose and embedded in OCT (Thermo Fisher Diagnostics, Asnieres sur Seine, France) and snap-frozen in isopentane chilled in dry ice.

Histopathology

For histochemical analysis, 10-μm cryosections were stained with hematoxylin and eosin.

Immunofluorescence and Image Acquisition

The expression of the AAVrh10-CAG-GFP vector was assessed through GFP detection by green fluorescence. Microscopy analysis was performed on a Nikon Eclipse TI inverted microscope (Champigny sur Marne, France).

Vector Copy Number (VCN) Determination

DNA was extracted from different tissues using the DNeasy Blood&Tissue kit (Qiagen, Courtaboeuf, France) according to the manufacturer's protocol. The amount of vector genomes per diploid cell for each tissue was determined by qPCR with the Platinum Quantitative PCR SuperMix-UDG (Thermo Fisher Scientific, Courtaboeuf, France) using the standard conditions. Primers were targeted against the CYP21A2 transgene (forward 5'-ACAGTCATCATTCCGAACCTCCA-3' (SEQ ID NO:4), reverse 5'-AAGGCCAGAGCTCTGGAGTTCTT-3' (SEQ ID NO:5)) and the mouse brain-derived neurotrophic factor of the host genome (forward 5'-TGCTGGATGAGGACCAGAAGGTT-3' (SEQ ID NO:6), reverse 5'-AGGAGGCTCCAAAGGCACTTGA-3' (SEQ ID NO:7)). Amplifications were performed using the Light Cycler 480 (Roche Diagnostics, Meylan, France).

Quantitative Real-Time PCR

Total RNA was extracted from snap-frozen tissues using a Precellys24 homogenizer (Ozyme, Saint-Quentin-en-Yvelines, France) and RNeasy mini kit (Qiagen) according to the manufacturer's protocol and was treated with DNAse I (Promega). cDNA was generated by reverse transcription using the SuperScript VILO cDNA Synthesis Kit (Thermo Fisher Scientific). Quantitative RT-PCR was performed using the Platinum Quantitative PCR SuperMix-UDG (Thermo Fisher Scientific) and Light Cycler 480 (Roche Biosciences) with primers described in Table 1. The gene coding for the mouse TATA box binding protein (Tbp) was used as the internal standard. Raw data were normalized according to the amount of cortical cells for each genotype.

TABLE 1

Primer pairs.

| gene | Forward primer | SEQ ID NO | Reverse primer | SEQ ID NO |
|---|---|---|---|---|
| Mc2r | TTTCTCAGTCATCTTGCCGA | 8 | ATGCTCCTCTCCTTGGCTTT | 9 |
| Prkar1a | GCATTCCTTCGGGAATACTTT | 10 | CCCTCGAGTCAGTACGGATG | 11 |

TABLE 1-continued

Primer pairs.

| gene | Forward primer | SEQ ID NO | Reverse primer | SEQ ID NO |
|---|---|---|---|---|
| Prkar2a | GAGTGACTCGGACTCGGAAG | 12 | CCTCCTCTTCTTCATCAGGG | 13 |
| Prkarca | AAGAAGGGCAGCGAGCAG | 14 | ATTCTGAGAAGGGGTCTCCC | 15 |
| Prkarcb | CAAGAAAGGCAGCGAAGTG | 16 | TCCTCAAGCCCAGCATTACT | 17 |
| Sf1 | GCCAGGAGTTCGTCTGTCTC | 18 | TTTCCTGGGCGTCCTTTAC | 19 |
| Star | GGGCATACTCAACAACCAGG | 20 | GAAACACCTTGCCCACATCT | 21 |
| Cyp11a1 | CAGGCCAACATTACCGAGAT | 22 | CCTTCAAGTTGTGTGCCATC | 23 |
| Hsd3b1 | GTTGTCATCCACACTGCTGC | 24 | CAGGCCTCCAATAGGTTCTG | 25 |
| Cyp11b1 | ATGGACTTTCAGTCCAGTGTGTTC | 26 | GCCGCTCCCAAAAAGAA | 27 |
| Cyp17a1 | GAAGTGCTCGTGAAGAAGGG | 28 | CTACTATCCGCAAAGGCGAC | 29 |
| Cyp11b2 | GAGACGTGGTGTGTTCTTGC | 30 | TCCCTTGCTACCATGTCCAC | 31 |
| CYP21 | ACAGTCATCATTCCGAACCTCCA | 32 | AAGGCCAGAGCTCTGGAGTTCTT | 33 |
| Renin | CTCTGGGCACTCTTGTTGCT | 34 | AGAAGGCATTTTCTTGAGCG | 35 |
| Tbp | CCCTTGTACCCTTCACCAATGAC | 36 | TCACGGTAGATACAATATTTTGAAGCTG | 37 |

Immunoblot Analysis

Extracts of tissues or Y1 cells were homogenized in lysis buffer (Promega). Total protein extract (5 µg) was analyzed on nupage 4-12% Bis-Tris Gels NP0323BOX (ThermoFisher Scientific). Proteins were transferred to nitrocellulose membranes, blocked with 5% non-fat milk and then incubated with the following primary antibodies: polyclonal antibody to 21-hydroxylase which detects human and mouse protein (Corgen, Taipei, Taiwan), antibody to GAPDH (Abcam, Cambridge, UK; Ab9484, 1:3000). Secondary antibody anti-mouse IgG (GE Healthcare, Vélizy Villacoublay, France) coupled to peroxydase was diluted at 1:3000 and used for detection of the reaction with Clarity Western ECL Substrate (Bio-rad, Marnes la Coquette, France).

Hormonal Assays

Progesterone concentration in Y1 supernatant and mouse urine was measured using commercial progesterone EIA (Arbor Assays, Ann Arbor, MI, USA). Urinary progesterone concentration was normalized using creatinine concentration (Urinary Creatinine Detection Kit; Arbor Assays).

Behavioral Analysis

Tests were performed 15 weeks after gene therapy treatment.

Tail suspension Test. Mice were suspended by their tails with tape in such a position that they could not escape or hold on to nearby surfaces. The behavior was tracked with EthoVision XT 10.5 (Noldus Information Technology B.V., Wageningen, The Netherlands) video tracking and analysis software. Duration of immobility, defined by the absence of all movement except for those required for respiration, was measured for 6 min.

Elevated plus maze. The apparatus, consisting of two open and two enclosed arms, was illuminated indirectly by an overhead lamp with an intensity of 100 lux. For testing, mice were individually placed on the center square and allowed to freely explore the maze for 6 min. Their behavior was recorded and analyzed by the video tracking software EthoVision 10.5 (Noldus Information Technology B.V.).

After behavioral testing, the equipment was cleaned with 10% ethanol solution. Parameters assessed were time spent in open or closed arms, number of head dips, number of rearing and total distance traveled.

Rotarod. Motor balance and coordination was determined using an accelerating rotarod apparatus (Ugo Basile, Gemonio, Italy). Training of animals consisted of one trial of 2 min at four rotations per minute (r.p.m.). They were then tested in three consecutive trials of 5 min with increasing speed of the rod from 4 to 40 r.p.m. Mice were allowed to recover for 45 min between trials. The trial lasted until the mouse fell from the rod. The latency to fall was recorded. This sequence was repeated on three consecutive days. After behavioral testing, the equipment was cleaned with 10% ethanol solution.

Statistics

Comparisons between the groups were made with the Mann-Whitney test. GraphPad Prism (GraphPad Software, La Jolla, CA, USA) software was used.

Example 4: Physical and Biochemical Phenotype of Cyp21$^{-/-}$ Mice

Only 12% of Cyp21$^{-/-}$ mice survived the neonatal period. Mice were thus studied during adulthood. Despite glucocoid treatment of dams and pups, those Cyp21$^{-/-}$ survivors grew lighter and frail compared with controls or heterozygous mice (FIGS. 1A and 1). Since Cyp21$^{+/-}$ mice and Cyp21$^{+/+}$ mice had a comparable evolution of body weight during the study, we pooled their data as a 'control' group for comparison. The locomotor activity of the Cyp21$^{-/-}$ mice tested with the Rotarod was normal (FIG. 2A). Unexpectedly, the Cyp21$^{-/-}$ mice showed traits of anxiety and depressive-like behavior, such as behavioral despair during the tail suspension test and decreased performances in the elevated plus-maze test (FIGS. 2B-2F).

Figure 6:
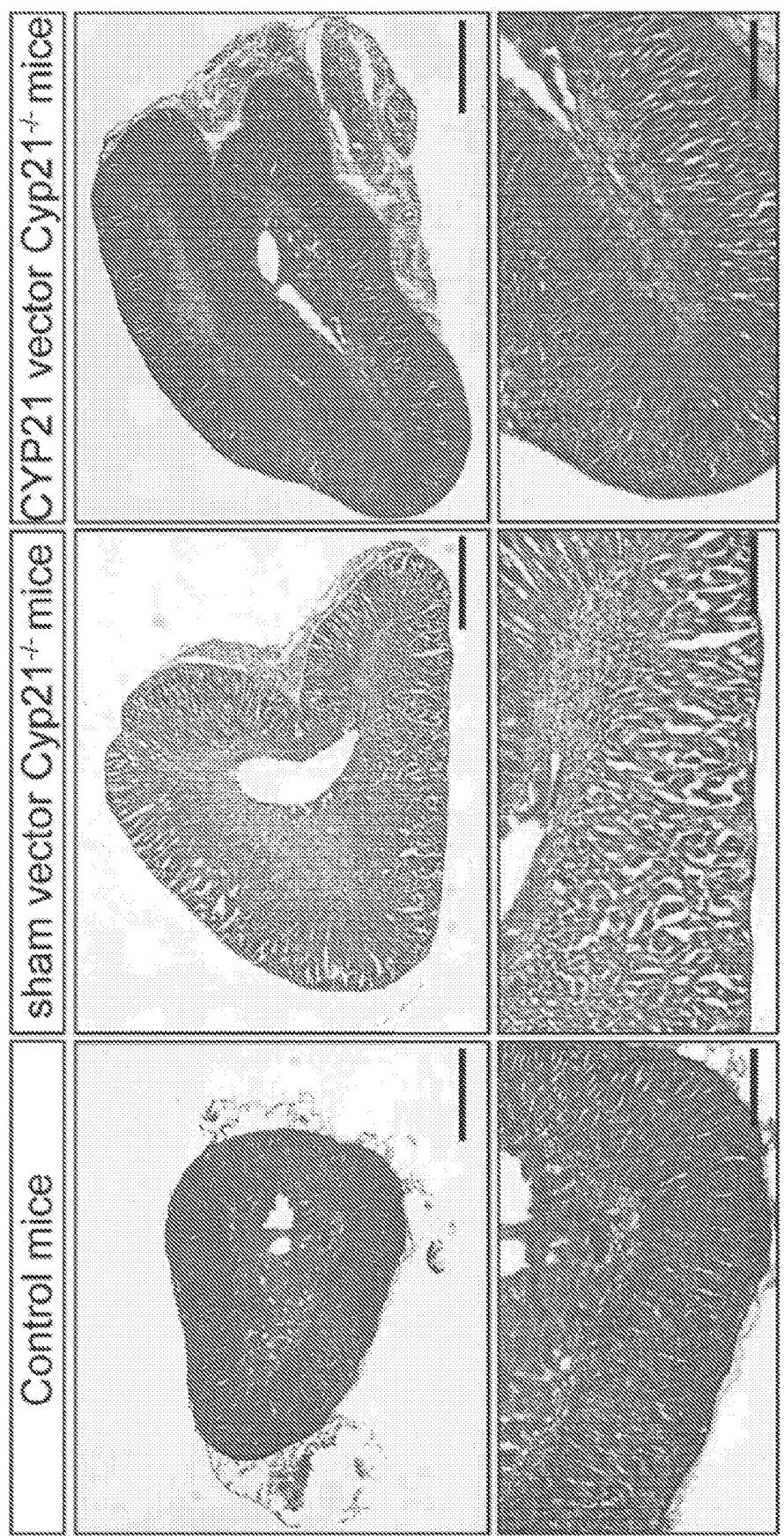
FIG. 6 shows images of histological analysis of adrenal cryosections of control mice and Cyp21$^{-/-}$ mice injected with the sham vector or the CYP21 vector. Top, scale bar=500 μm; bottom, scale bar=200 μm.

Adrenal glands of the Cyp21$^{-/-}$ mice were 2.1-fold larger than those of control mice. Adrenal architecture was ill-organized with perturbation of zonation and nodules. Cells of the adrenal cortex were in normal number but showed hypertrophy and irregular shape with heterogeneous nuclei (FIG. 6).

Progesterone, the main substrate of 21-hydroxylase, was elevated (44-fold normal) in the urine of Cyp21$^{-/-}$ mice (FIG. 1C).

Figure 3A:
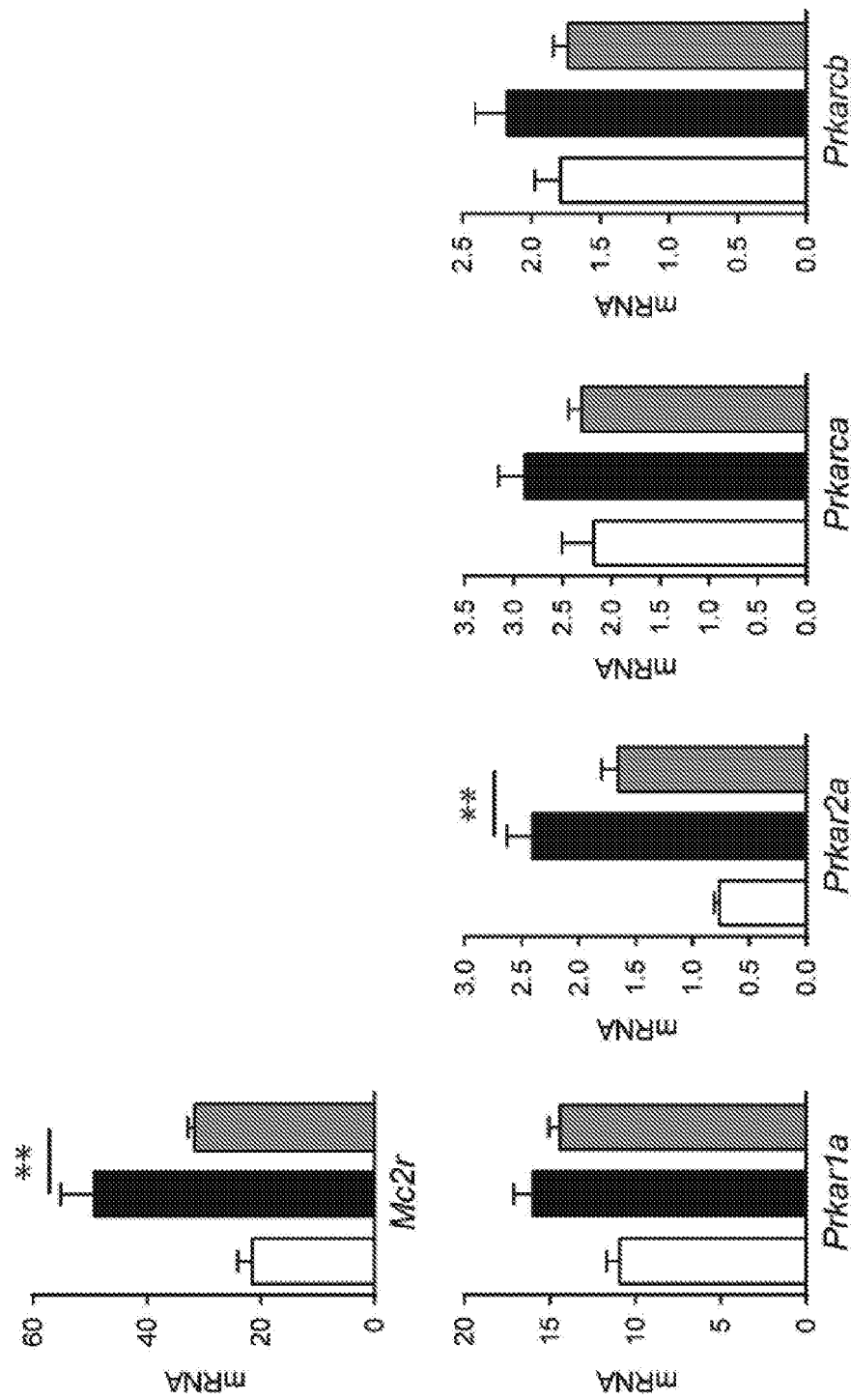
FIG. 3A and FIG. 3B are bar graphs showing the results of studies of gene expression in adrenals and kidneys of Cyp21$^{-/-}$ mice injected with CYP21 vector (gray, n=11) or sham vector (black, n=8) compared with control mice (white, n=16).
Figure 3A:
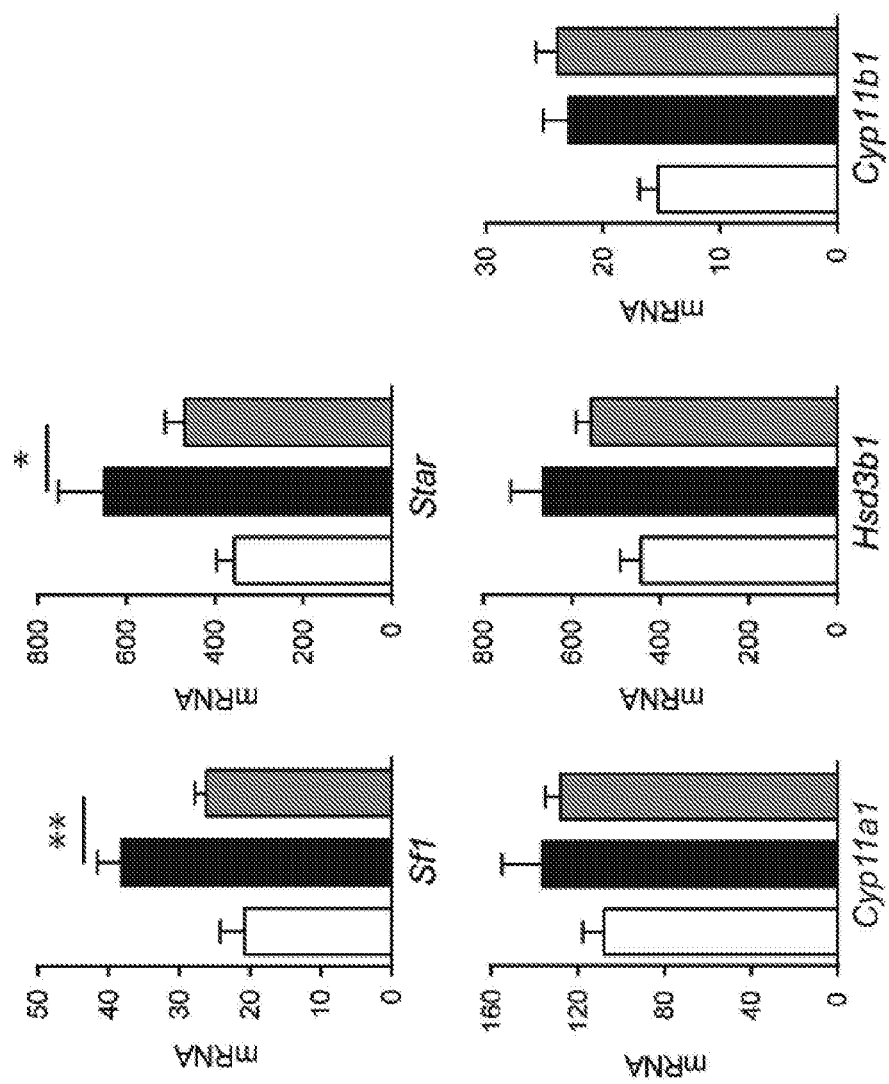
Figure 3A:
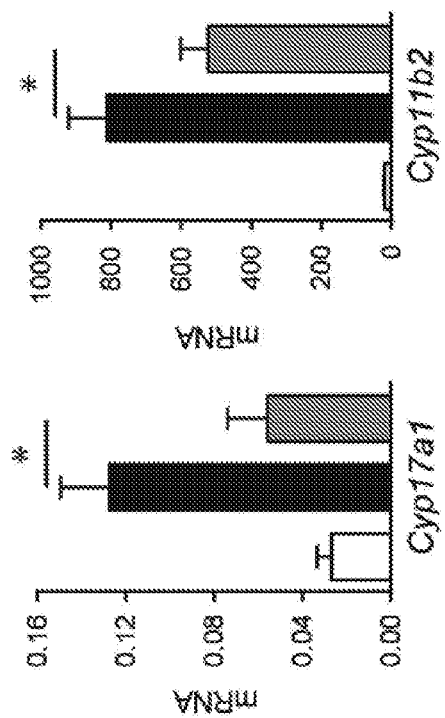
Figure 7:
FIG. 7 shows images of aldosterone synthase expression in adrenals of control mice and Cyp21$^{-/-}$ mice injected with the sham vector or the CYP21 vector.

Salt loss could not be precisely measured due to technical constraints, but the expression of Renin was increased 160-fold in the kidneys of the Cyp21$^{-/-}$ mice (FIG. 3B), indicating a dramatic renal response to the chronic salt loss associated with the loss of mineralocorticoid function characterizing these animals. Accordingly, the expression of aldosterone synthase (Cyp11b2) showed a 40-fold increase in the adrenals of Cyp21$^{-/-}$ mice located in the zona glomerulosa (FIG. 3A), which was confirmed by immunofluorescence analysis (FIG. 7). The expression of Mc2r, PKA subunits (Prkar1a, Prkar2a, Prkarca, Prkarcb) and SF-1 genes was increased in the adrenals of Cyp21$^{-/-}$ mice compared with control mice. The expression of Star, Cyp11a1, Hsd3b1 and Cyp11b1 was also significantly increased (FIG. 3A). Cyp17a1, which is not expressed in normal adult mouse adrenals, was slightly expressed in Cyp21$^{-/-}$ mice (FIG. 3A).

Example 5: CYP21 Expression and Function in Adrenal Cells

Figure 4A:
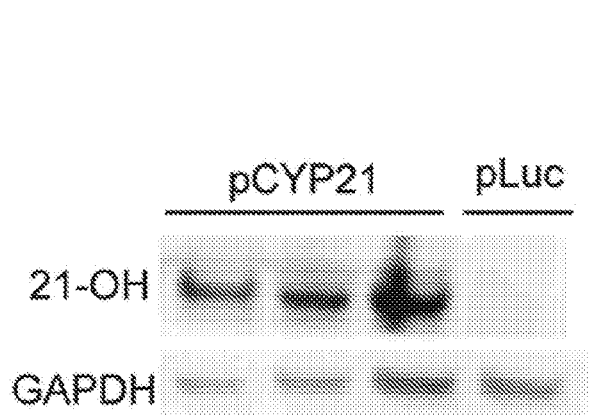
FIG. 4A and FIG. 4B show results of analysis of 21-Hydroxylase expression and progesterone concentration in Y1 cells transfected with pCYP21 (n=3, gray) or pLuc (n=3, black).
Figure 4B:
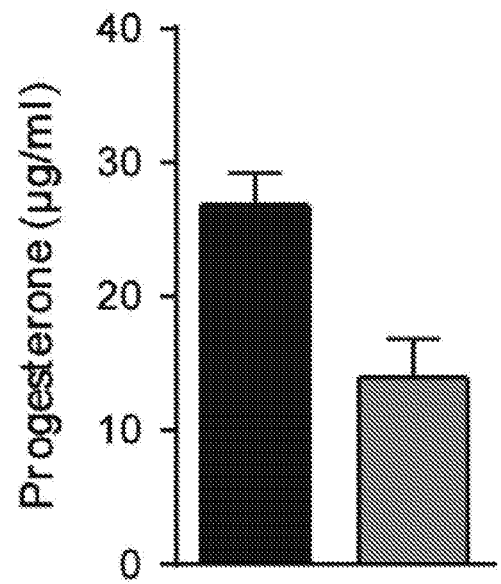

The Y1 cell line metabolizes steroids into 11/8,20a-dihydroxyprogesterone but does not produce 21-hydroxylated steroid products (Parker et al., *Proc Natl Acad Sci USA* 1985; 82: 7860-7864). In vitro, Y1 cells transfected with the pCYP21 plasmid expressed the 21OH protein (FIG. 4A) and showed a lower progesterone concentration in supernatant than Y1 cells transfected with the non-functional pLuc plasmid (FIG. 4B). The transfection of these cells with pCYP21 resulted in 21OH expression. This resulted in a decreased progesterone concentration in the supernatant in the transfected cell culture, indicating that the transduced 21OH has increased the metabolism of progesterone. This implied that the CAG promoter allowed 21OH gene expression up to a functional level.

Figure 5A:
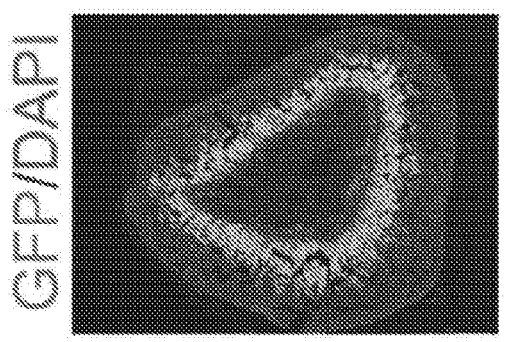
FIG. 5A and FIG. 5B show that intravenous injection of AAVrh10 results in transgene expression in the adrenal cortex.
Figure 8:
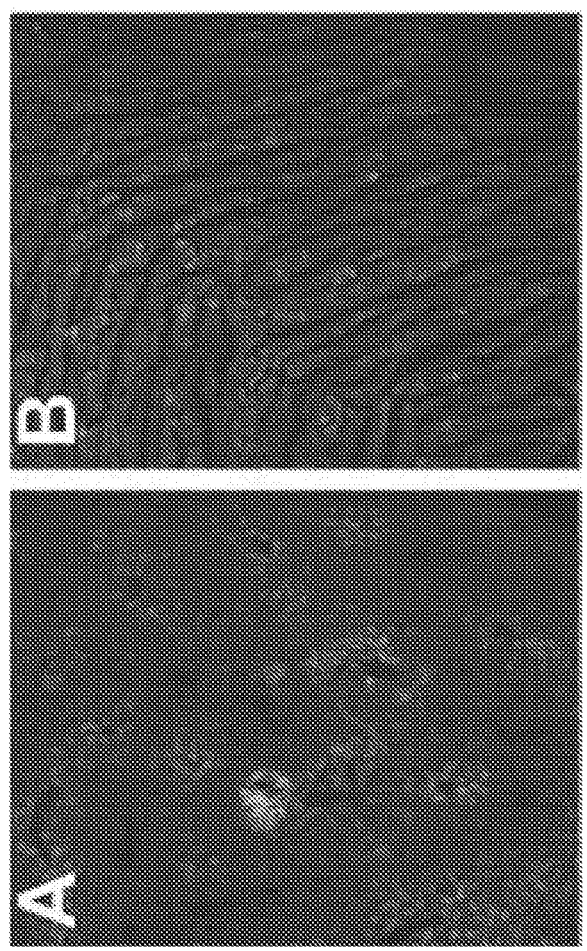
FIG. 8A and FIG. 8B show images of GFP expression in peripheral organs of control mice injected intravenously with AAVrh10-CAG-GFP.
Figure 9:
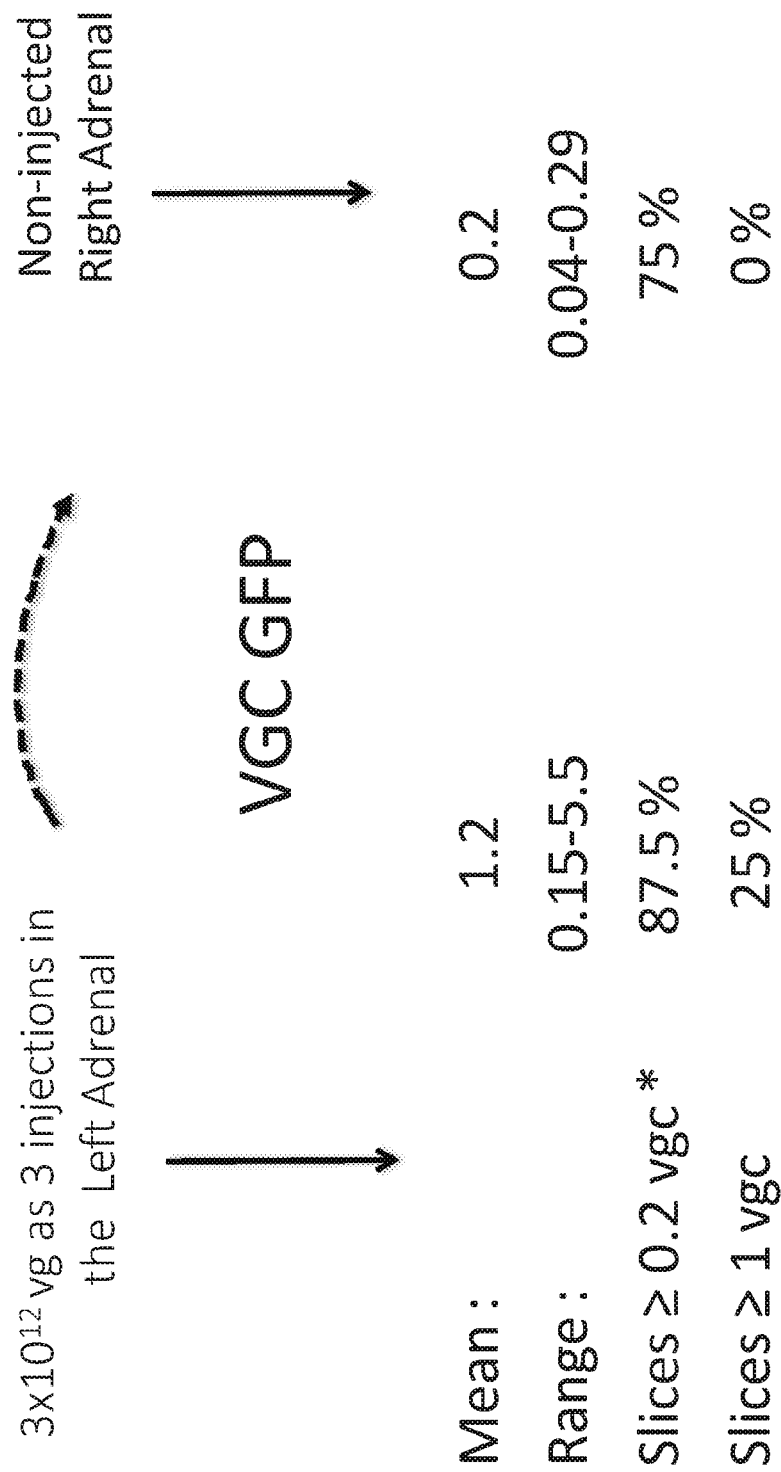
FIG. 9 shows GFP viral genome copy (VGC) measurements for the adrenal glands of non-human primate number 1 (NHP01) injected with ssAAV5-PGK-GFP in the left adrenal gland. VGC counts in both the right (non-injected) and left (injected) adrenals are shown. The asterisk indicates the VGC that was effective in treating Cyp21$^{-/-}$ mice in Examples 1-6.

Following intravenous injection of control mice with $2 \times 10^{10}$ vector genomes per gram body weight of AAVrh10 encoding green fluorescent protein (GFP), widespread GFP expression was observed in the *reticularis* and *fasciculata* zonae of the adrenal cortex (FIG. 5A). The fraction of cells that expressed GFP was approximatively 39%. Heart and liver also expressed GFP (FIG. 8) while kidney, gonads and brain did not express GFP.

Figure 5B:
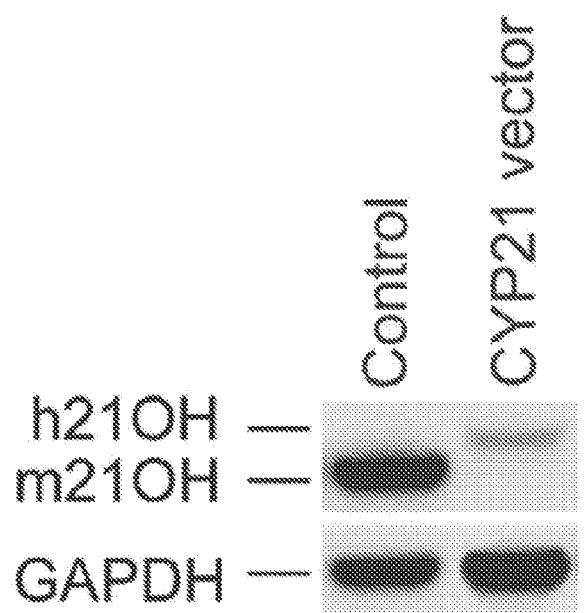

$2 \times 10^{10}$ vector genomes per gram body weight of AAVrh10-CAG-CYP21A2-HA ("CYP21") vector or AAVrh10-null (sham) vector were injected intravenously to adult Cyp21$^{-/-}$ or control mice. Eighteen weeks after treatment, the mean count of vector copies per cell number (VCN) was 0.13±0.09 in whole adrenal tissue including cortex and medulla. Human 21-hydroxylase was detected in the adrenals of Cyp21$^{-/-}$ mice at a lower level than endogenous 21OH level in control mice (FIG. 5B). The 21-hydroxylase enzyme was expressed in a large number of cells in the ill-organized *fasciculata* zona of the Cyp21$^{-/-}$ mice. Few VCN and no CYP21 expression was detected in the liver. Expression was weak in heart and not detected in kidney, gonads and brain (Table 2).

TABLE 2

CYP21 vector copy number (VCN) per cell and CYP21 mRNA content in peripheral organs of Cyp21$^{-/-}$ mice treated with the CYP21 vector (n = 16).

| | Vector copy number | | mRNA | |
|---|---|---|---|---|
| Organ | Mean | Standard Deviation | Mean | Standard Deviation |
| Heart | 0.058 | 0.055 | 0.08 | 0.11 |
| Liver | 0.055 | 0.025 | ND | — |
| Kidney | 0.009 | 0.005 | ND | — |
| Gonads | ND | — | ND | — |

ND: not detected.

It was not attempted to inject the AAVrh10 vector in the retro-orbital vein of Cyp21$^{-/-}$ pups for practical reasons owing to the frailty of the pups and the risk of killing by mothers in response to manipulation.

Example 6: Effects of the CYP21 Vector

Cyp21$^{-/-}$ mice treated with the functional CYP21 vector showed an early and sustained increase of their body mass (FIG. 1A) and improved physical appearance when compared with Cyp21$^{-/-}$ mice injected with the sham vector (FIG. 1). Within 5 weeks following injection of the CYP21 vector, the progesterone level decreased by 42% and then remained near normal in Cyp21$^{-/-}$ mice (FIG. 1C) until 15 weeks of the study. Cyp21$^{-/-}$ mice treated with the CYP21 vector recovered a normal reaction to the tail suspension test and showed improved performances in the elevated plus-maze test (FIGS. 2B-2F).

CYP21 vector treatment did not correct the alterations of adrenal morphology (FIG. 6).

CYP21-injected mice showed a major correction of renin expression in the kidney (FIG. 3B), since levels of expression were decreased 14-fold following the restoration of 21-hydroxylase activity. This reflected an improved mineralocorticoid function allowing the treated animals to retain salt.

CYP21 vector treatment of Cyp21$^{-/-}$ mice decreased the expression of overexpressed Mc2r, Prkar2a, Sf1, Star, Cyp17a1 and Cyp11b2 genes to near-normal levels (FIG. 3A). No significant changes in Prkar1a, Prkaca, Prkacb, Hsd3b and Cyp11b1 gene expression were observed (FIG. 3A).

Thus, in vivo, the measure of the mean VCN present in whole adrenal tissue was limited but sufficient to restore a large part of the steroidogenic activity of the cortex. This is shown by the decrease in progesterone in urine down to near-normal values, which was studied over 15 weeks in the same animals, showing a persistent effect of CYP21 vector treatment (FIG. 1C).

Figure 3B:
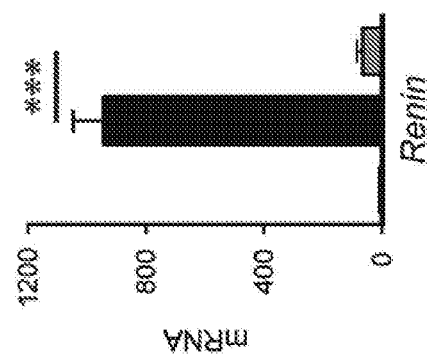

The chronic salt loss occurring before CYP21 vector treatment was reflected by a dramatically increased Renin gene expression in the kidney, which was decreased by CYP21 vector treatment (FIG. 3B). Accordingly, the CYP21 vector-treated Cyp21$^{-/-}$ mice increased their body weight and improved their general appearance (FIGS. 1A and 1).

The administration of the CYP21 vector to Cyp21$^{-/-}$ mice led to a near normalization of previously increased progesterone production, reflecting a major and sustained restoration of the 21-hydroxylase activity which was still functioning at the last analysis at 15 weeks of CYP21 vector treatment.

Poor response to stress is a newly reported trait of the Cyp21$^{-/-}$ mice, which could be due to the absence of an appropriate glucocorticoid response by the adrenal cortex. The prominent role of the hypothalamic-pituitary-adrenal axis on the development of depressive-like traits is shown by several studies in mice that have genetically altered receptors to glucocorticoid or to corticotropin-releasing hormone (Smith et al., *Neuron* 1998; 20: 1093-1102; Ridder et al., *J Neurosci* 2005; 25: 6243-6250; Bale et al., Nat Genet 2000; 24: 410-414) or adrenal hypoplasia (Bland et al., *Proc Natl Acad Sci USA* 2000; 97: 14488-14493). Indeed, all of these mouse models show distinctive depression-like features and dysregulation of stress responses. According to the observations in the Cyp21$^{-/-}$ mice and without being bound by theory, it is possible that the lack of an adequate glucocorticoid secretion by the adrenals during early life could have durably altered the stress response (Sapolsky et al., *Endocr Rev* 2000; 21: 55-89). These depression-like traits were reversed in the Cyp21$^{-/-}$ mice treated with the AAVrh10 vector (FIG. 2) that restored 21OH activity in the adrenal cortex.

Cyp21$^{-/-}$ mice had both adrenal hypertrophy, disorganization of architecture (FIG. 6) and major changes in the expression of genes coding for steroidogenic enzymes and ACTH-dependent signaling proteins (FIG. 3A). Given the trophic effects of ACTH on adrenal growth, it is likely that the gross changes in adrenal cellular morphology and gene expression were due to chronically elevated ACTH. The early administration of glucocorticoids to the Cyp21$^{-/-}$ pups, while allowing a few mice to survive postnatal times, was not sufficient to avoid these changes. This suggests that the glucocorticoid treatment had only partial suppressive effects on corticotropin secretion. The 21OH transduced by the AAVrh10 vector into the adrenal cortex of the Cyp21$^{-/-}$ mice corrected a large part of the compensatory steroidogenic enzyme and ACTH-dependent protein expression. Increased expression of aldosterone synthase gene in the adrenal cortex and of renin gene in the kidneys, which were considerably increased 40-fold in Cyp21$^{-/-}$ mice in an attempt to match chronic salt loss, both showed a major decrease in CYP21 vector-treated animals.

It is noteworthy that the striking effects of CYP21 vector treatment on adrenal function occurred with only about 39% of adrenocortical cells expressing the transduced CYP21. This suggests that functional recovery of only a proportion of cells can substantially correct the steroidogenic capacity of the adrenals, and that it would not be necessary to express 21OH in the whole adrenal cortex to obtain therapeutic benefits. This expression in a limited proportion number of cells was also observed in previous studies that allowed a brief (Tajima et al., *Gene Therapy* 1999; 6: 1898-1903) or partial (Macapagal et al., *Abstract the Endocrine Society's 84th Annual Meeting*, San Francisco, 2002, pp 1-503; Naiki et al., *Endocr J* 2016; 63: 897-904) correction of progesterone production. In contrast, the genetic therapy approach mediated by the AAVrh10 vector showed a persistent efficacy in the Cyp21$^{-/-}$ mice, with a limited, if any, spreading of 21-hydroxylase expression to other organs.

Example 7: Studies with AAV5-PGK rAAV

A ssAAV5-PGK-CYP21HA vector and a ssAAV5-PGK-GFP vector were produced. These vectors contain a genome with AAV2 ITR sequences and encode AAV5 capsid proteins. These rAAVs were administered to wild-type mice (B6) intravenously (i.v.) and to three non-human primates (NHP) (*Macaca fascicularis*) via intra-adrenal injection as shown in Table 3.

TABLE 3

Administration of AAV5-PGK rAAV.

| Vector | Dose per animal (vg) | Route | NHP or mice | Lot no. |
|---|---|---|---|---|
| ssAAV5-PGK-GFP | 3 × 10$^{12}$ | Intra-adrenal (left adrenal) | NHP01 | GVPN#6593 |
| SSAAV5-PGK-CYP21HA | 3 × 10$^{12}$ | Intra-adrenal (right adrenal) | NHP01 | GVPN#6594 |
| SSAAV5-PGK-CYP21HA | 4.5 × 10$^{11}$ | Intra-adrenal (right adrenal) | NHP02 | GVPN#6594 |
| SSAAV5-PGK-CYP21HA | 9 × 10$^{12}$ | Intra-adrenal (right adrenal) | NHP04 | GVPN#6594 |
| ssAAV5-PGK-GFP | 6 × 10$^{11}$ | i.v. (2 × 10$^{13}$/kg) | Mice | GVPN#6593 |
| SSAAV5-PGK-GFP | 1.5 × 10$^{12}$ | i.v. (5 × 10$^{13}$/kg) | Mice | GVPN#6608 |
| SSAAV5-PGK-GFP | 6 × 10$^{12}$ | i.v. (2 × 10$^{14}$/kg) | Mice | GVPN#6608 |
| SSAAV5-PGK-CYP21HA | 4.7 × 10$^{11}$ | i.v. (2 × 10$^{13}$/kg) | Mice | GVPN#6594 |
| ssAAV5-PGK-CYP21HA | 1.1 × 10$^{12}$ | i.v. (5 × 10$^{13}$/kg) | Mice | GVPN#6613 |

GFP and CYP21HA vector genome copy (VGC) values were determined for the animals treated with the rAAV (Table 4; FIGS. 9, 12, 14, 16-21 and 41) at 3 weeks post-treatment. VGCs were calculated in 7 to 9 adrenal slices for NHP01, in 8 slices for NHP02, in 60 adrenal cubes for NHP04, and in the entire adrenal in mice. DNA was extracted from adrenal (mice) or adrenal slices/cubes (NHPs) using the QIAamp DNA FFPE Tissue Kit (Qiagen, Courtaboeuf, France) according to the manufacturer's protocol. The amount of vector genomes per diploid cell for each sample was determined by qPCR with the Platinum Quantitative PCR SuperMix-UDG (Thermo Fisher Scientific, Courtaboeuf, France) using the standard conditions. Primers were targeted against the human CYP21A2 transgene (forward 5'-AAATTCGGGCCCATCTACAGG-3' (SEQ ID NO:38), reverse 5'-ATGGCTTCCT-CAATGGTCCTC-3' (SEQ ID NO:39)), the *macaca* albumin of the host genome (forward 5'-CTGT-CATGCTGCTGCTGAGACTT-3' (SEQ ID NO:40), reverse 5'-CTTTGGCATAGCATTCATGAGGAT-3' (SEQ ID NO:41)), and the mouse brain-derived neurotrophic factor of the host genome (forward 5'-TGCTGGAT-GAGGACCAGAAGGTT-3' (SEQ ID NO:42), reverse 5'-AGGAGGCTCCAAAGGCACTTGA-3' (SEQ ID NO:43)). Amplifications were performed using the Light Cycler 480 (Roche Diagnostics, Meylan, France). Human specific CYP21A2 primers were designed in the less conserved fragment after alignment of human and macaca cDNA sequences. There is only one mutation on human forward primer compared to macaca endogenous CYP21 genomic DNA, but hybridization is specific to human CYP21.

GFP and HA expression was also visualized by immunofluorescence (IF) (FIGS. 10, 11, 13, 15, 19 and 20) at 3 weeks post-treatment.

TABLE 4

Effects of AAV5-PGK rAAV.

| Vector | Dose per animal (vg) | Route | NHP or mice | Mean VGC in the injected adrenal (if intra-adrenal) |
|---|---|---|---|---|
| SSAAV5-PGK-GFP | $3 \times 10^{12}$ | Intra-adrenal (left adrenal) | NHP01 | 1.2 |
| SSAAV5-PGK-CYP21HA | $3 \times 10^{12}$ | Intra-adrenal (right adrenal) | NHP01 | 98 |
| SSAAV5-PGK-CYP21HA | $4.5 \times 10^{11}$ | Intra-adrenal (right adrenal) | NHP02 | 1.9 |
| ssAAV5-PGK-CYP21HA | $9 \times 10^{12}$ | Intra-adrenal (right adrenal) | NHP04 | 60.1 |
| SSAAV5-PGK-GFP | $6 \times 10^{11}$ | i.v. ($2 \times 10^{13}$/kg) | Mice | 0.2 |
| SSAAV5-PGK-GFP | $1.5 \times 10^{12}$ | i.v. ($5 \times 10^{13}$/kg) | Mice | 3.2 |
| SSAAV5-PGK-GFP | $6 \times 10^{12}$ | i.v. ($2 \times 10^{14}$/kg) | Mice | 16.6 |
| SSAAV5-PGK-CYP21HA | $4.7 \times 10^{11}$ | i.v. ($2 \times 10^{13}$/kg) | Mice | 0.12 |
| SSAAV5-PGK-CYP21HA | $1.1 \times 10^{12}$ | i.v. ($5 \times 10^{13}$/kg) | Mice | 17.6 |

The GFP VGC in the liver of non-human primate number 1 (NHP01) injected with ssAAV5-PGK-GFP in the left adrenal was 26 at the end of surgery. The GFP VGC for the same animal at euthanasia was 0.4. Immunofluorescence of the liver did not show any expression of GFP in this animal.

Figure 19:
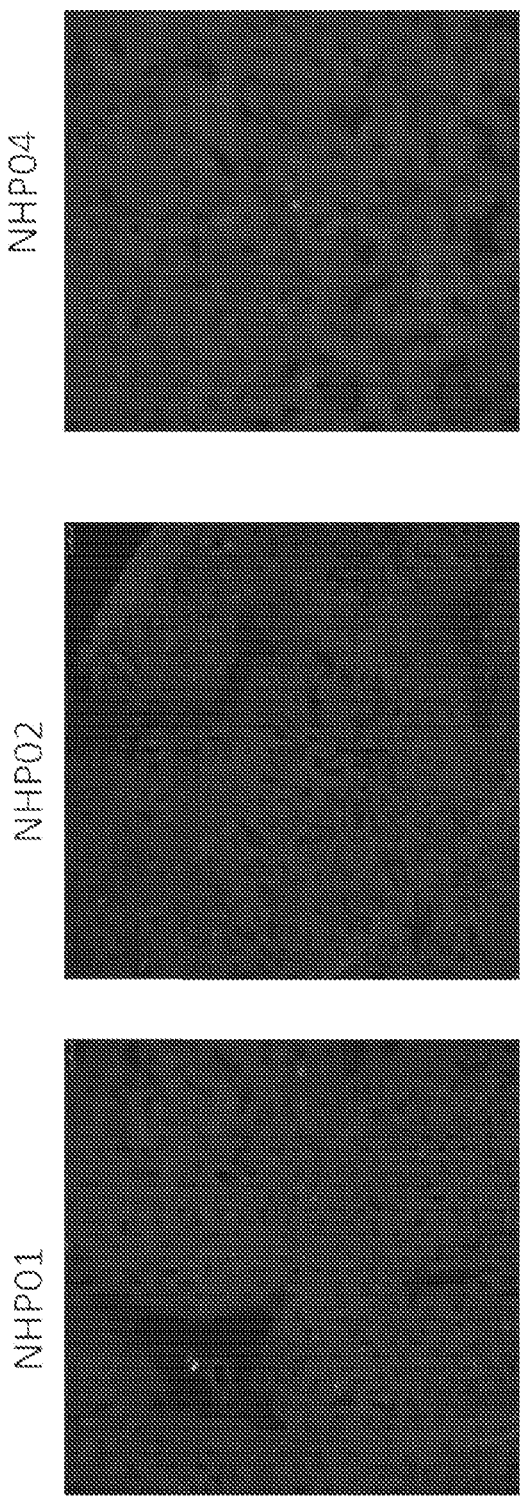
FIG. 19 shows mean CYP21HA viral genome copy (VGC) measurements for ssAAV5-PGK-CYP21HA in the livers of NHP01 and NHP02 at the end of surgery (ES) and after euthanasia (Eu).

The CYP21HA VGC in the liver of non-human primate number 1 (NHP01), number 2 (NHP02) and number 4 (NHP04), all injected in the right adrenal with ssAAV5-PGK-CYP21HA, was 11, 5 and 27, respectively, at the end of surgery. The CYP21HA VGC for the same animals at euthanasia was 0.3, 0.1 and 2, respectively. Immunofluorescence of the liver showed little expression of CYP21HA in these animals (FIG. 19).

Figure 10:
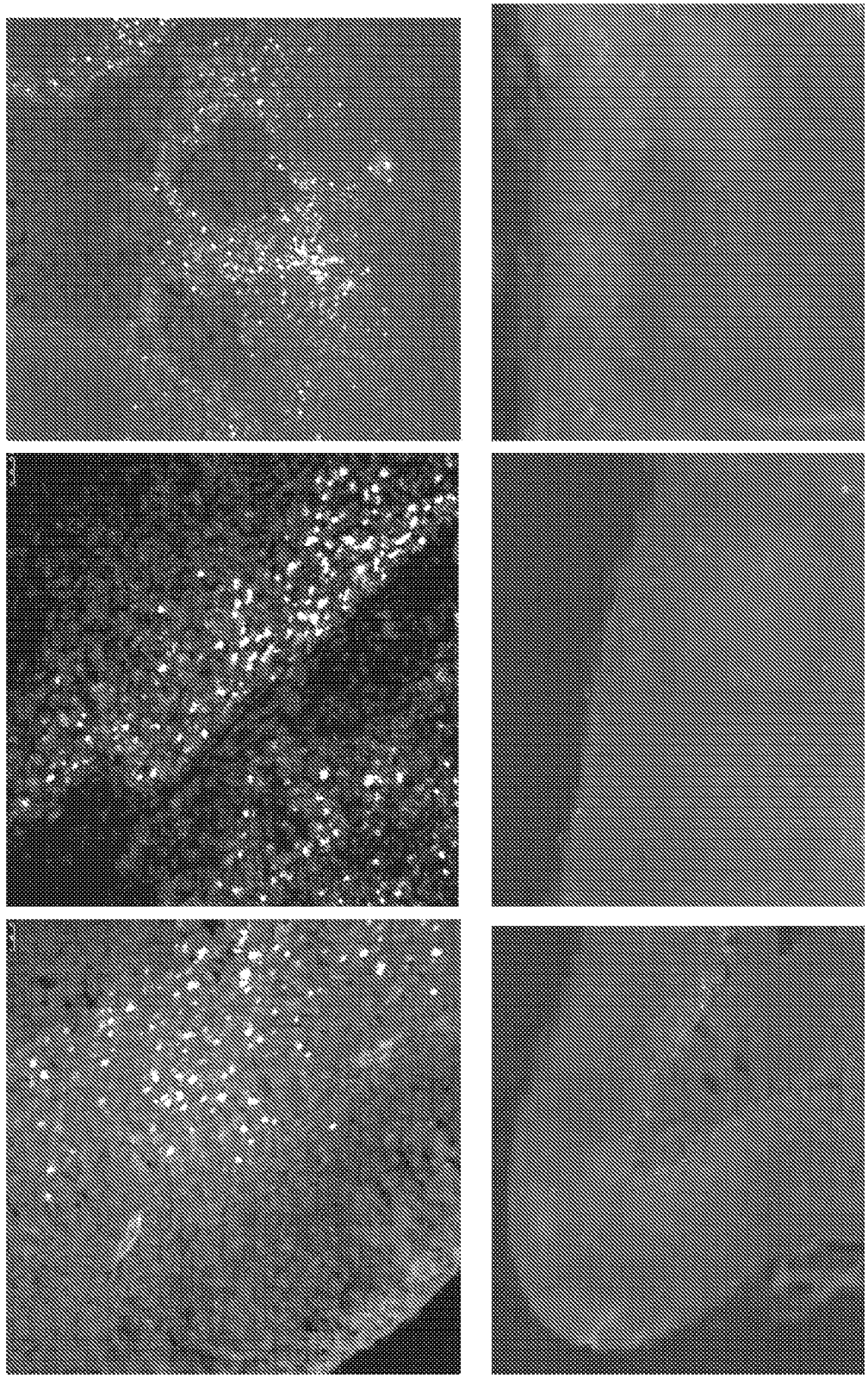
FIG. 10 shows GFP immunofluorescence images of the left adrenal gland of non-human primate number 1 (NHP01) injected with ssAAV5-PGK-GFP.
Figure 11:
FIG. 11 shows a GFP immunofluorescence image of an entire slice of the left adrenal of non-human primate number 1 (NHP01) injected with ssAAV5-PGK-GFP.
Figure 12:
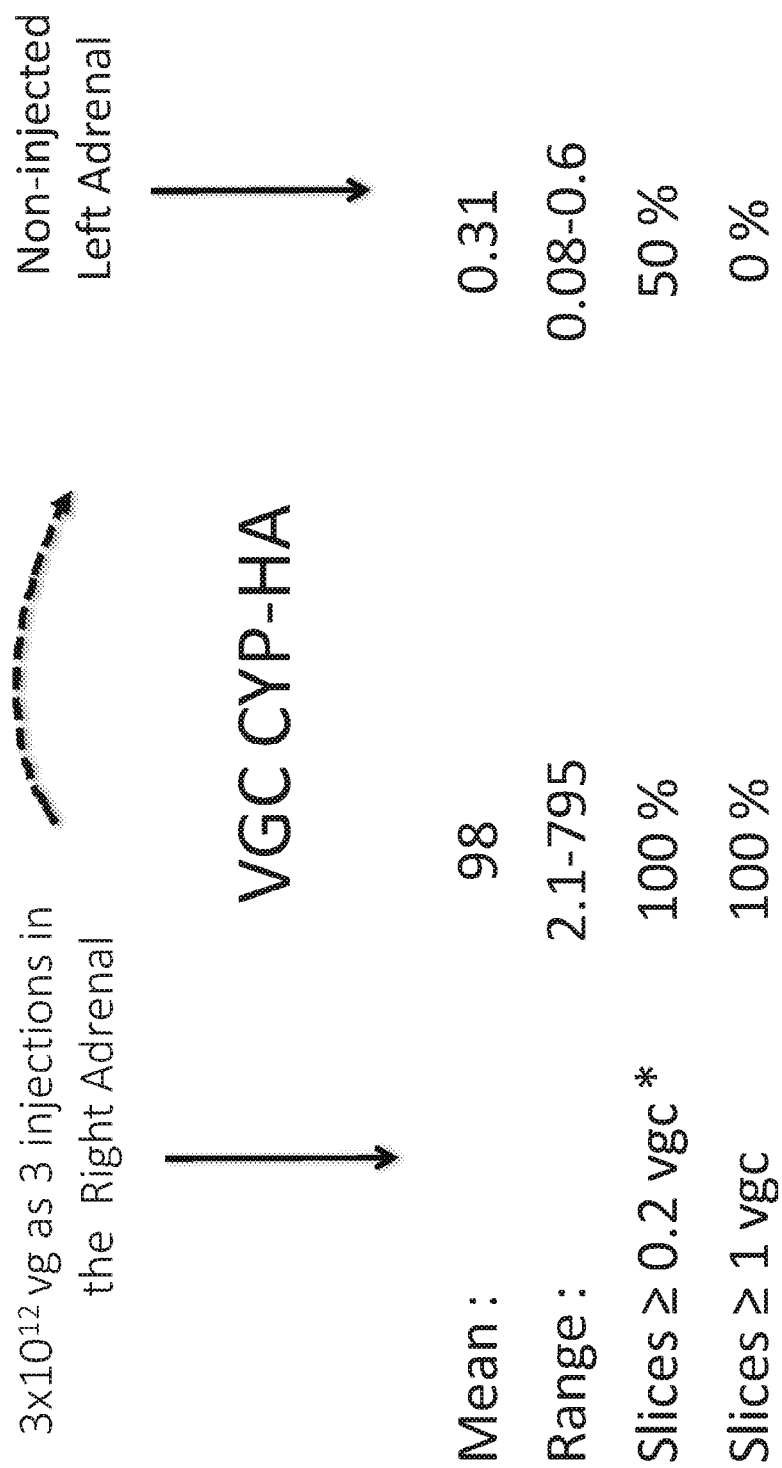
FIG. 12 shows CYP21HA viral genome copy (VGC) measurements for the adrenal glands of non-human primate number 1 (NHP01) injected with ssAAV5-PGK-CYP21HA in the right adrenal gland. VGC counts in both the right (injected) and left (non-injected) adrenals are shown. The asterisk indicates the VGC that was effective in treating Cyp21$^{-/-}$ mice in Examples 1-6.
Figure 13:
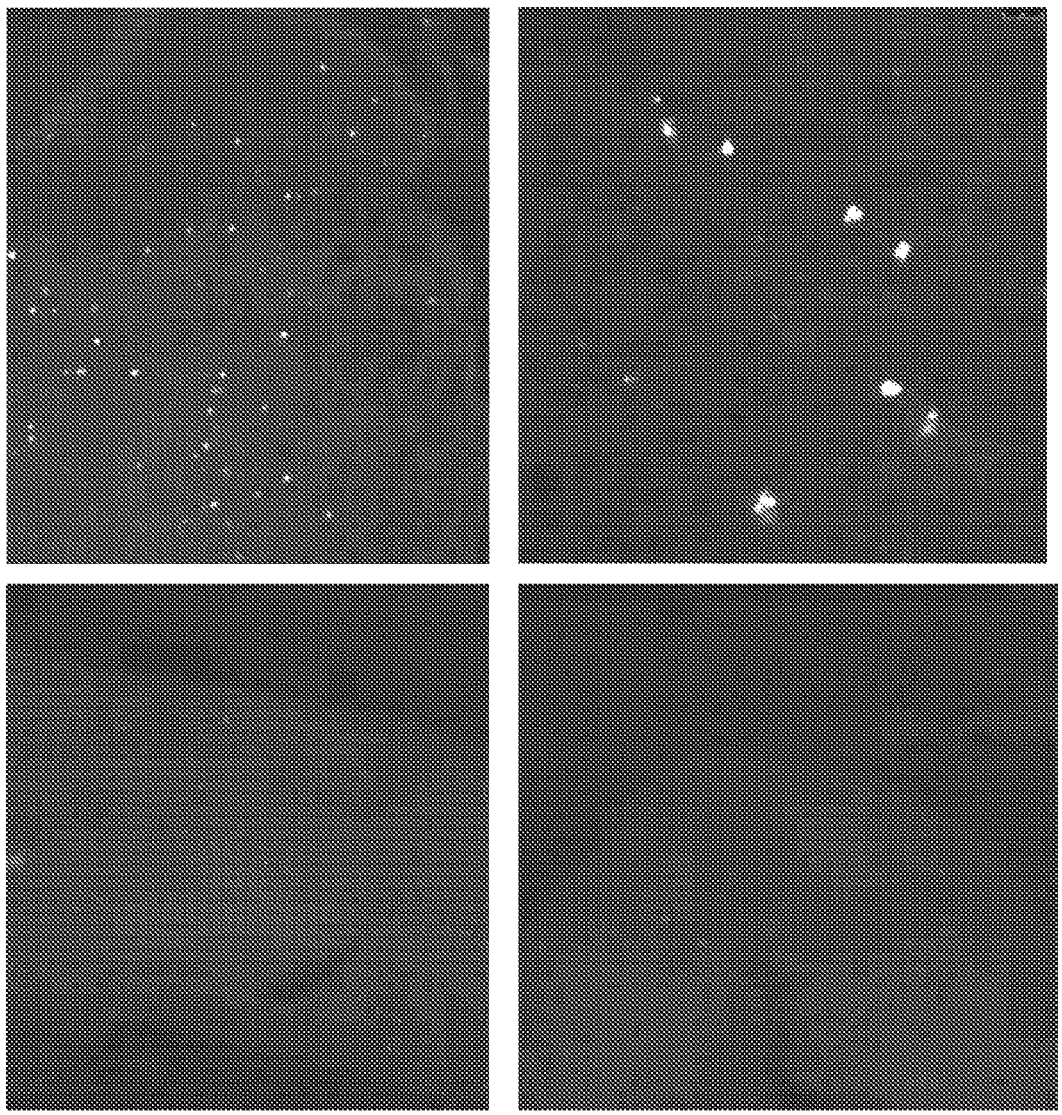
FIG. 13 shows HA immunofluorescence images of the right adrenal gland of non-human primate number 1 (NHP01) injected with ssAAV5-PGK-CYP21HA.
Figure 14:
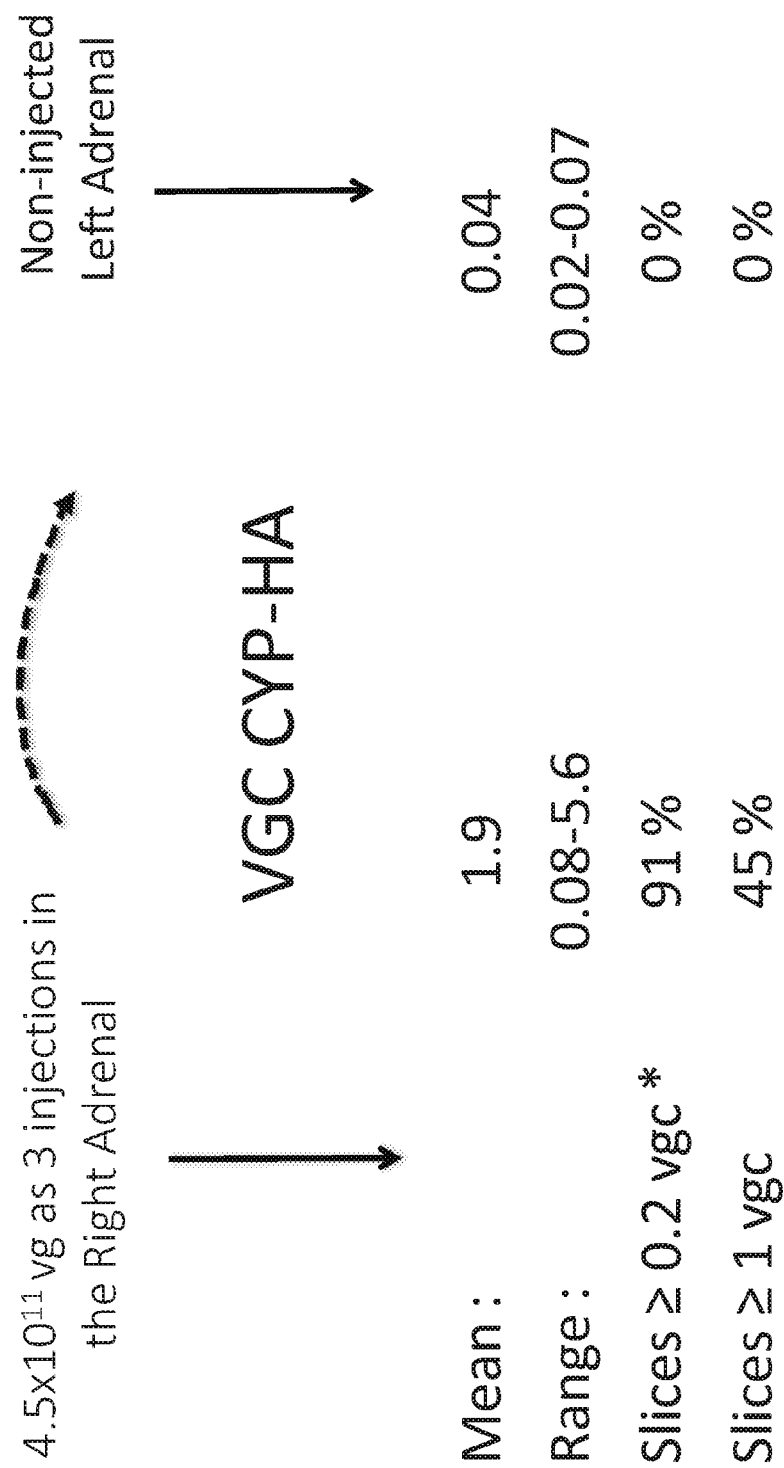
FIG. 14 shows CYP21HA viral genome copy (VGC) measurements for the adrenal glands of non-human primate number 2 (NHP02) injected with ssAAV5-PGK-CYP21HA in the right adrenal gland. VGC counts in both the right (injected) and left (non-injected) adrenals are shown. The asterisk indicates the VGC that was effective in treating Cyp21$^{-/-}$ mice in Examples 1-6. This animal was administered $4.5\times10^{11}$ vg as three injections in the right adrenal gland. This value was 6.6 times lower than that administered to NHP01.
Figure 15:
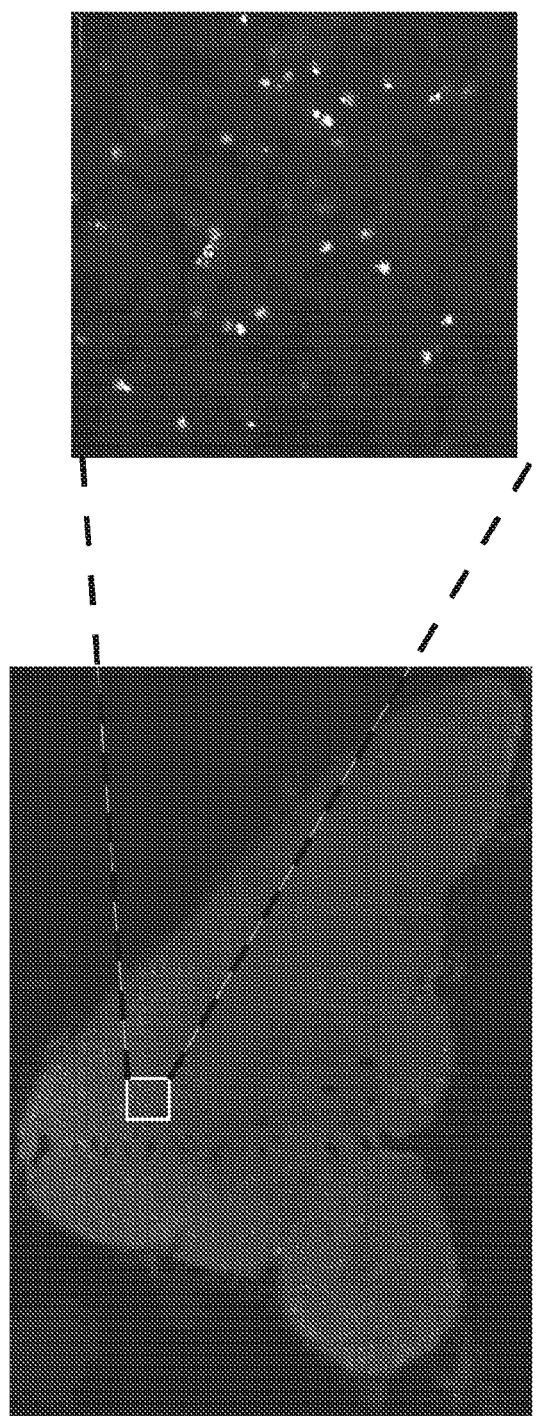
FIG. 15 shows HA immunofluorescence images in the right adrenal gland of non-human primate number 2 (NHP02) injected with ssAAV5-PGK-CYP21HA. This animal was administered $4.5\times10^{11}$ vg as three injections in the right adrenal gland. This value was 6.6 times lower than that administered to NHP01.
Figure 16:
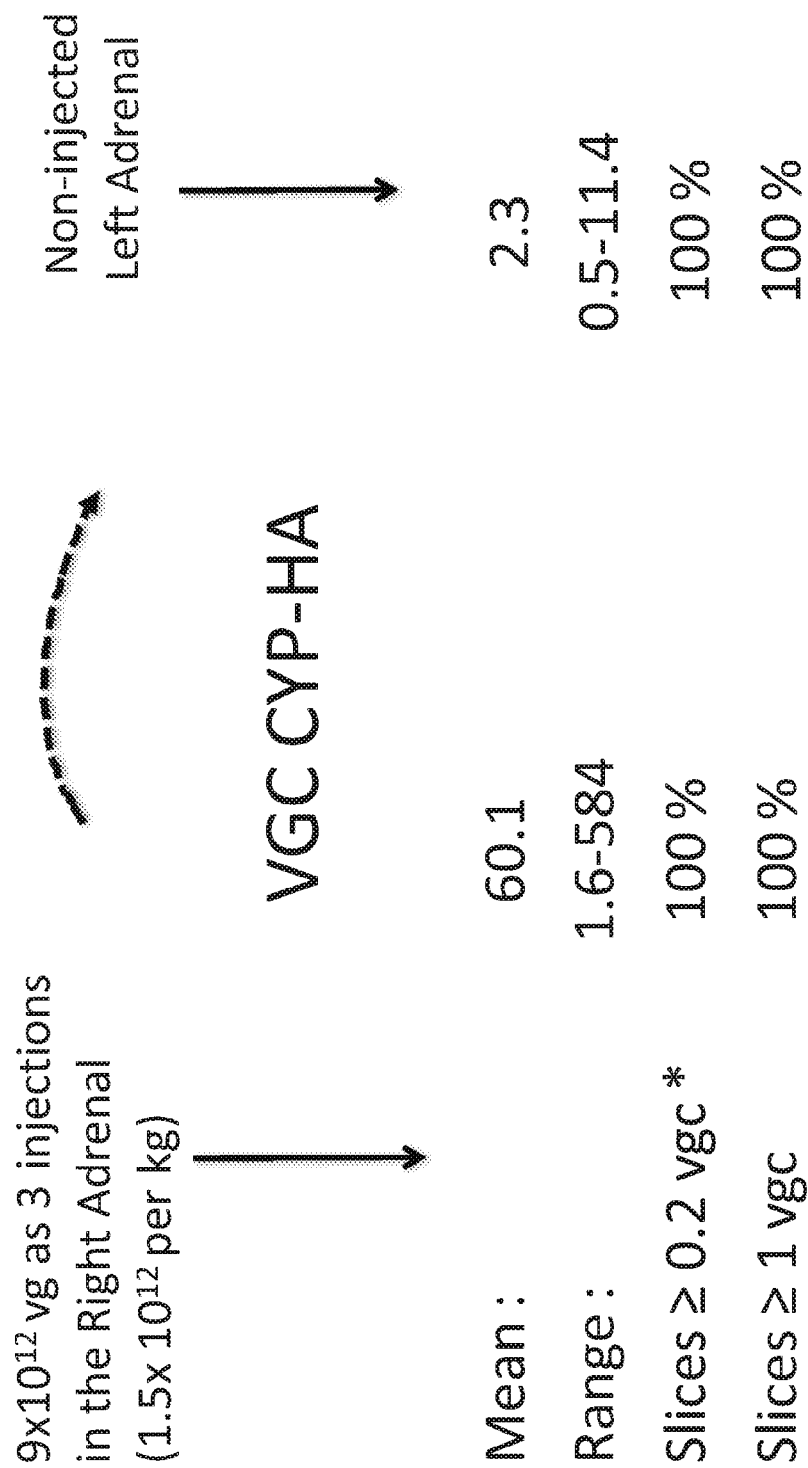
FIG. 16 shows CYP21HA viral genome copy (VGC) measurements for the adrenal glands of non-human primate number 4 (NHP04) injected with ssAAV5-PGK-CYP21HA in the right adrenal gland. VGC counts in both the right (injected) and left (non-injected) adrenals are shown. The asterisk indicates the VGC that was effective in treating Cyp21$^{-/-}$ mice in Examples 1-6.
Figure 17:
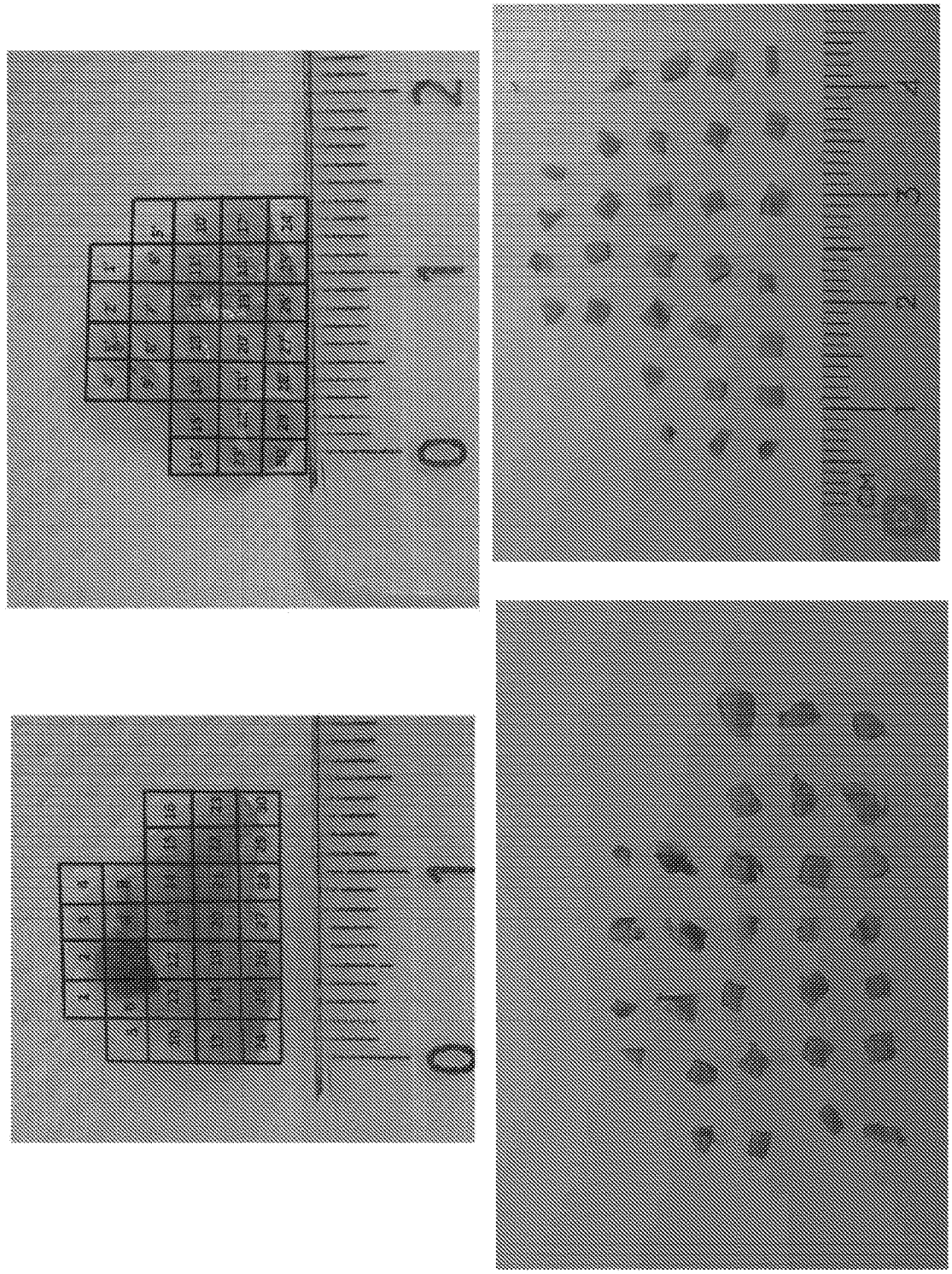
FIG. 17 shows a schematic and photographs of the dissection details of the right adrenal of non-human primate number 4 (NHP04) after injection with ssAAV5-PGK-CYP21HA in the right adrenal gland.

In NHPs, the AAV5 capsid allowed good transduction of GFP copies (VGC 1.2, Table 4), a lot of CYP21HA copies in the injected adrenal (1.9-98, Table 4), a good number of CYP21HA copies in the non-injected adrenal (0.04-2.3), and few copies in the liver. For the same injected dose, a lot of CYP21HA copies were counted compared to GFP copies. GFP expression (IF) was patchy in the injected adrenal (FIGS. 10 and 11). Some CYP21HA expression (IF) was visualized in the injected adrenal (FIGS. 13 and 15).

Figure 20:
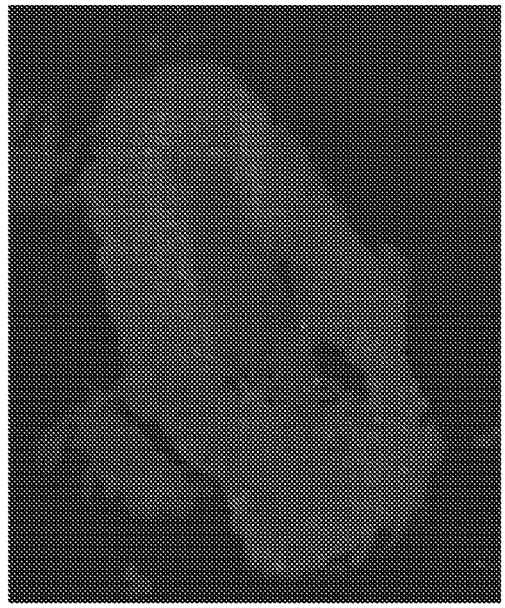
FIG. 20 shows GFP viral genome copy (VGC) measurements for adrenal glands of wild-type mice that were administered ssAAV5-PGK-GFP intravenously. The asterisk indicates the VGC that was effective in treating Cyp21$^{-/-}$ mice in Examples 1-6.
Figure 21:
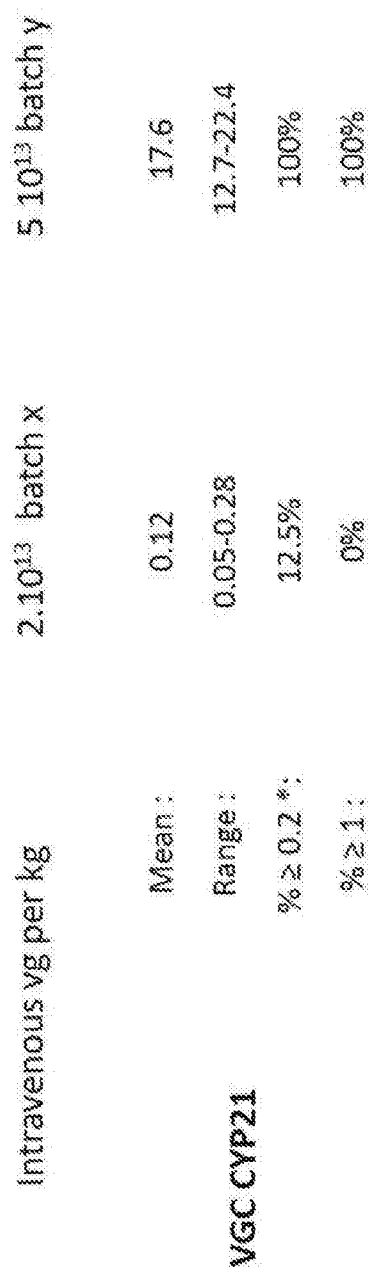
FIG. 21 shows CYP21HA viral genome copy (VGC) measurements for adrenal glands of wild-type mice that were administered ssAAV5-PGK-CYP21HA intravenously. The asterisk indicates the VGC that was effective in treating Cyp21$^{-/-}$ mice in Examples 1-6.
Figure 22:
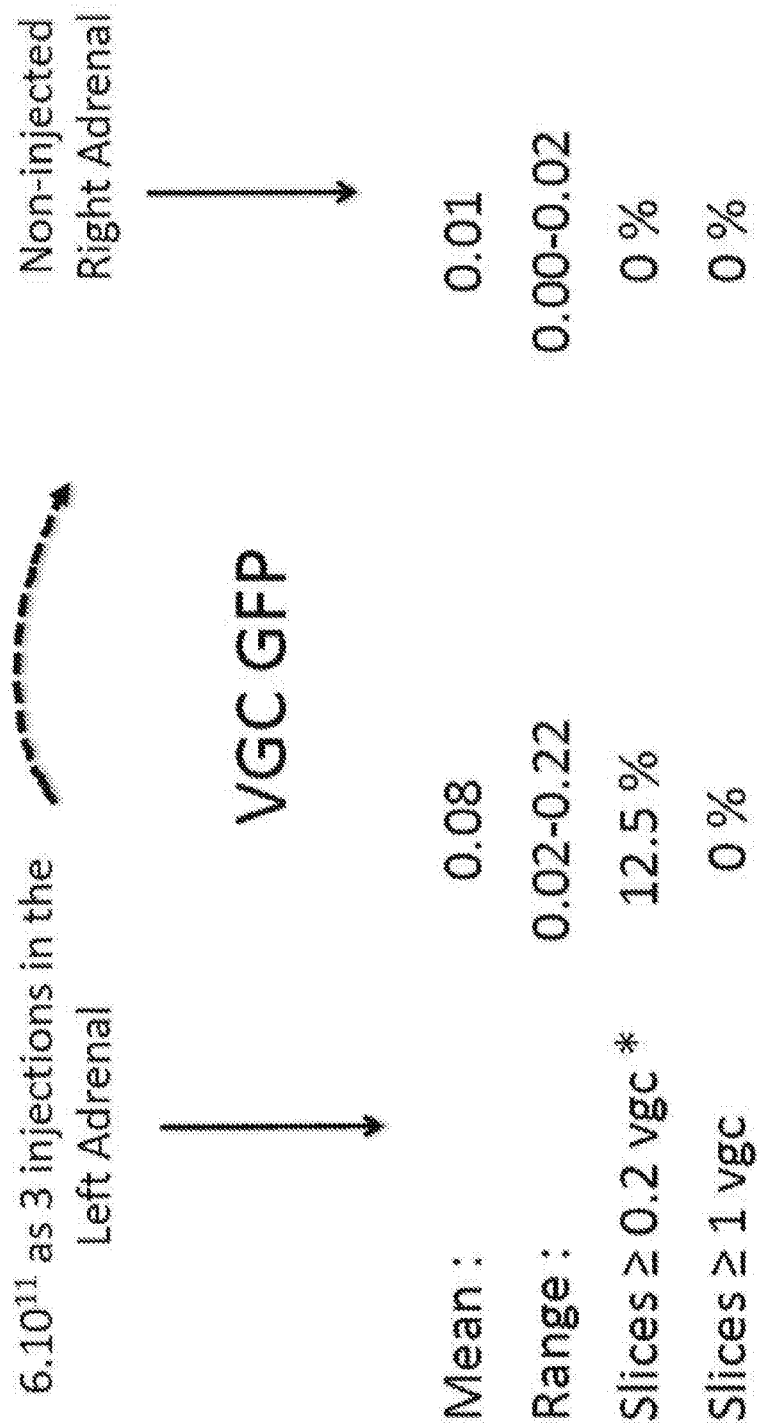
FIG. 22 shows GFP viral genome copy (VGC) measurements for the adrenal glands of non-human primate number 2 (NHP02) injected with ssAAV6-CAG-GFP in the left adrenal gland. VGC counts in both the right (non-injected) and left (injected) adrenals are shown. The asterisk indicates the VGC that was effective in treating Cyp21$^{-/-}$ mice in Examples 1-6.

In wild-type mice, the AAV5 capsid allowed good intravenous transduction of GFP copies that seemed proportional to vg dose (VGC 0.2-16.6, Table 4), and good transduction of CYP21HA (VGC 012-17.6, Table 4). GFP expression (IF) was weak in adrenals of wild-type mice (FIG. 20). CYP21HA expression (IF) was non interpretable because of a technical antibody problem.

Example 8: Studies with AAV6-CAG rAAV

A ssAAV6-CAG-GFP vector was produced. This vector contains a genome with AAV2 ITR sequences and encodes AAV6 capsid proteins. This rAAV was administered to wild-type mice (B6) intravenously (i.v.) and to two non-human primates (NHP) (*Macaca fascicularis*) via intra-adrenal injection as shown in Table 5.

TABLE 5

Administration of AAV6-CAG rAAV.

| Vector | Dose per animal (vg) | Route | NHP or mice | Lot no. |
|---|---|---|---|---|
| ssAAV6-CAG-GFP | $6 \times 10^{11}$ | Intra-adrenal (left adrenal) | NHP02 | GVPN#6485 |

TABLE 5-continued

Administration of AAV6-CAG rAAV.

| Vector | Dose per animal (vg) | Route | NHP or mice | Lot no. |
|---|---|---|---|---|
| ssAAV6-CAG-GFP | $2.2 \times 10^{12}$ | Intra-adrenal (left adrenal) | NHP04 | GVPN#6485 |
| ssAAV6-CAG-GFP | $1.5 \times 10^{12}$ | i.v. ($5 \times 10^{13}$/kg) | Mice | GVPN#6485 |

GFP vector genome copy (VGC) values were determined for the animals treated with the rAAV (Table 6; FIGS. 22, 26-29, 31 and 41) at 3 weeks post-treatment. GFP expression was also visualized by immunofluorescence (IF) (FIGS. 23-25 and 29-32) at 3 weeks post-treatment.

TABLE 6

Effects of AAV6-CAG rAAV.

| Vector | Dose per animal (vg) | Route | NHP or mice | Mean VGC in the injected adrenal (if intra-adrenal) |
|---|---|---|---|---|
| SSAAV6-CAG-GFP | $6 \times 10^{11}$ | Intra-adrenal (left adrenal) | NHP02 | 0.08 |
| SSAAV6-CAG-GFP | $2.2 \times 10^{12}$ | Intra-adrenal (left adrenal) | NHP04 | 0.84 |
| ssAAV6-CAG-GFP | $1.5 \times 10^{12}$ | i.v. ($5 \times 10^{13}$/kg) | Mice | 62.4 |

Figure 29:
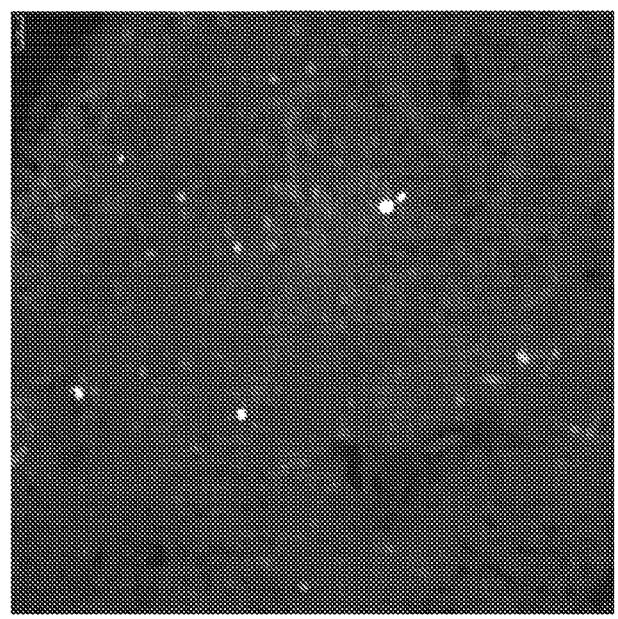
FIG. 29 shows mean GFP viral genome copy (VGC) measurements in the livers of NHP02 and NHP04 injected with ssAAV6-CAG-GFP at the end of surgery (ES) and after euthanasia (Eu).
Figure 30:
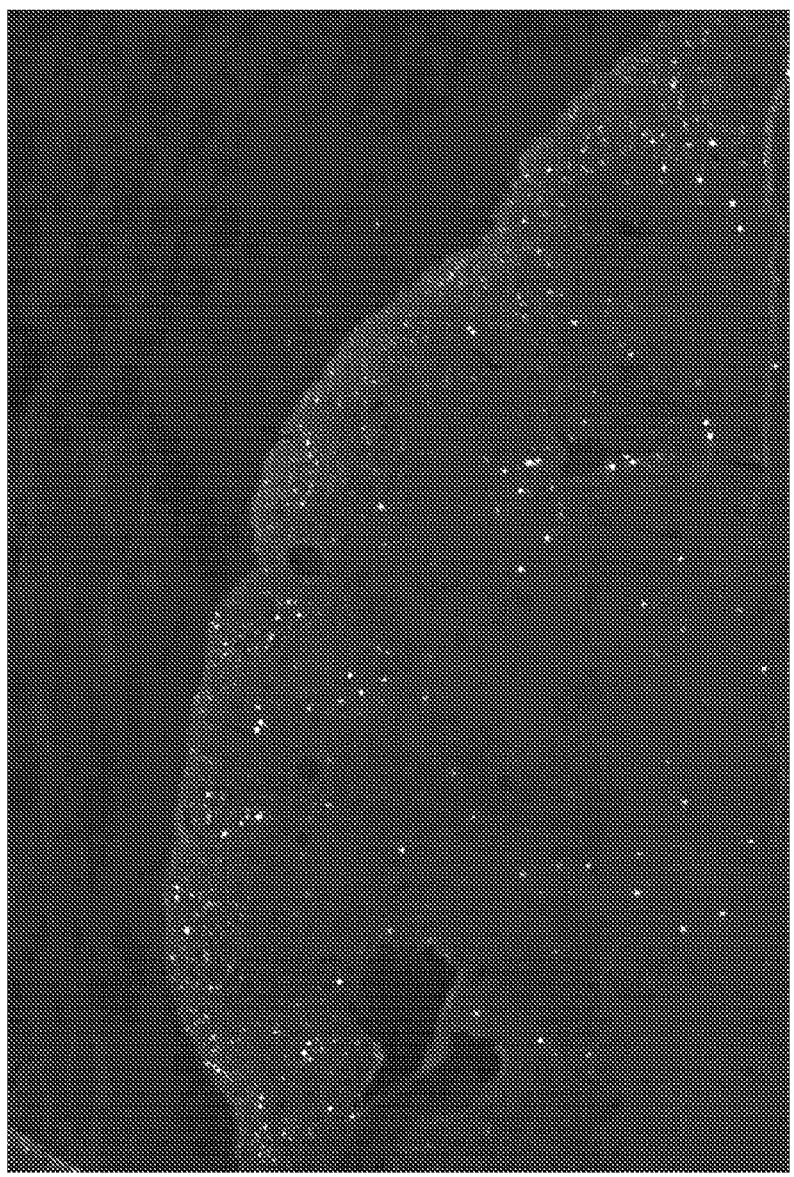
FIG. 30 shows another GFP immunofluorescence image of the liver of NHP04 injected with ssAAV6-CAG-GFP in the left adrenal.
Figure 31:
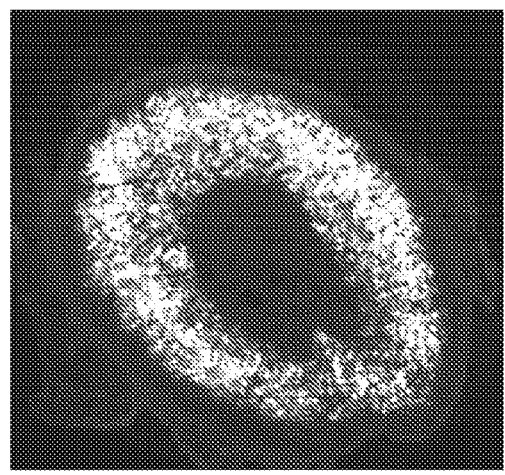
FIG. 31 shows GFP viral genome copy (VGC) measurements for adrenal glands of wild-type mice that were administered ssAAV6-CAG-GFP intravenously.

The GFP VGC in the liver of non-human primate number 2 (NHP02) and number 4 (NHP04) injected with ssAAV6-CAG-GFP in the left adrenal was 10.3 and 10, respectively, at the end of surgery. The GFP VGC for the same animals at euthanasia was 0.8 and 3.5, respectively. Immunofluorescence of the liver showed little expression of GFP in these animals (FIGS. 29 and 30).

Figure 23:
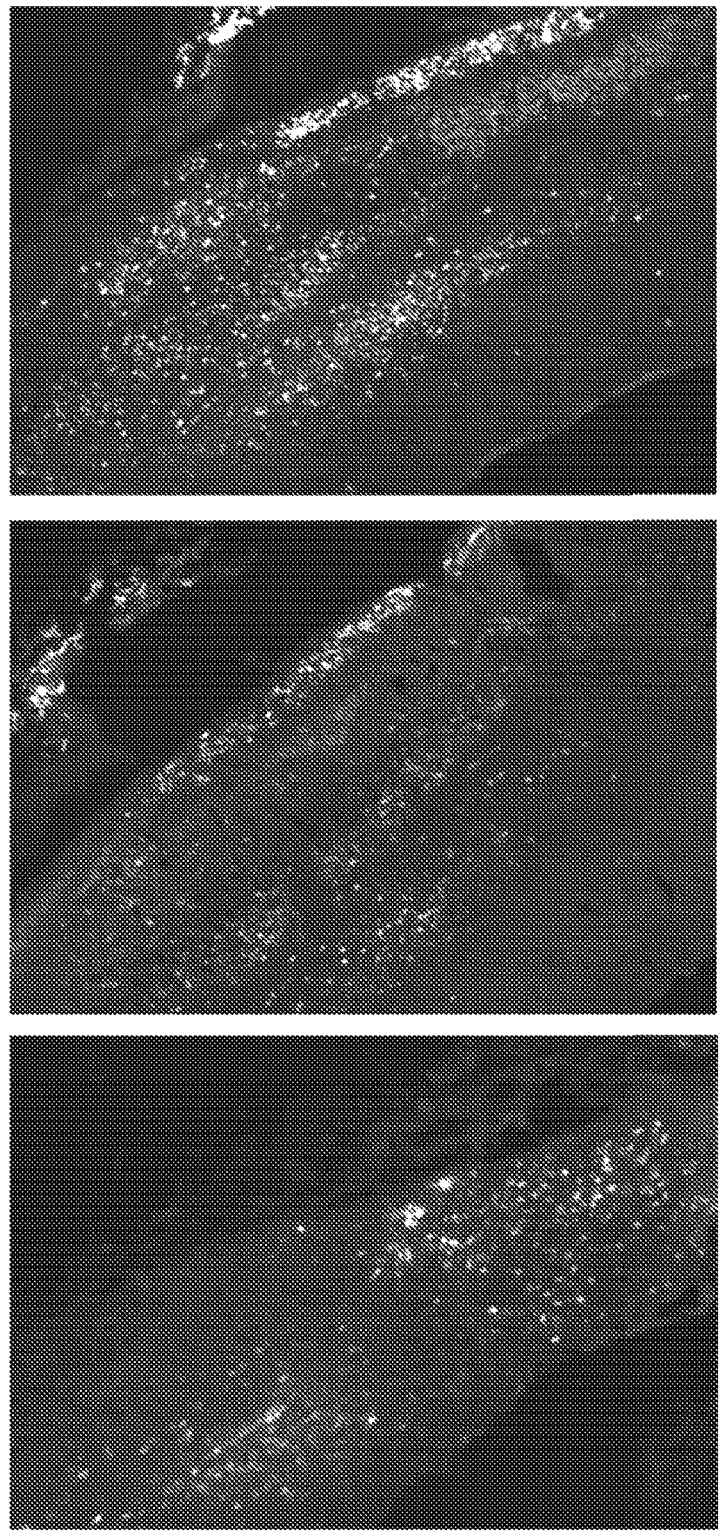
FIG. 23 shows GFP immunofluorescence images of the left adrenal gland of non-human primate number 2 (NHP02) injected with ssAAV6-CAG-GFP.
Figure 24:
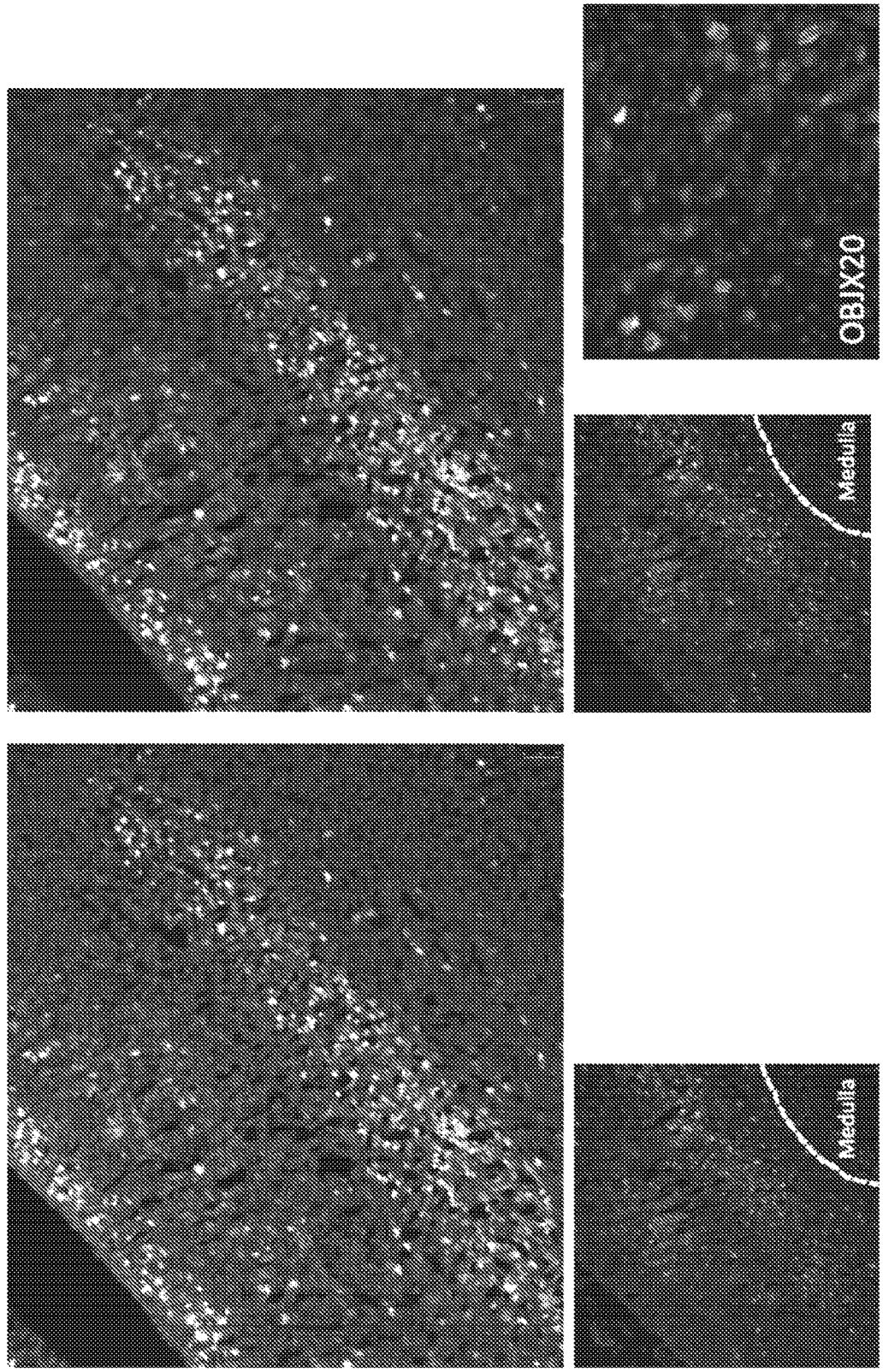
FIG. 24 shows selected positive GFP immunofluorescence images in the left adrenal gland of non-human primate number 2 (NHP02) injected with ssAAV6-CAG-GFP. "OBJX20" refers to magnification×20.
Figure 25:
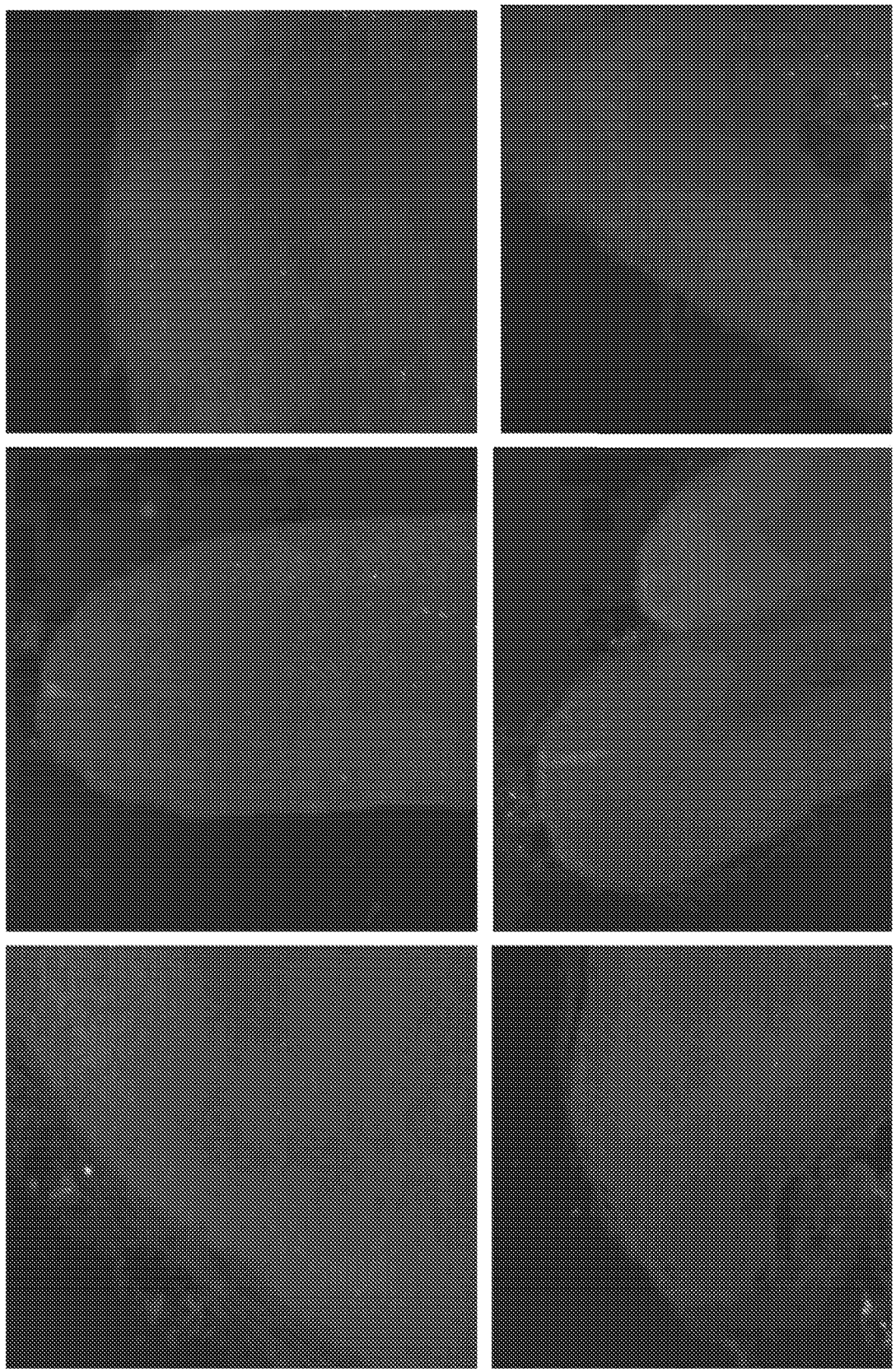
FIG. 25 shows GFP immunofluorescence images of the left adrenal of NHP02 injected with ssAAV6-CAG-GFP. This figure shows the unequal distribution of the immunofluorescence signal across pieces of the adrenal gland.
Figure 26:
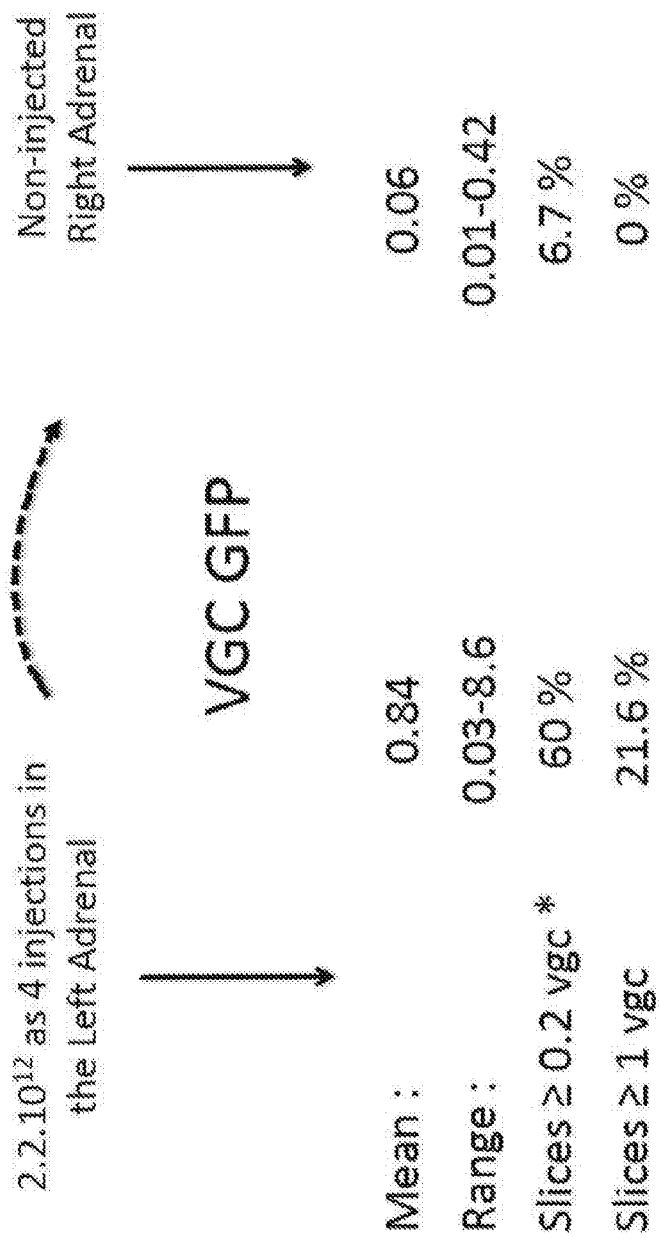
FIG. 26 shows GFP viral genome copy (VGC) measurements for the adrenal glands of non-human primate number 4 (NHP04) injected with ssAAV6-CAG-GFP in the left adrenal gland. VGC counts in both the right (non-injected) and left (injected) adrenals are shown. The asterisk indicates the VGC that was effective in treating Cyp21$^{-/-}$ mice in Examples 1-6.

In NHPs, the AAV6 capsid led to few GFP copies (VGC 0.08-0.84, Table 6) in the injected adrenal, and few copies in the liver. GFP expression (IF) was patchy in the injected adrenal (FIGS. 23-25).

Figure 32:
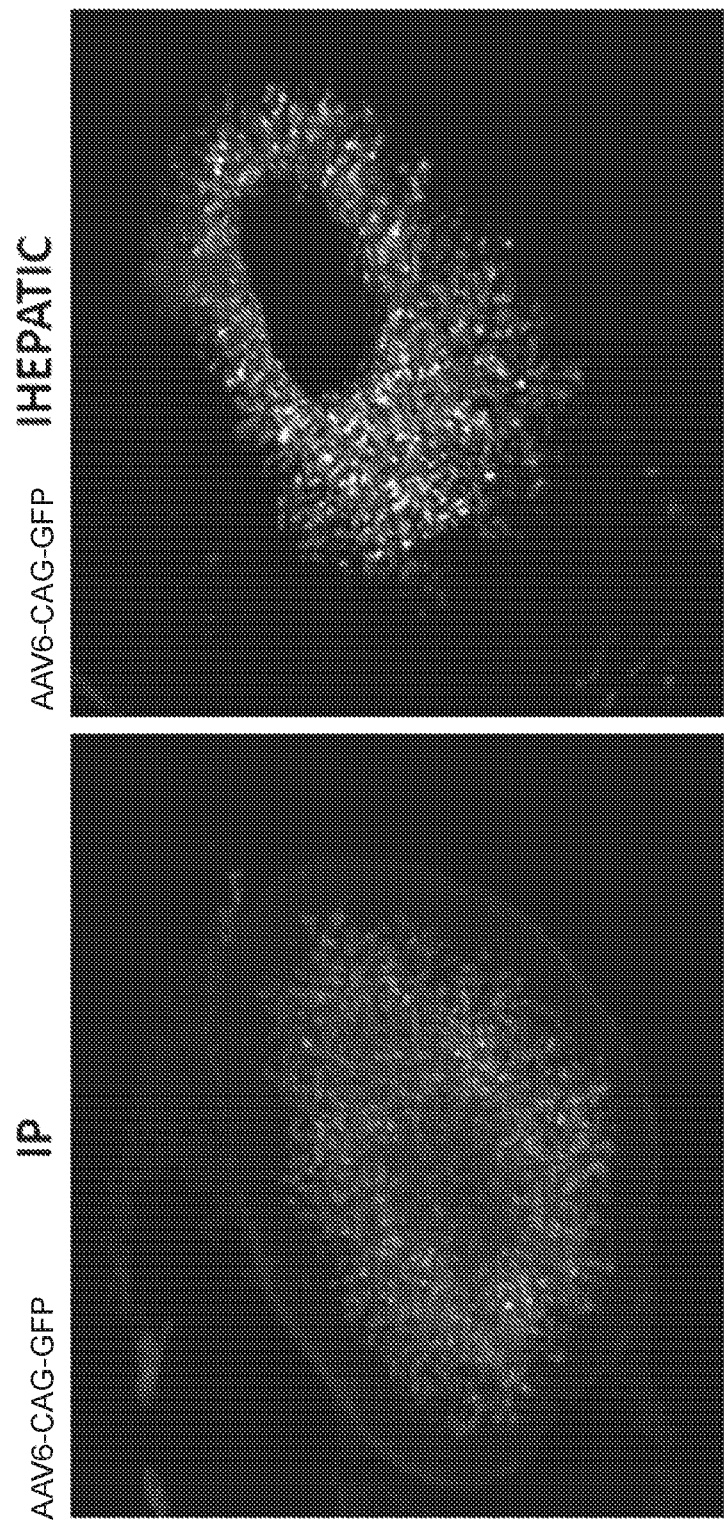
FIG. 32 shows GFP immunofluorescence images of wild-type mouse adrenal glands treated with ssAAV6-CAG-GFP either by IP (intraperitoneal) or IH (intra-hepatic) injections.
Figure 33:
FIG. 33 shows GFP viral genome copy (VGC) measurements for the adrenal glands of non-human primate number 3 (NHP03) injected with ssAAV1-CB6-GFP in the left adrenal gland. VGC counts in both the right (non-injected) and left (injected) adrenals are shown. The asterisk indicates the VGC that was effective in treating Cyp21$^{-/-}$ mice in Examples 1-6.
Figure 34:
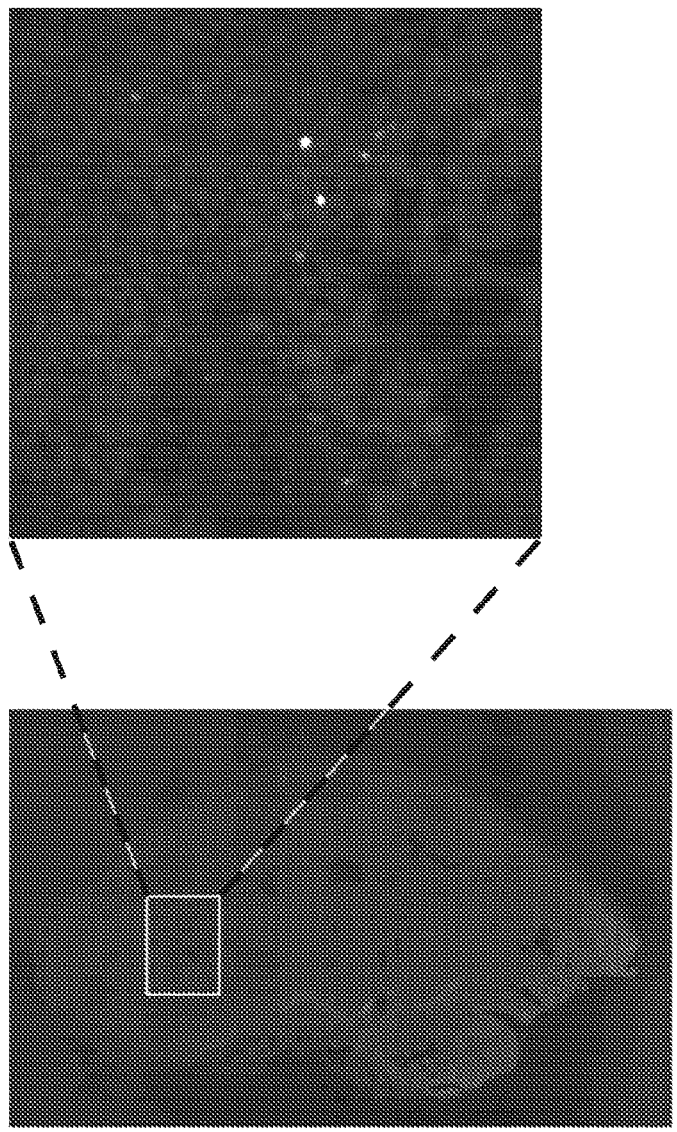
FIG. 34 shows GFP immunofluorescence images of the left adrenal gland of non-human primate number 3 (NHP03) injected with ssAAV1-CB6-GFP.

In wild-type mice, the AAV6 capsid allowed excellent intravenous transduction of GFP copies (VGC 62.4, Table 6). GFP expression (IF) was excellent in adrenals of wild-type mice after intravenous injection (FIG. 31), intraperitoneal injection (FIG. 32) and intra-hepatic injection (FIG. 32).

Example 9: Studies with AAV1-CB6 and AAV1-PGK rAAV

A ssAAV1-CB6-GFP vector and a ssAAV1-PGK-CYP21HA vector were produced. These vectors contain a genome with AAV2 ITR sequences and encode AAV1 capsid proteins. These rAAVs were administered to wild-type mice (B6) intravenously (i.v.) and to one non-human primate (NHP) (*Macaca fascicularis*) via intra-adrenal injection as shown in Table 7.

TABLE 7

Administration of AAV1 rAAV.

| Vector | Dose per animal (vg) | Route | NHP or mice | Lot no. |
|---|---|---|---|---|
| ssAAV1-CB6-GFP | $3 \times 10^{12}$ | Intra-adrenal (left adrenal) | NHP03 | VCAV-044116 |
| SSAAV1-CB6-GFP | $1.5 \times 10^{12}$ | i.v. ($5 \times 10^{13}$/kg) | Mice | VCAV-044116 |
| SSAAV1-PGK-CYP21HA | $2.2 \times 10^{12}$ | Intra-adrenal (right adrenal) | NHP03 | GVPN#6617 |
| ssAAV1-PGK-CYP21HA | $3 \times 10^{12}$ | i.v. ($1 \times 10^{14}$/kg) | Mice | GVPN#6617 |

GFP or CYP21HA vector genome copy (VGC) values were determined for the animals treated with the rAAV (Table 8; FIGS. 33, 35-37 and 39-41) at 3 weeks post-treatment. GFP and HA expression was also visualized by immunofluorescence (IF) (FIGS. 34-36, 38 and 39) at 3 weeks post-treatment.

TABLE 8

Effects of AAV1 rAAV.

| Vector | Dose per animal (vg) | Route | NHP or mice | Mean VGC in the injected adrenal (if intra-adrenal) |
|---|---|---|---|---|
| SSAAV1-CB6-GFP | $3 \times 10^{12}$ | Intra-adrenal (left adrenal) | NHP03 | 0.56 |
| ssAAV1-CB6-GFP | $1.5 \times 10^{12}$ | i.v. ($5 \times 10^{13}$/kg) | Mice | 81 |
| SSAAV1-PGK-CYP21HA | $2.2 \times 10^{12}$ | Intra-adrenal (right adrenal) | NHP03 | 1.05 |
| SSAAV1-PGK-CYP21HA | $3 \times 10^{12}$ | i.v. ($1 \times 10^{14}$/kg) | Mice | 220 |

Figure 35:
FIG. 35 shows mean GFP viral genome copy (VGC) measurements for ssAAV1-CB6-GFP in the liver of NHP03 at the end of surgery (ES) and after euthanasia (Eu).

The GFP VGC in the liver of non-human primate number 3 (NHP03) injected with ssAAV1-CB6-GFP in the left adrenal was 0.02 at the end of surgery, and 0.9 at euthanasia. Immunofluorescence of the liver did not show any expression of GFP in this animal (FIG. 35).

Figures 39, 40:
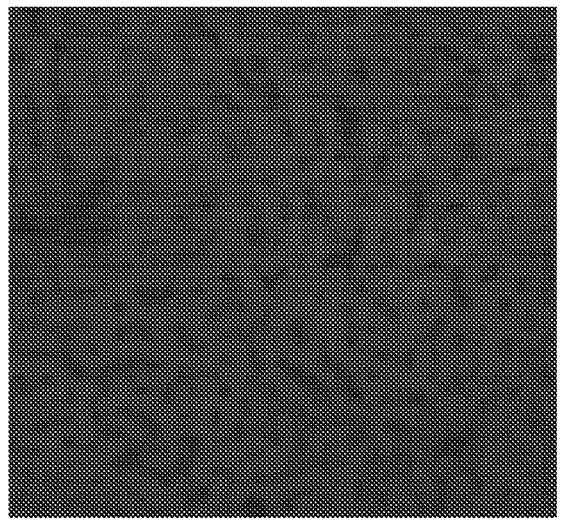
FIG. 39 shows CYP21HA mean viral genome copy (VGC) measurements in the liver of NHP03 injected with ssAAV1-PGK-CYP21HA in the right adrenal at the end of surgery (ES) and after euthanasia (Eu).
FIG. 40 shows CYP21HA viral genome copy (VGC) measurements for adrenal glands of wild-type mice that were administered $1 \times 10^{14}$ vg/kg ssAAV1-PGK-CYP21HA intravenously.
Figure 41A:
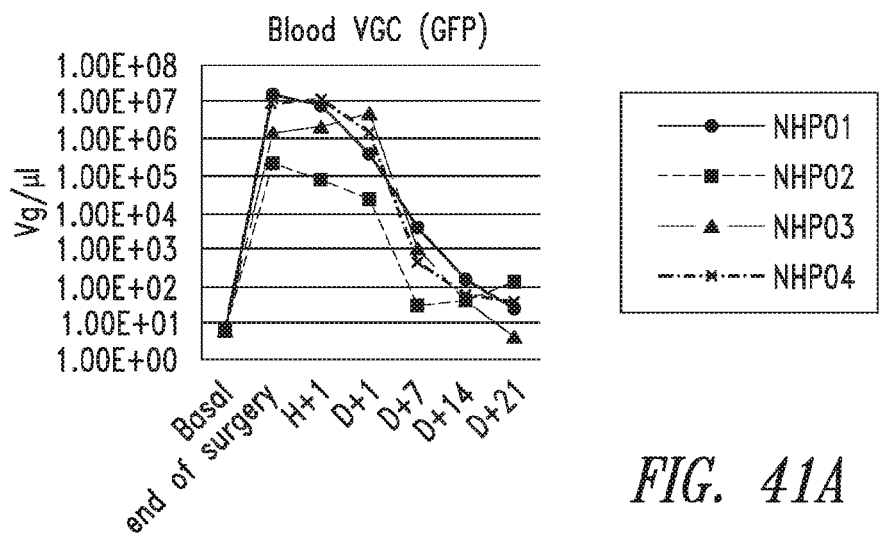
FIG. 41A and FIG. 41B show line graphs summarizing measurements of blood VGC of GFP (FIG. 41A) and hCYP21HA (FIG. 41B) in NHP01, NHP02, NHP03 and NHP04 at various time points.
Figure 41C:
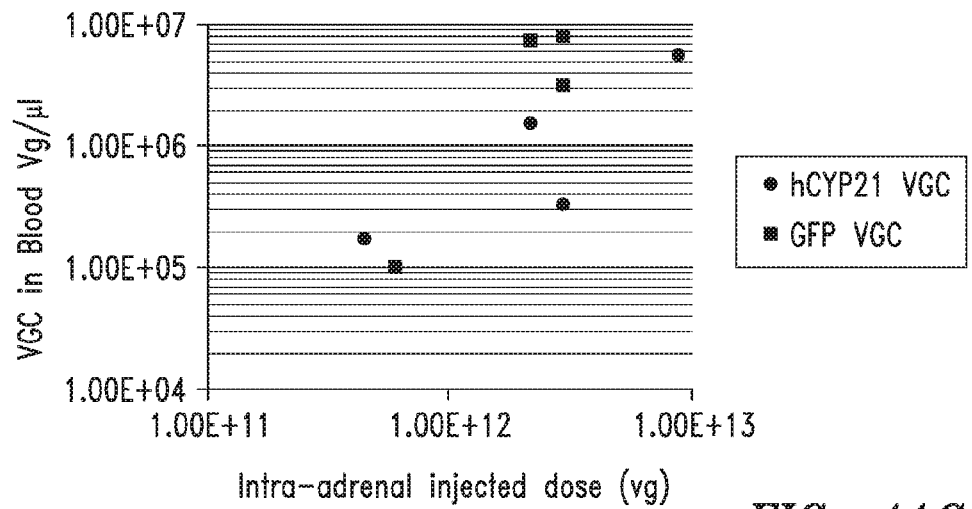
FIG. 41C shows a graph summarizing blood VGC at the end of surgery as a function of intra-adrenal injected dose. vg=viral genomes. "H+1"
stands for 1 hour post injection. "D+1", "D+7", "D+14" and "D+21" stand for 1 day, 7 days, 14 days and 21 days, respectively, post injection.
Figure 41B:
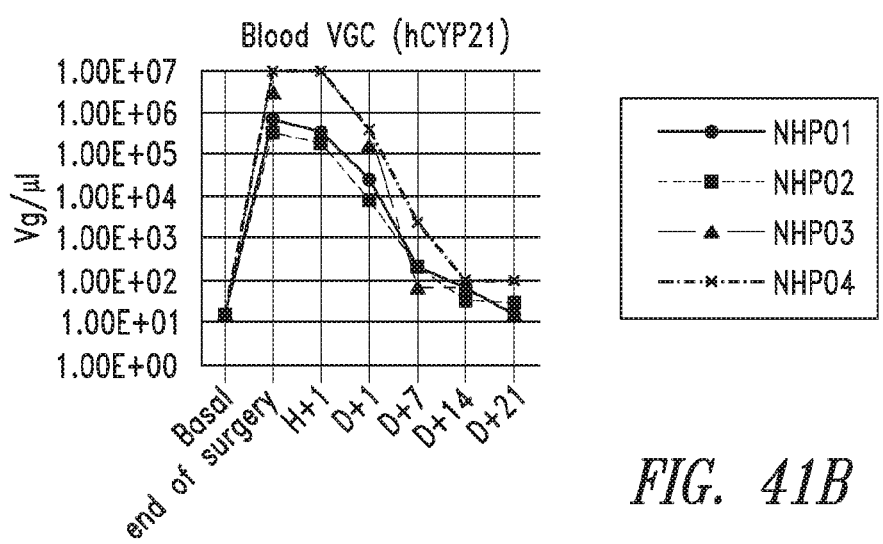

The CYP21HA VGC in the liver of non-human primate number 3 (NHP03) injected with ssAAV1-PGK-CYP21HA in the right adrenal was 1.5 at the end of surgery, and 2.9 at euthanasia. Immunofluorescence of the liver did not show any expression of CYP21HA in this animal (FIG. 39).

Figure 38:
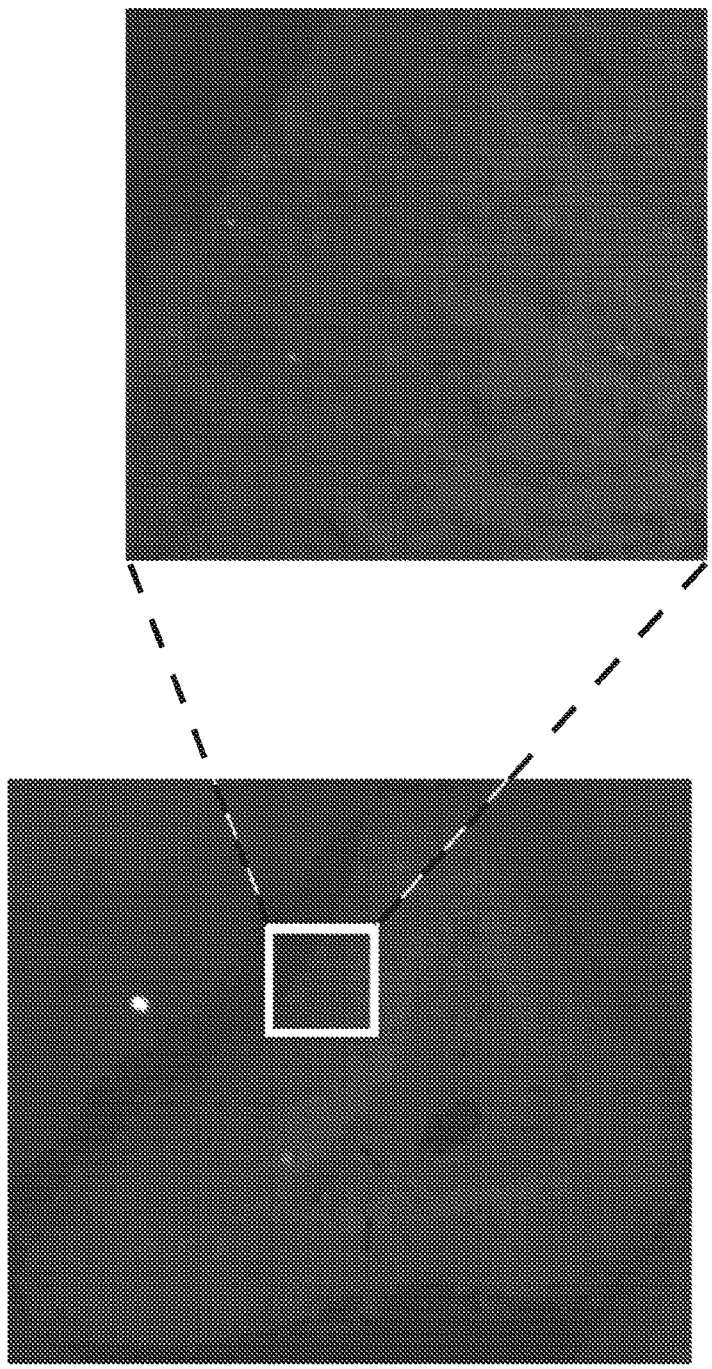
FIG. 38 shows HA immunofluorescence images of the right adrenal gland of non-human primate number 3 (NHP03) injected with ssAAV1-PGK-CYP21HA. The animal was administered $2.2 \times 10^{12}$ as two injections in the right adrenal.

In NHPs, the AAV1 capsid led to few GFP copies (VGC 0.56, Table 8) in the injected adrenal, and few CYP21HA copies (VGC 1.05, Table 8), but surprisingly 0.48 CYP21HA VGC in the non-injected adrenal. Very few adrenal cells were positive for GFP expression (IF) (FIG. 34) or CYP21HA expression (FIG. 38).

Figure 36:
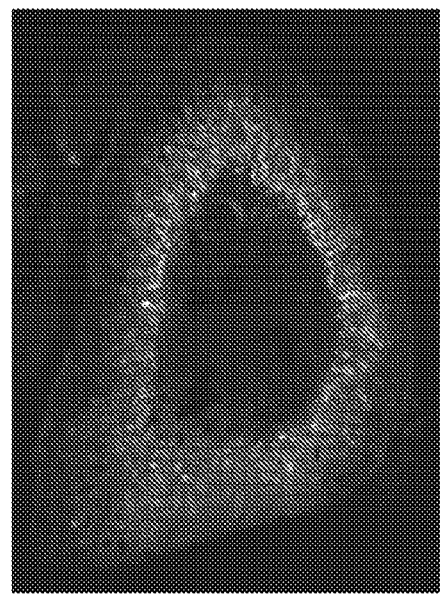
FIG. 36 shows GFP viral genome copy (VGC) measurements for adrenal glands of wild-type mice that were administered ssAAV1-CB6-GFP intravenously.
Figure 37:
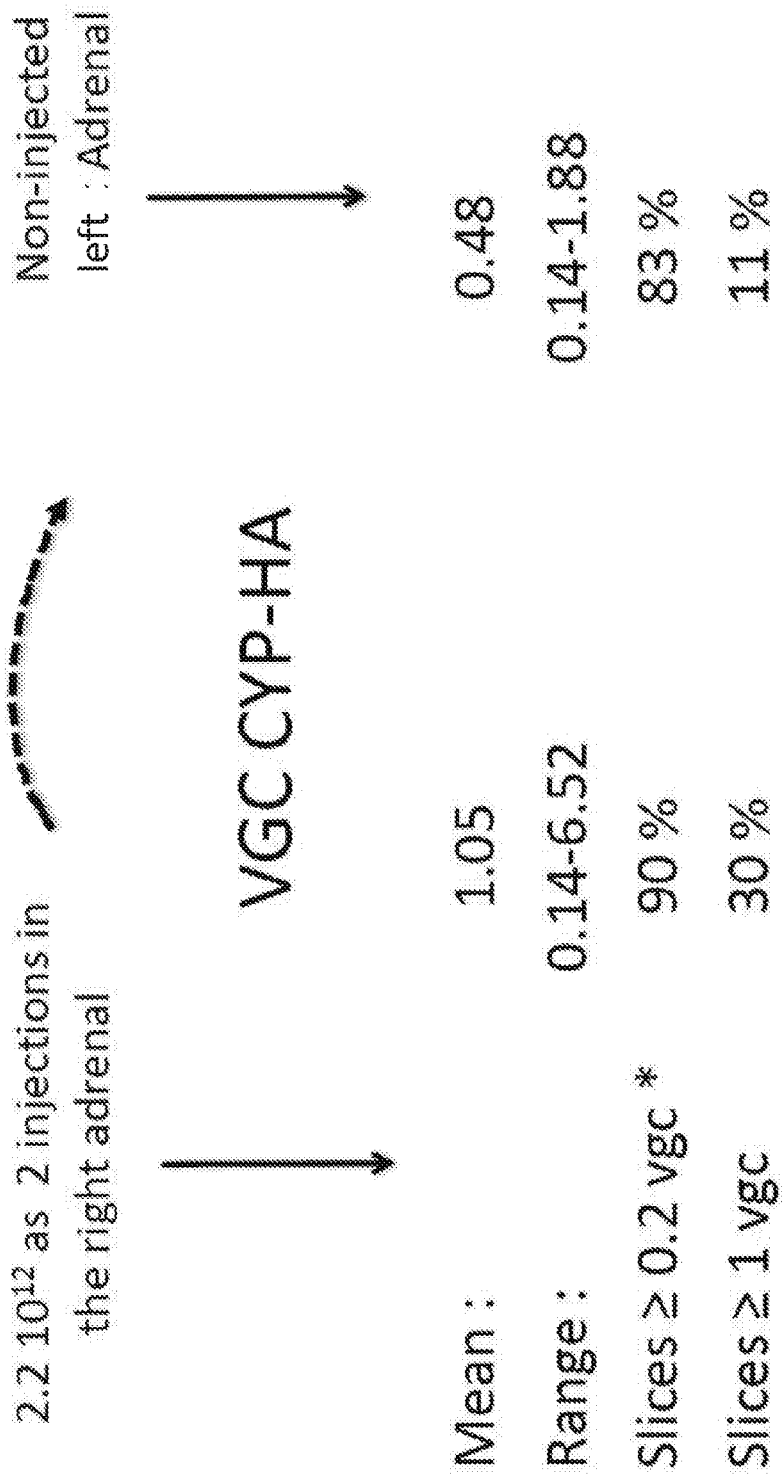
FIG. 37 shows CYP21HA viral genome copy (VGC) measurements for the adrenal glands of non-human primate number 3 (NHP03) injected with ssAAV1-PGK-CYP21HA in the right adrenal gland. VGC counts in both the right (injected) and left (non-injected) adrenals are shown. The asterisk indicates the VGC that was effective in treating Cyp21$^{-/-}$ mice in Examples 1-6.

In wild-type mice, the AAV1 capsid allowed excellent intravenous transduction of GFP copies (VGC 81, Table 8) and excellent GFP expression (IF) (FIG. 36). In wild-type mice, the AAV1 capsid allowed excellent intravenous transduction of CYP21HA copies (VGC 220, Table 8).

Example 10: Measurements of rAAV Expression in Mouse Gonads

GFP or CYP21HA VGC was measured in mouse gonads and adrenal glands 3 weeks after administration of AAV6-CAG-GFP, AAV1-CB6-GFP or AAV5-PGK-CYPHA. Results are shown in Table 9. Gonads showed significant but much lower VGC content than adrenals, depending on the vector used.

TABLE 9

VGC in mouse gonads and adrenal glands after administration of rAAV.

|  | AAV6-CAG-GFP | AAV1-CB6-GFP | AAV5-PGK-CYPHA |
|---|---|---|---|
| VGC Testes | 0.27 | 0.41 | 1.86 |
| VGC Ovaries | 0.07 | 1.31 | 0.82 |
| VGC Adrenal | 62.4 | 81 | 17.6 |

TABLE 10

Non-limiting examples of 21OH (CYP21A2) and promoter sequences.

| Sequence description | Sequence | SEQ ID NO |
|---|---|---|
| CYP21A2, Homo sapiens, NCBI Reference Sequence NP_000491.4 | MLLLGLLLLLPLLAGARLLWNWWKLRSLHLPPLAPGFLHLLQPDLPIYLLGLTQK FGPIYRLHLGLQDVVVLNSKRTIEEAMVKKWADFAGRPEPLTYKLVSRNYPDLSL GDYSLLWKAHKKLTRSALLLGIRDSMEPVVEQLTQEFCERMRAQPGTPVAIEEEF SLLTCSIICYLTFGDKIKDDNLMPAYYKCIQEVLKTWSHWSIQIVDVIPFLRFFP NPGLRRLKQAIEKRDHIVEMQLRQHKESLVAGQWRDMMDYMLQGVAQPSMEEGSG QLLEGHVHMAAVDLLIGGTETTANTLSWAVVFLLHHPEIQQRLQEELDHELGPGA SSSRVPYKDRARLPLLNATIAEVLRLRPVVPLALPHRTTRPSSISGYDIPEGTVI IPNLQGAHLDETVWERPHEFWPDRFLEPGKNSRALAFGCGARVCLGEPLARLELF VVLTRLLQAFTLLPSGDALPSLQPLPHCSVILKMQPFQVRLQPRGMGAHSPGQSQ | 1 |

TABLE 10-continued

Non-limiting examples of 21OH (CYP21A2) and promoter sequences.

| Sequence description | Sequence | SEQ ID NO |
|---|---|---|
| CAG promoter | GCGTTACATAACTTACGGTAAATGGCCCGCCTGGCTGACCGCCCAACGACCCCCG<br>CCCCATTGACGTCAATAATGACGTATGTTCCCATAGTAACGCCAATAGGGACTTTC<br>CATTGACGTCAATGGGTGGAGTATTTACGGTAAACTGCCCACTTGGCAGTACATC<br>AAGTGTATCATATGCCAAGTACGCCCCCTATTGACGTCAATGACGGTAAATGGCC<br>CGCCTGGCATTATGCCCAGTACATGACCTTATGGGACTTTCCTACTTGGCAGTAC<br>ATCTACGTATTAGTCATCGCTATTACCATGGTCGAGGTGAGCCCCACGTTCTGCT<br>TCACTCTCCCCATCTCCCCCCCCTCCCCACCCCCAATTTTGTATTTATTTATTTT<br>TTAATTATTTTGTGCAGCGATGGGGCGGGGGGGGGGGGGGGCGCGCGCCAGGC<br>GGGGCGGGGCGGGGCGAGGGGCGGGGGGGCGAGGCGGAGAGGTGCGGCGGCAG<br>CCAATCAGAGCGGCGCGCTCCGAAAGTTTCCTTTTATGGCGAGGCGGCGGCGGCG<br>GCGGCCCTATAAAAAGCGAAGCGCGCGGCGGGCG | 2 |
| PGK promoter | CCGGTAGGCGCCAACCGGCTCCGTTCTTTGGTGGCCCCTTCGCGCCACCTTCTAC<br>TCCTCCCCTAGTCAGGAAGTTCCCCCCCGCCCCGCAGCTCGCGTCGTGCAGGACG<br>TGACAAATGGAAGTAGCACGTCTCACTAGTCTCGTGCAGATGGACAGCACCGCTG<br>AGCAATGGAAGCGGGTAGGCCTTTGGGGCAGCGGCCAATAGCAGCTTTGCTCCTT<br>CGCTTTCTGGGCTCAGAGGCTGGGAAGGGGTGGGTCCGGGGCGGGCTCAGGGGC<br>GGGCTCAGGGGGGGCGGGCGCCCGAAGGTCCTCCGGAGGCCCGGCATTCTGCA<br>CGCTTCAAAAGCGCACGTCTGCCGCGCTGTTCTCCTCTTCCTCATCTCCGGGCCT<br>TTCGACCTGCAGCC | 3 |
| CB6 Promoter | ccacgttctgcttcactctccccatctccccccctccccaccccaatttttgta<br>tttatttattttttaattatttttgtgcagcgatggggcgggggggggggcgcg<br>cgccaggcggggcggggcggggcgaggggcggggcggggcgaggcggagaggtgc<br>ggcggcagccaatcagagcggcgcgctccgaaagtttccttttatggcgaggcgg<br>cggcggcggcggccctataaaaagcgaagcgcgcggcggg | 48 |
| CBA Promoter | tggtcgaggtgagcccacgttctgcttcactctccccatctccccccctcccc<br>accccaatttttgtatttatttattttttaattatttttgtgcagcgatggggcg<br>ggggggggggggggcgcgcgccaggcggggcggggggggcgaggggcggggcg<br>gggcgaggcggagaggtgcggcggcagccaatcagagcggcgcgctccgaaagtt<br>tccttttatggcgaggcggcggcggcggcggcccctataaaaagcgaagcgcgcgg<br>cgggcgg | 49 |
| Codon Optimized CYP21a2 gene sequence | ATGCTGCTGCTGGGGCTGCTGCTGCTGCTGCCTCTGCTGGCTGGGGCTCGACTGC<br>TGTGGAACTGGTGGAAACTGCGGTCCCTGCACCTGCCACCTCTGGCACCAGGCTT<br>CCTGCACCTGCTGCAGCCAGACCTGCCCATCTACCTGCTGGGCCTGACCCAGAAG<br>TTTGGCCCTATCTATAGGCTGCACCTGGGCCTGCAGGACGTGGTGGTGCTGAACT<br>CTAAGCGCACCATCGAGGAGGCCATGGTGAAGAAGTGGGCAGATTTCGCAGGCCG<br>GCCAGAGCCACTGACATACAAGCTGGTGAGCAGAAATTATCCTGACCTGTCCCTG<br>GGCGATTACTCTCTGCTGTGGAAGGCCCACAAGAAGCTGACAAGGAGCGCCCTGC<br>TGCTGGGCATCCGCGACTCCATGGAGCCAGTGGTGGAGCAGCTGACCCAGGAGTT<br>TTGCGAGAGGATGAGGGCACAGCCTGGAACACCAGTGGCCATCGAGGAGGAGTTC<br>AGCCTGCTGACCTGCTCCATCATCTGTTATCTGACATTTGGCGATAAGATCAAGG<br>ACGATAACCTGATGCCAGCCTACTATAAGTGTATCCAGGAGGTGCTGAAGACCTG<br>GAGCCACTGGAGCATCCAGATCGTGGACGTGATCCCCTTCCTGAGGTTCTTTCCT<br>AATCCAGGCCTGCGGAGACTGAAGCAGGCCATCGAGAAGAGGGATCACATCGTGG<br>AGATGCAGCTGAGGCAGCACAAGGAGTCCCTGGTGGCAGGACAGTGGAGGGACAT<br>GATGGATTACATGCTGCAGGGAGTGGCACAGCCATCTATGGAGGAGGGAAGCGGA<br>CAGCTGCTGGAGGGACACGTGCACATGGCAGCAGTGGATCTGCTGATCGGAGGAA<br>CCGAGACAACAGCCAACACACTGAGCTGGGCCGTGGTGTTTCTGCTGCACCACCC<br>TGAGATCCAGCAGCGGCTGCAGGAGGAGCTGGACCACGAGCTGGGACCTGGAGCA<br>AGCTCCTCTAGAGTGCCATACAAGGATCGGGCCAGACTGCCCCTGCTGAATGCCA<br>CCATCGCCGAGGTGCTGAGGCTGCGCCCCGTGGTGCCTCTGGCCCTGCCTCACAG<br>GACCACAAGACCAAGCTCCATCTCCGGCTATGACATCCCAGAGGGCACCGTGATC<br>ATCCCAAACCTGCAGGGAGCACACCTGGACGAGACAGTGTGGGAGCGGCCACACG<br>AGTTCTGGCCCGATAGATTTCTGGAGCCTGGCAAGAACAGCCGGGCCCTGGCCTT<br>CGGCTGCGGAGCCCGGGTGTGCCTGGGCGAGCCACTGGCCAGGCTGGAGCTGTTC<br>GTGGTGCTGACCCGCCTGCTGCAGGCCTTTACACTGCTGCCCTCCGGCGATGCCC<br>TGCCTTCTCTGCAGCCACTGCCTCACTGCTCCGTGATCCTGAAGATGCAGCCCTT<br>TCAGGTCCGCCTGCAGCCAAGGGGATGGGGGCACATAGTCCAGGGCAGTCTCAG<br>TAA | 50 |

Example 11: Studies with AAVrh10-CAG rAAV

A ssAAVrh10-CAG-CYP21HA vector was produced. This vector contains a genome with AAV2 ITR sequences and encodes AAV rh10 capsid proteins. This rAAV vector was administered to Cyp21$^{-/-}$ mice intravenously (i.v.).

In a first experiment, 7-month-old mice were studied. Ten mice (4 female, 6 male) were injected with ssAAVrh10-CAG-CYP21HA at 2×10$^{10}$ vg/g body weight. 2 of the 6 male died 3 weeks post-treatment. Four mice were untreated with the vector.

Figure 42:
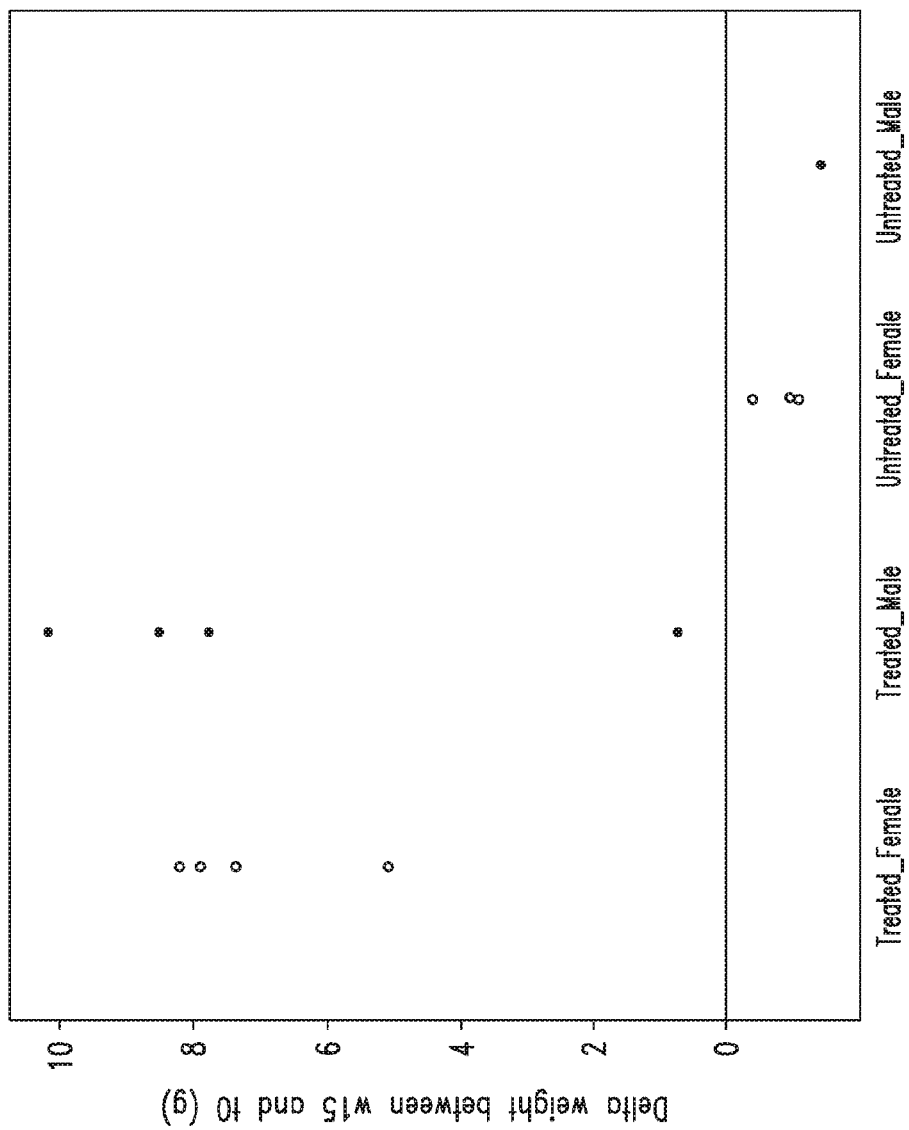
FIG. 42 shows a graph showing the delta (change in) body weight of 7-month-old Cyp21$^{-/-}$ mice either treated with ssAAV10-CAG-CYP21HA or untreated with rAAV. The body weight was measured at t0 (injection) and w15 (15 weeks post-treatment).
Figure 44:
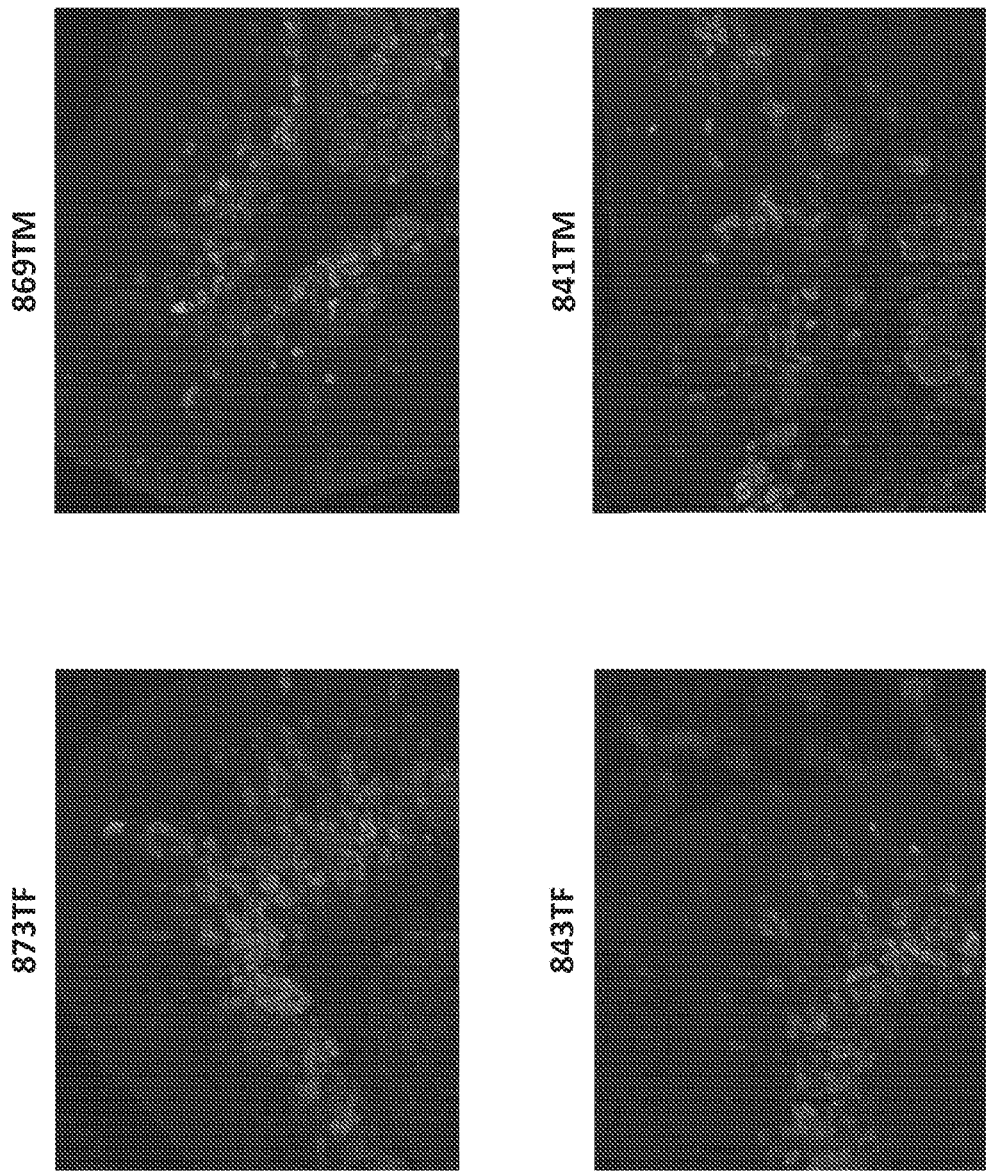
FIG. 44 shows CYP21-CY3 immunofluorescence images of adrenal glands of 7-month-old Cyp21$^{-/-}$ mice treated with ssAAV10-CAG-CYP21HA at 15 weeks post-treatment. "TF" refers to "treated female". "TM" refers to "treated male". The figure includes identification numbers for the mice used to generate the images.
Figure 45:
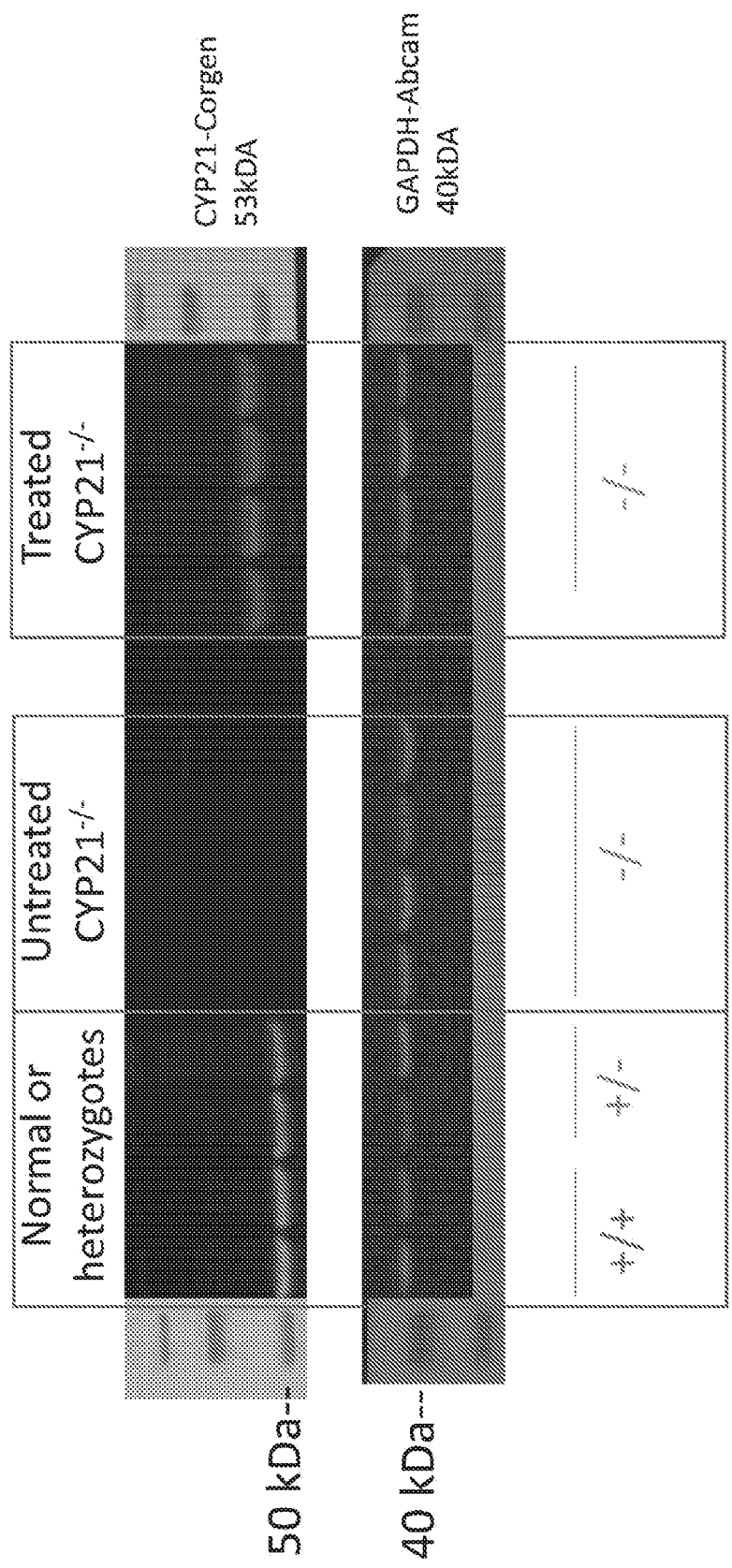
FIG. 45 shows an image of a western blot of CYP21 expression in 7-month-old Cyp21-mice treated with ssAAV10-CAG-CYP21HA at 15 weeks post-treatment, untreated Cyp21-mice and Cyp21 wild-type (+/+) or Cyp21 heterozygous (+/−) mice. CYP21 was detected with an anti-CYP21 antibody (CorGen). The figure includes identification numbers for the mice used to generate the data.

Various parameters were measured in mice at 15 weeks post-treatment. Change in body weight between the time of treatment and 15 weeks post-treatment was determined for treated and untreated animals (FIG. 42). CYP21HA vector genome copy (VGC) values were determined for the animals treated with the rAAV vector (Table 11). HA expression and CYP21 expression in the adrenals was visualized by immunofluorescence (IF) (FIGS. 43 and 44). CYP21 expression was visualized by western blot (FIG. 45). An anti-CYP21 antibody (CorGen) was used in IF and western blot assays. Urinary progesterone (ng/mg creatinine) was measured in treated and untreated Cyp21$^{-/-}$ mice over the course of 15 weeks (FIGS. 46A-46B). Urinary progesterone (ng/mg creatinine) was also measured in treated and untreated wild-type mice over the course of 15 weeks (FIG. 46C). The data demonstrate the therapeutic effect of the CYP21 gene therapy product by showing that progesterone levels in treated mice revert to levels that are much closer to levels in wild-type mice.

Fifteen weeks after being injected with ssAAVrh10-CAG-CYP21HA at the age of 7 months, Cyp21$^{-/-}$ mice expressed an effective VGC value, showed strong CYP21HA IF signal, expressed CYP21 protein and had improved body weight.

TABLE 11

CYP21 VGC in adrenals of 7-month-old Cyp21$^{-/-}$ mice 15 weeks post-injection with ssAAVrh10-CAG-CYP21HA.

| Mouse ID | VGC | Δ weight (w15-w0) (g) |
|---|---|---|
| 873 TF | 0.90 | 7.8 |
| 836 TF | 0.65 | 7.9 |
| 843 TF | 0.47 | 8.2 |
| 319 TF | 2.70 | 5.1 |
| 869 TM | 0.69 | 7.8 |
| 841 TM | 0.30 | 10.2 |
| 247 TM | 2.30 | 8.5 |
| 248 TM | 0.45 | 0.78 |

TF = treated female; TM = treated male

In a second experiment, 2-3-month-old mice were studied. Seventeen mice (9 female, 8 male) were injected with ssAAVrh10-CAG-CYP21HA at 2×10$^{10}$ vg/g body weight or 1×10$^{10}$ vg/g body weight. Seven mice were untreated with the vector.

Figure 47:
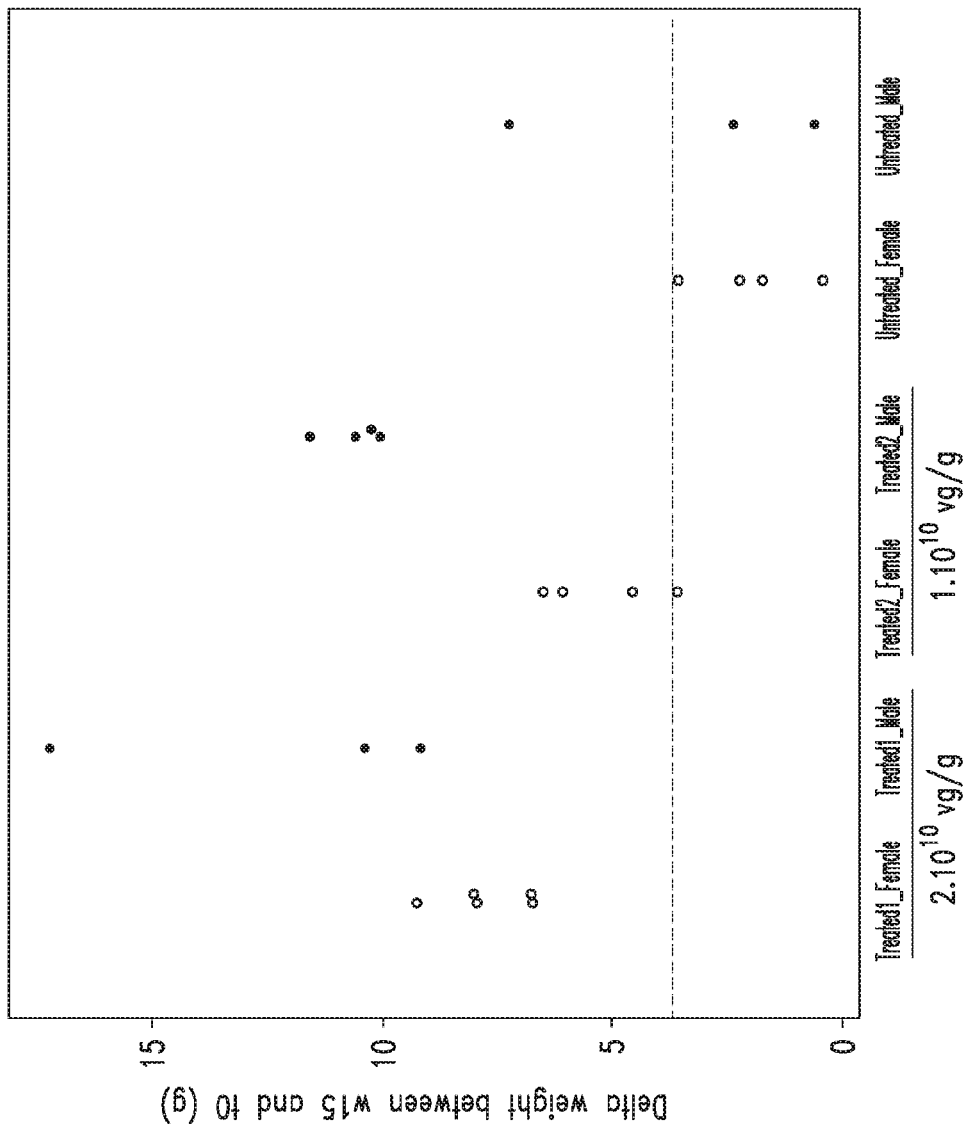
FIG. 47 shows a graph showing the delta (change in) body weight of 2-3-month-old Cyp21$^{-/-}$ mice either treated with ssAAV10-CAG-CYP21HA or untreated with rAAV. The body weight was measured at t0 (injection) and w15 (15 weeks post-treatment).
Figure 48:
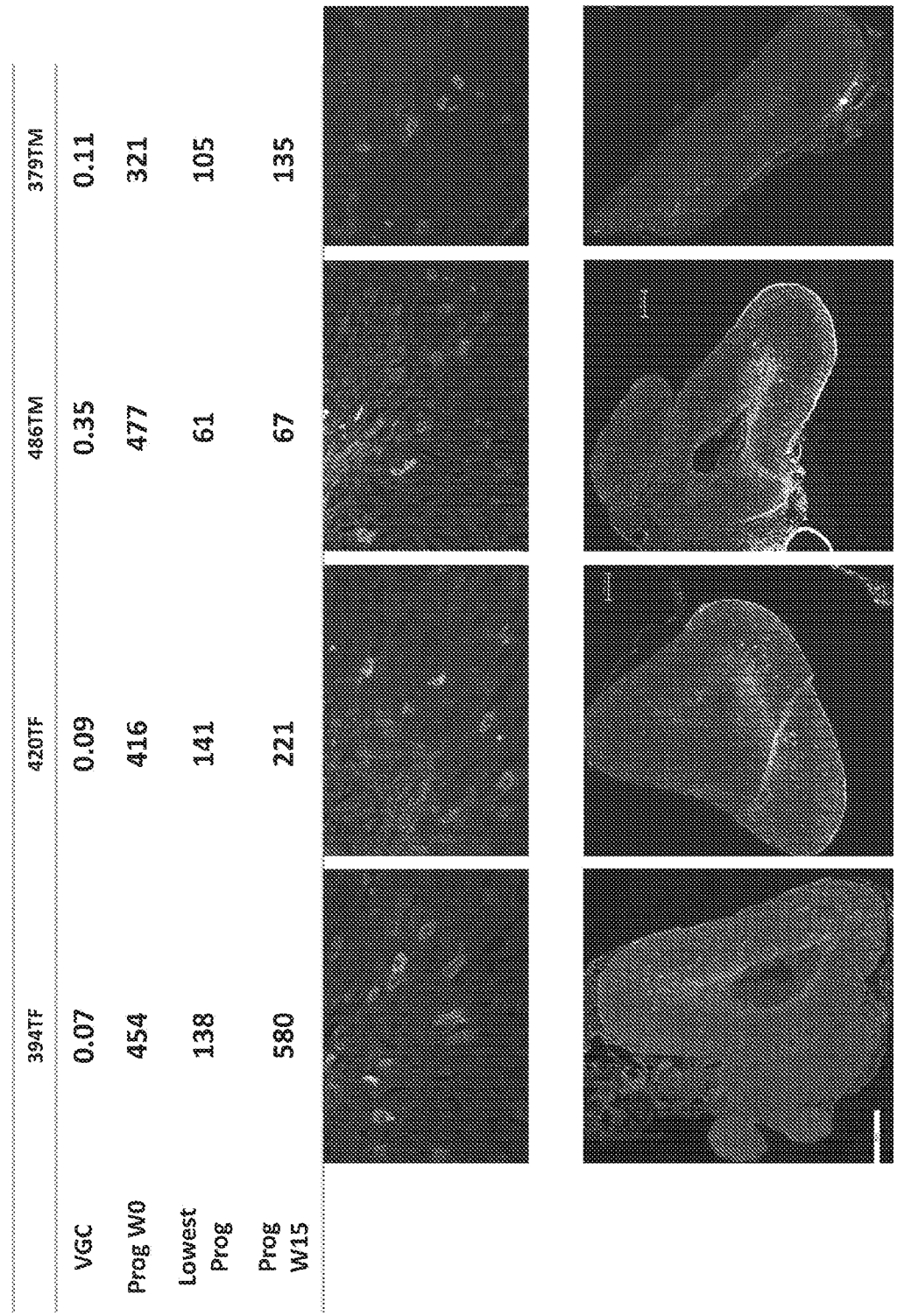
FIG. 48 depicts a table with viral genome copy (VGC) measurements for adrenal glands of specific 2-3-month-old Cyp21$^{-/-}$ mice that were administered ssAAV10-CAG-CYP21HA intravenously at 18 weeks post-treatment. The table also includes corresponding urinary progesterone levels (ng/mg creatinine) in each mouse at the time of injection with the rAAV (Prog W0), the lowest progesterone levels (Lowest Prog) and progesterone levels 15 weeks post-treatment (Prog W15).
Figure 50:
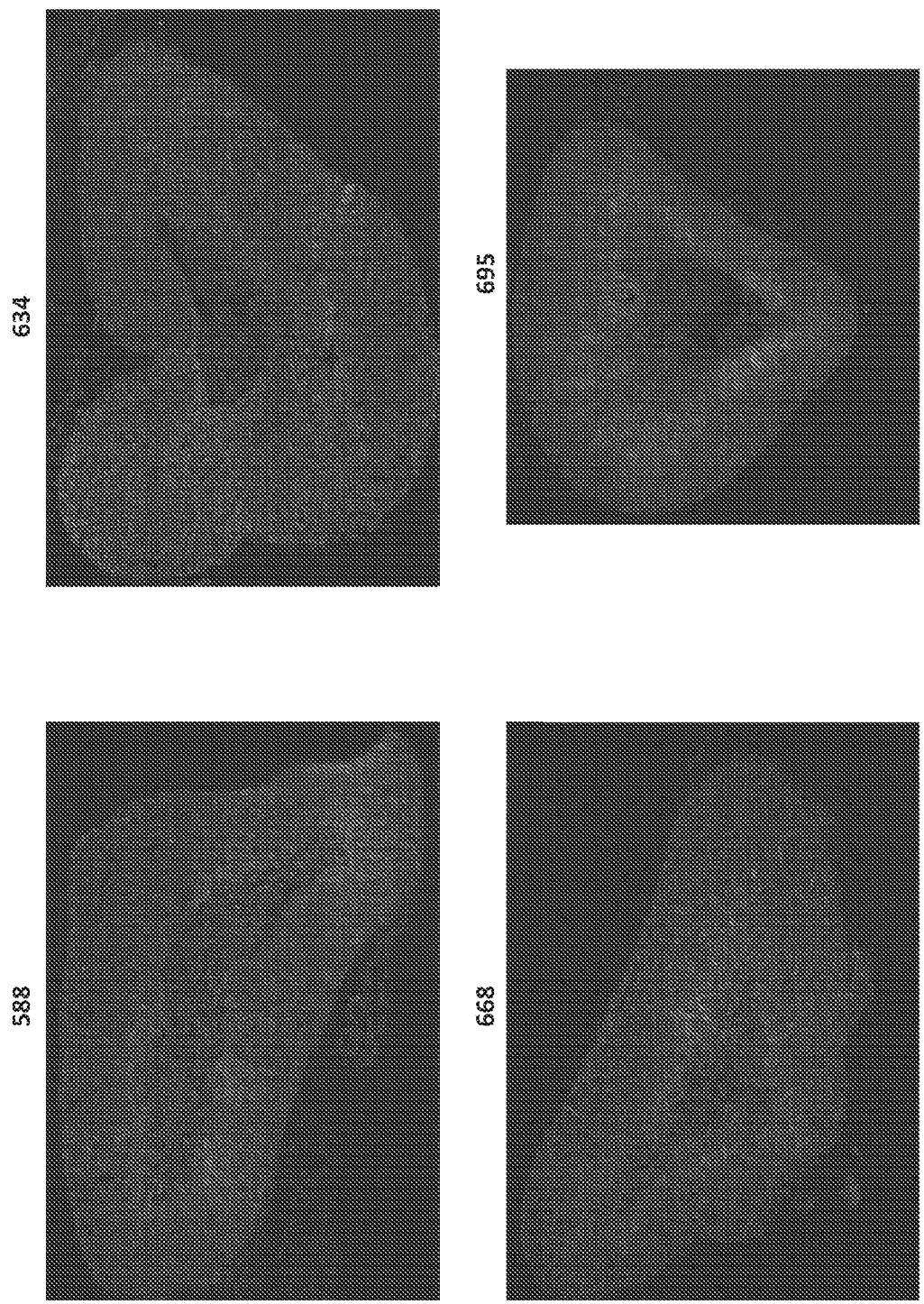
FIG. 50 shows CYP21HA immunofluorescence images of adrenal glands of 2-3-month-old Cyp21$^{-/-}$ mice treated with ssAAV10-CAG-CYP21HA at 1 week post-treatment. The figure includes identification numbers for the mice used to generate the images.
Figure 51:
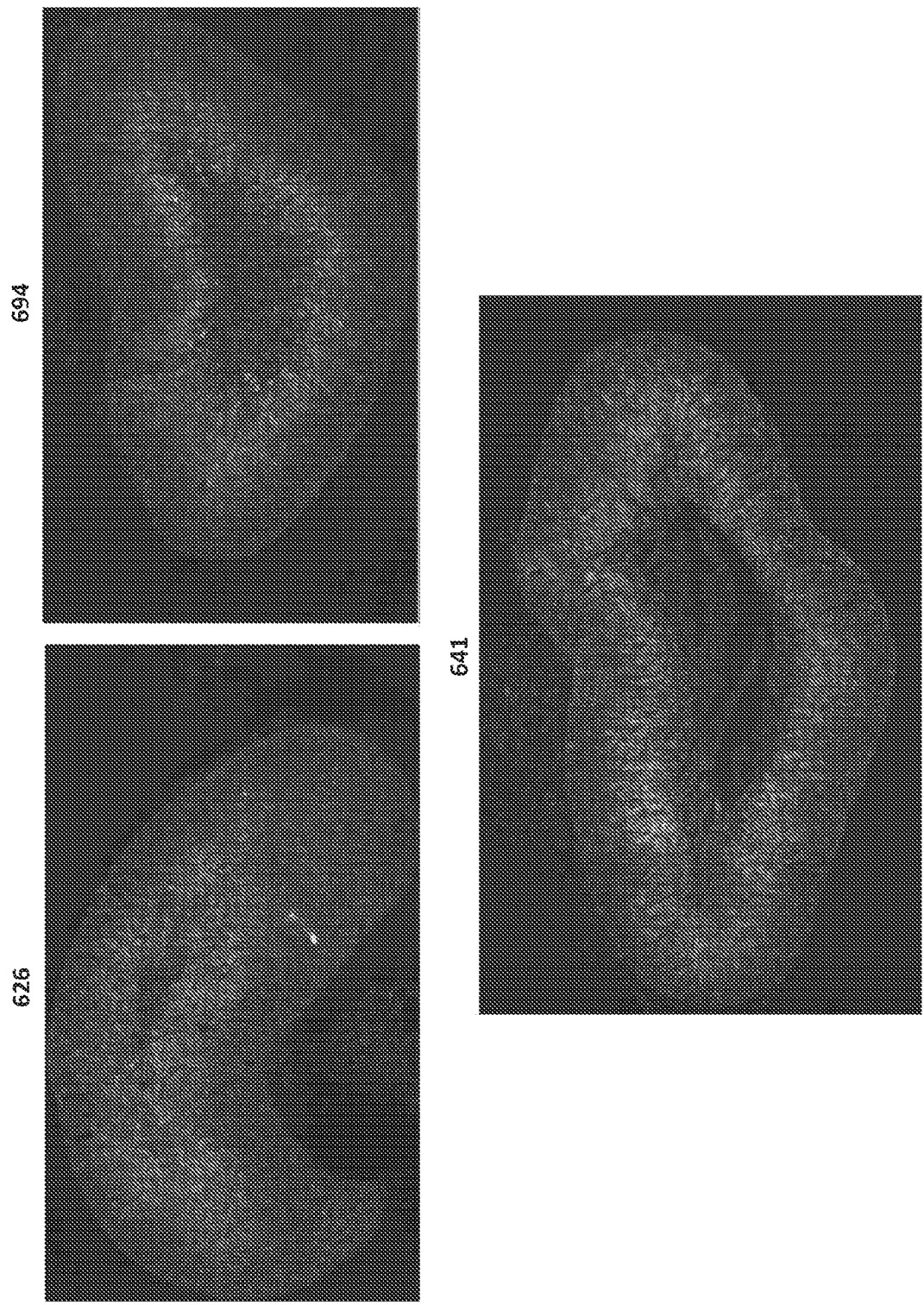
FIG. 51 shows CYP21HA immunofluorescence images of adrenal glands of 2-3-month-old Cyp21$^{-/-}$ mice treated with ssAAV10-CAG-CYP21HA at 3 weeks post-treatment. The figure includes identification numbers for the mice used to generate the images.
Figure 52C:
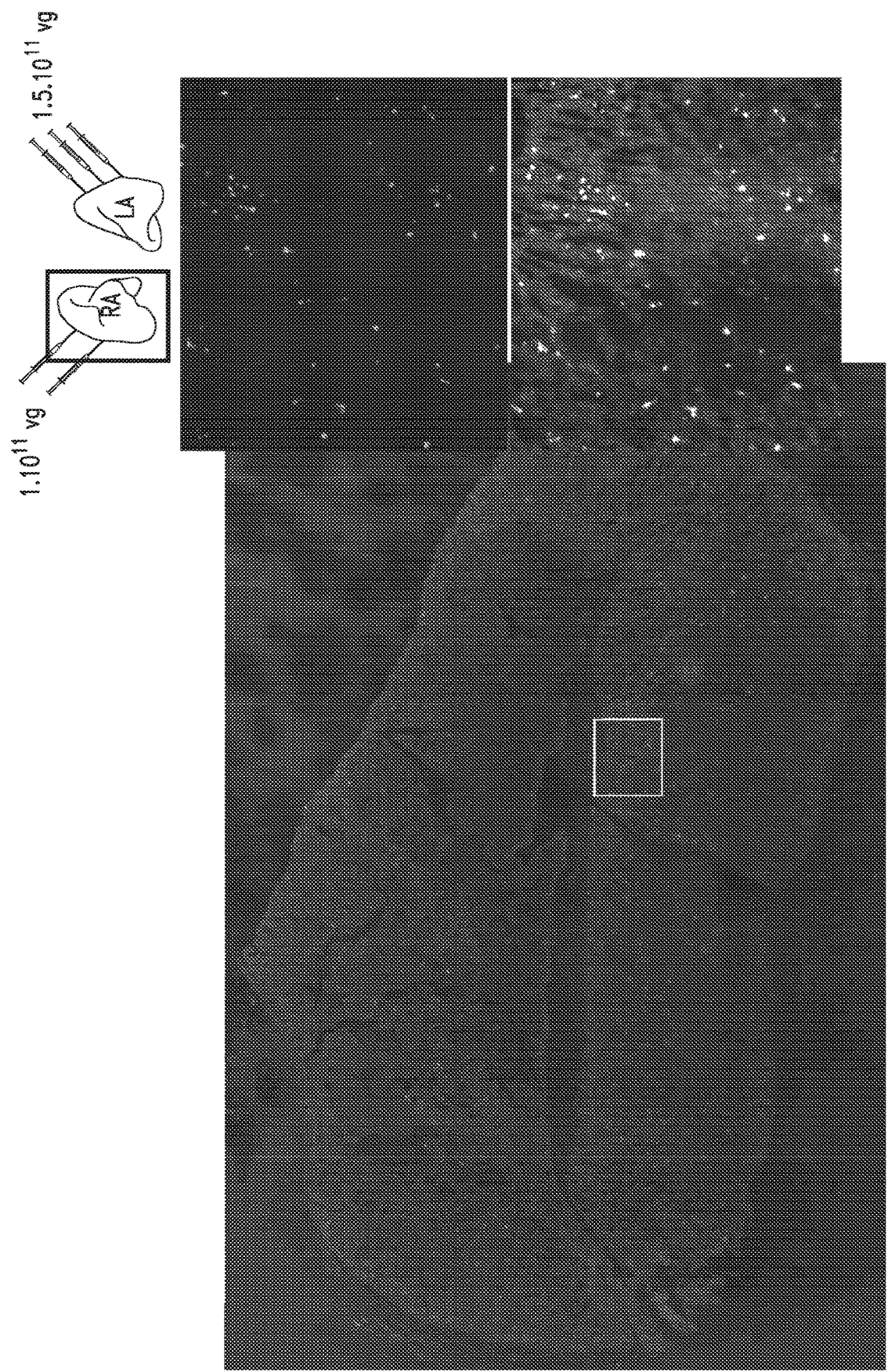
Figure 53C:
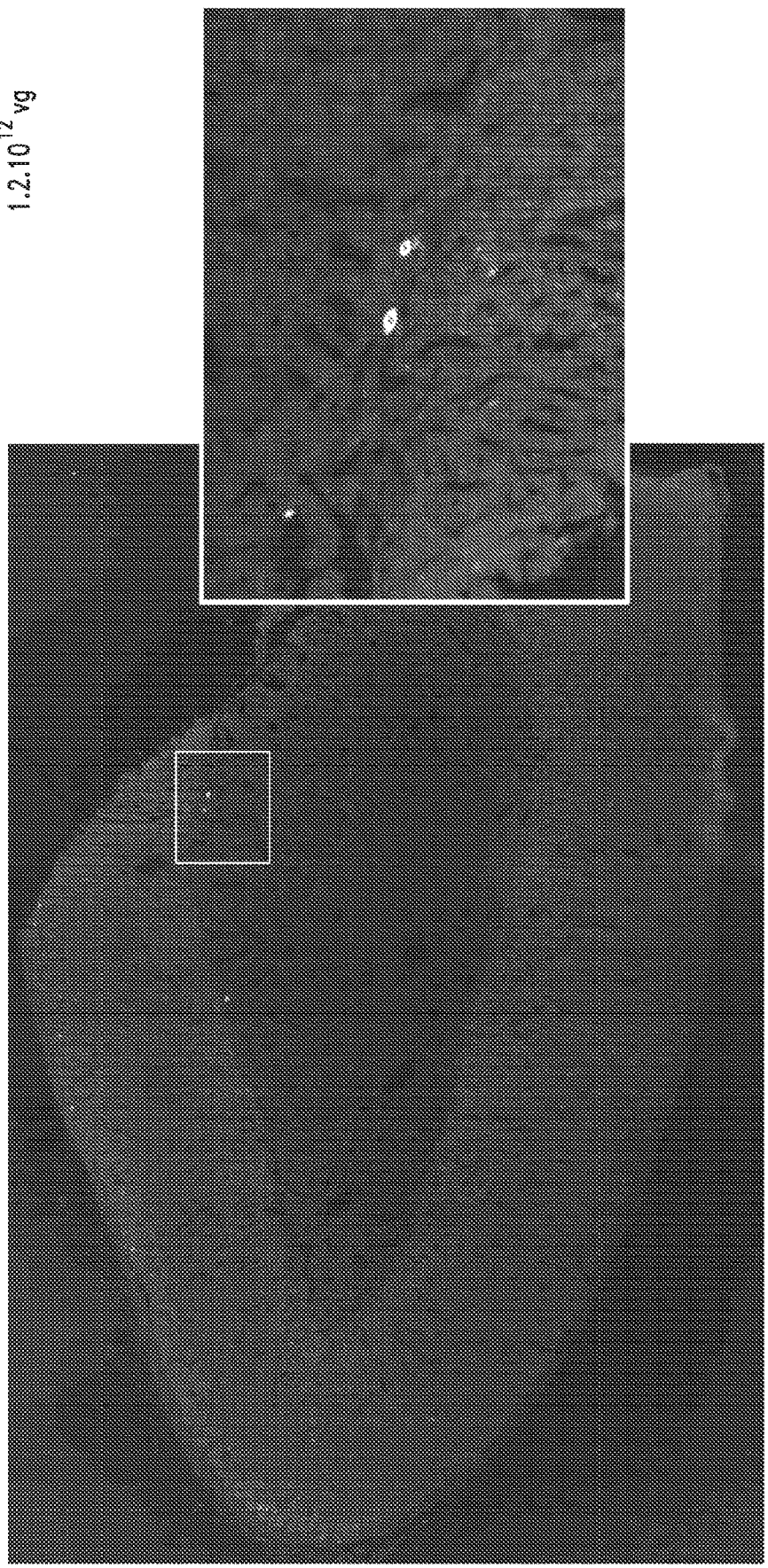
Figure 54A:
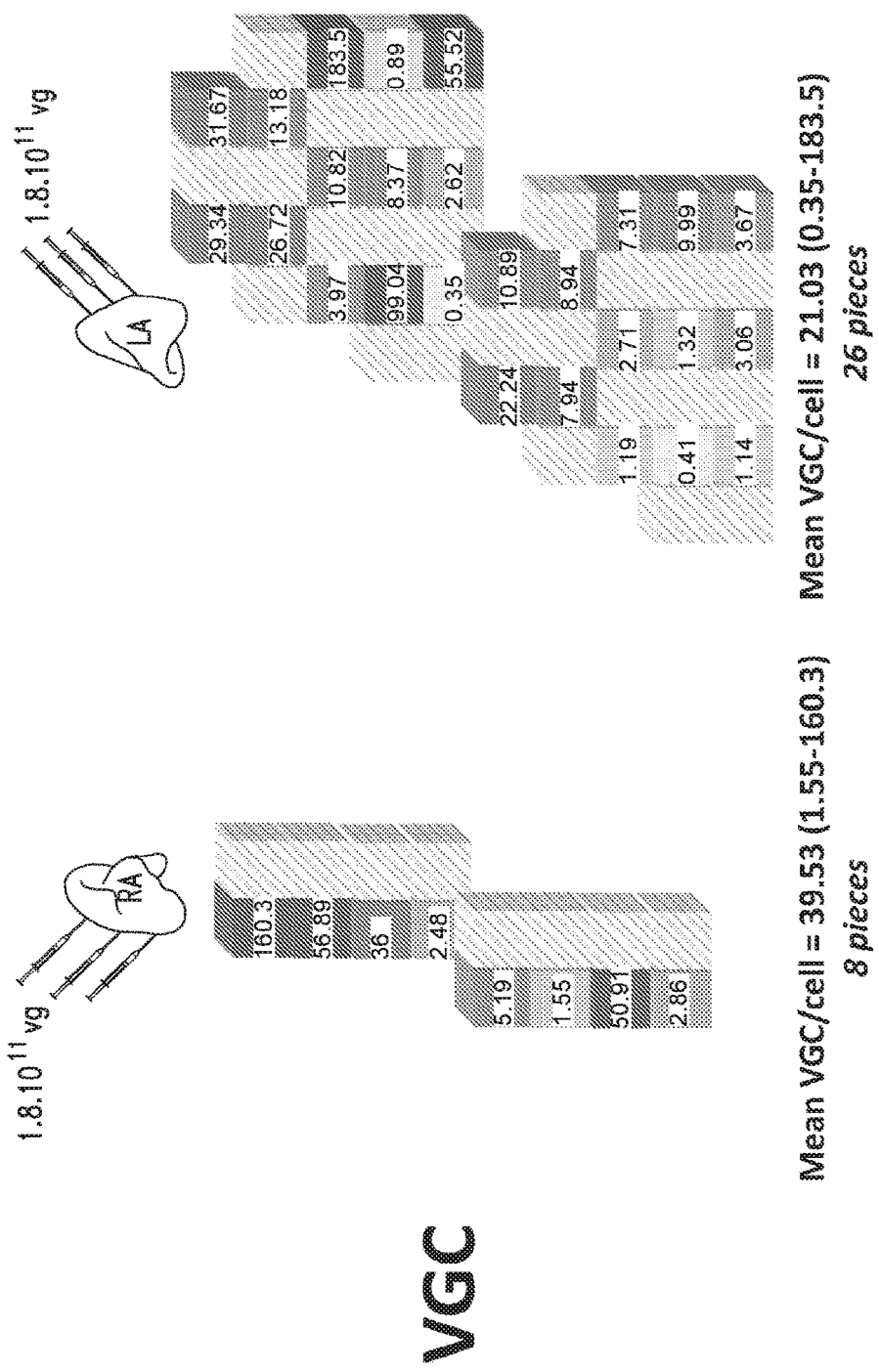
FIG. 54A-FIG. 54C show results obtained after intra-adrenal administration of AAV5-CAG-hCYP21HA to non-human primate number 6 (NHP06), a 28-month-old female weighing 2.8 kg. The animal screened negative for neutralizing antibodies for AAV5 and AAV6 and screened positive for AAV1 (1/5) about two months before the rAAV administration. The animal screened negative for neutralizing antibodies for AAV1 and AAV5 and screened positive for AAV6 (1/5) about two weeks before the rAAV administration.
Figure 54B:
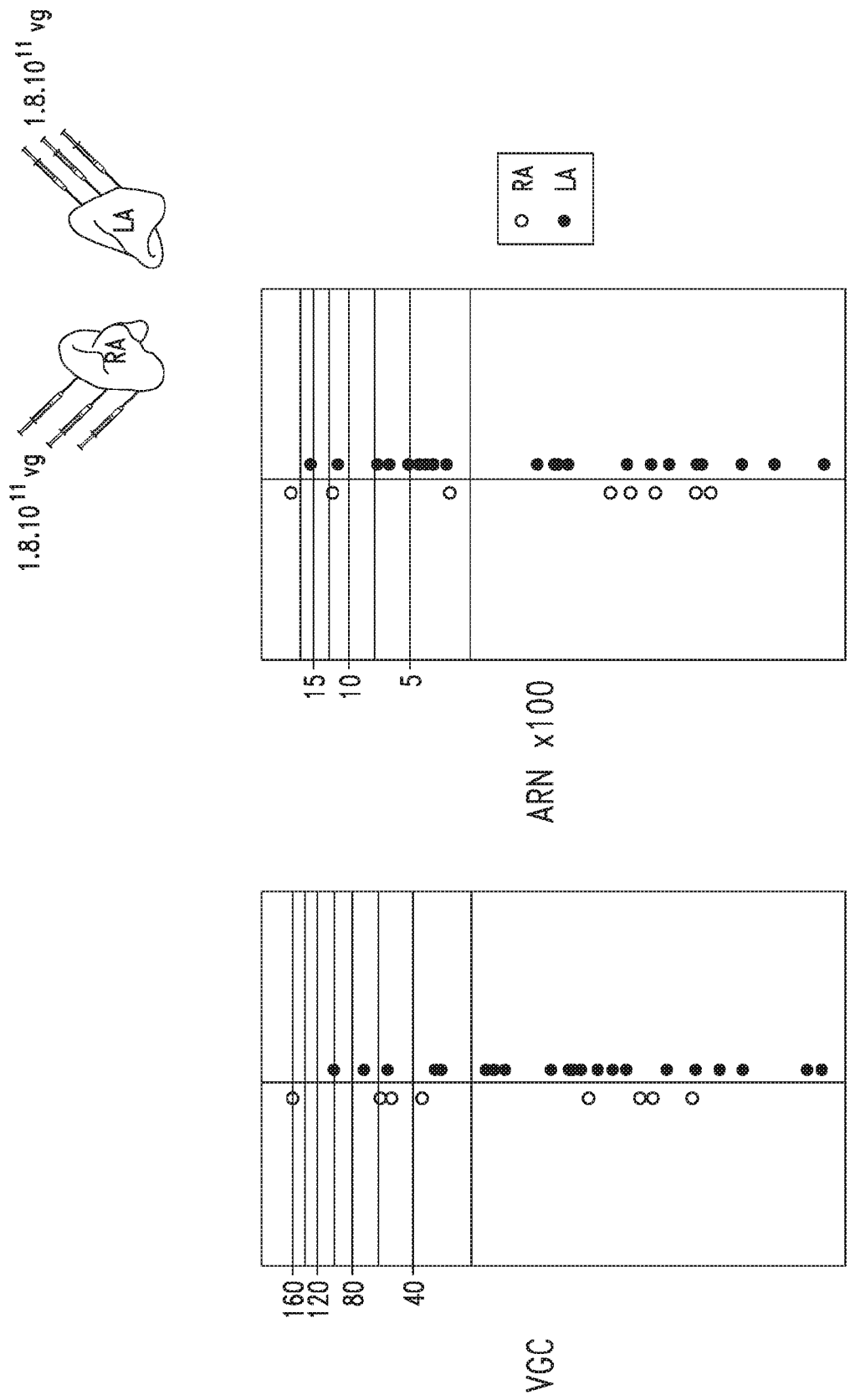
Figure 54C:
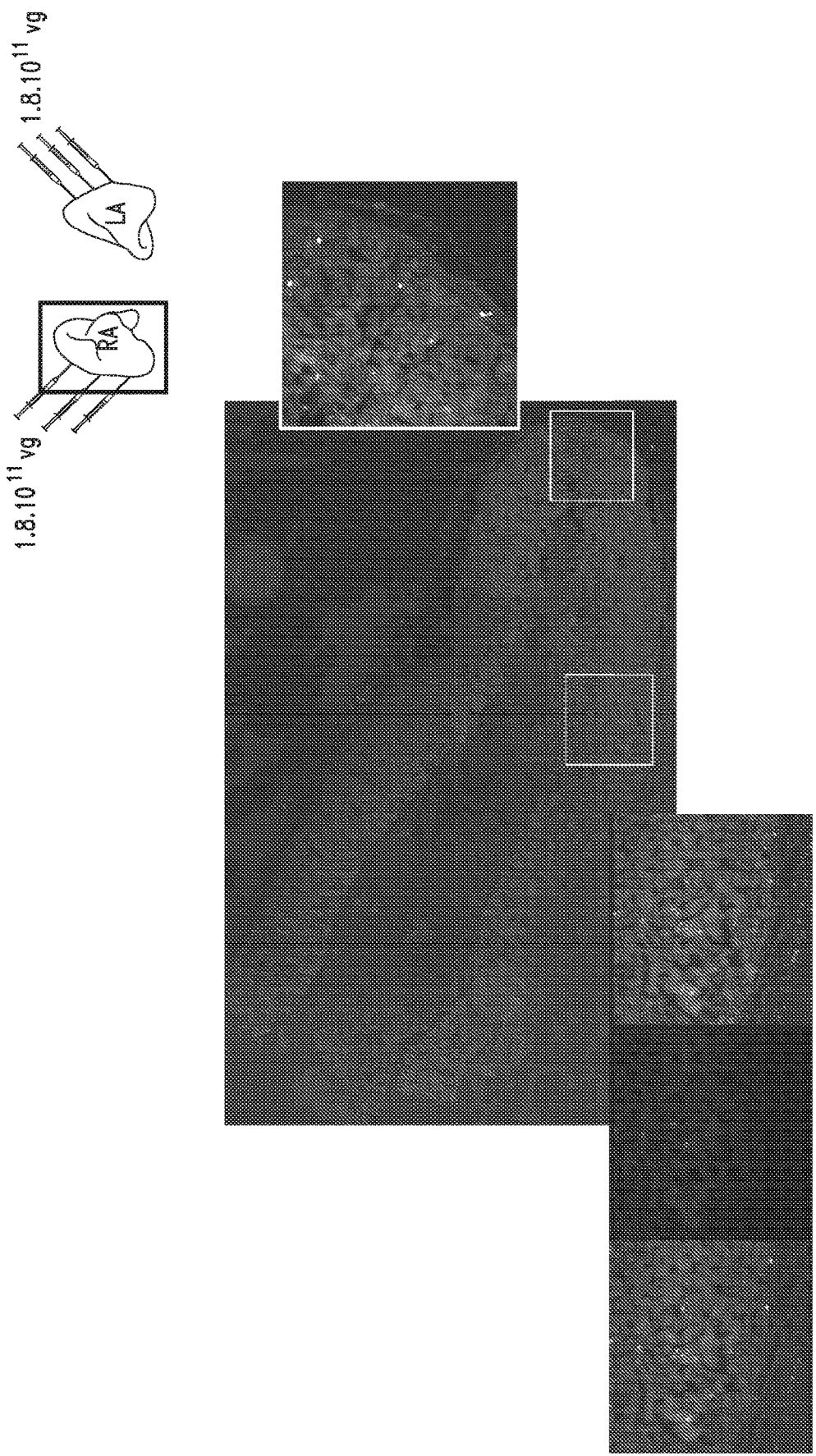
Figure 55A:
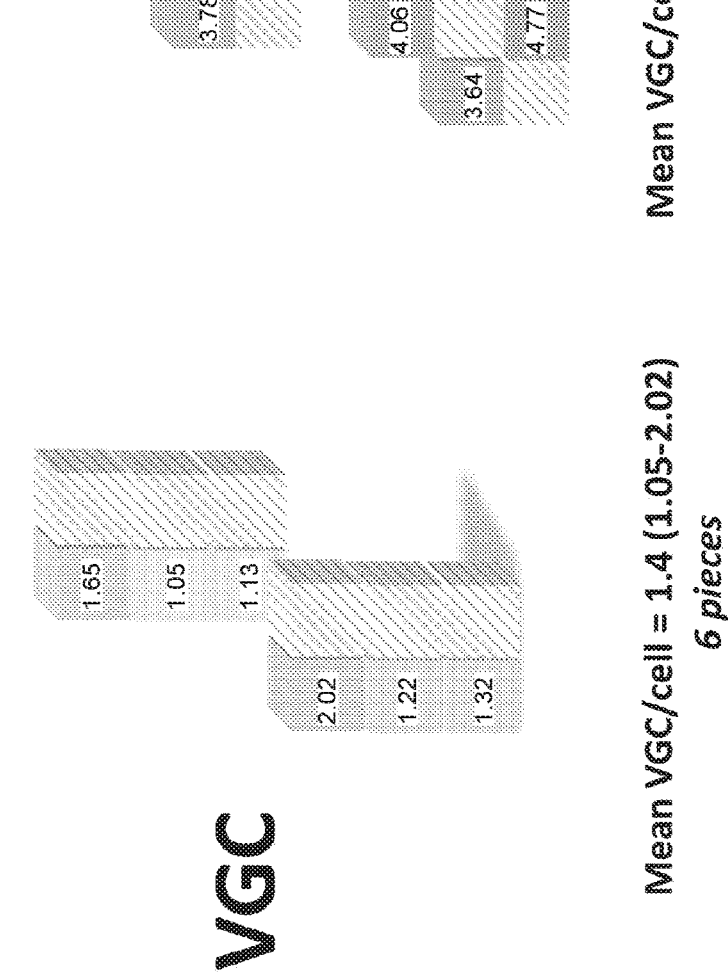
Figure 56A:
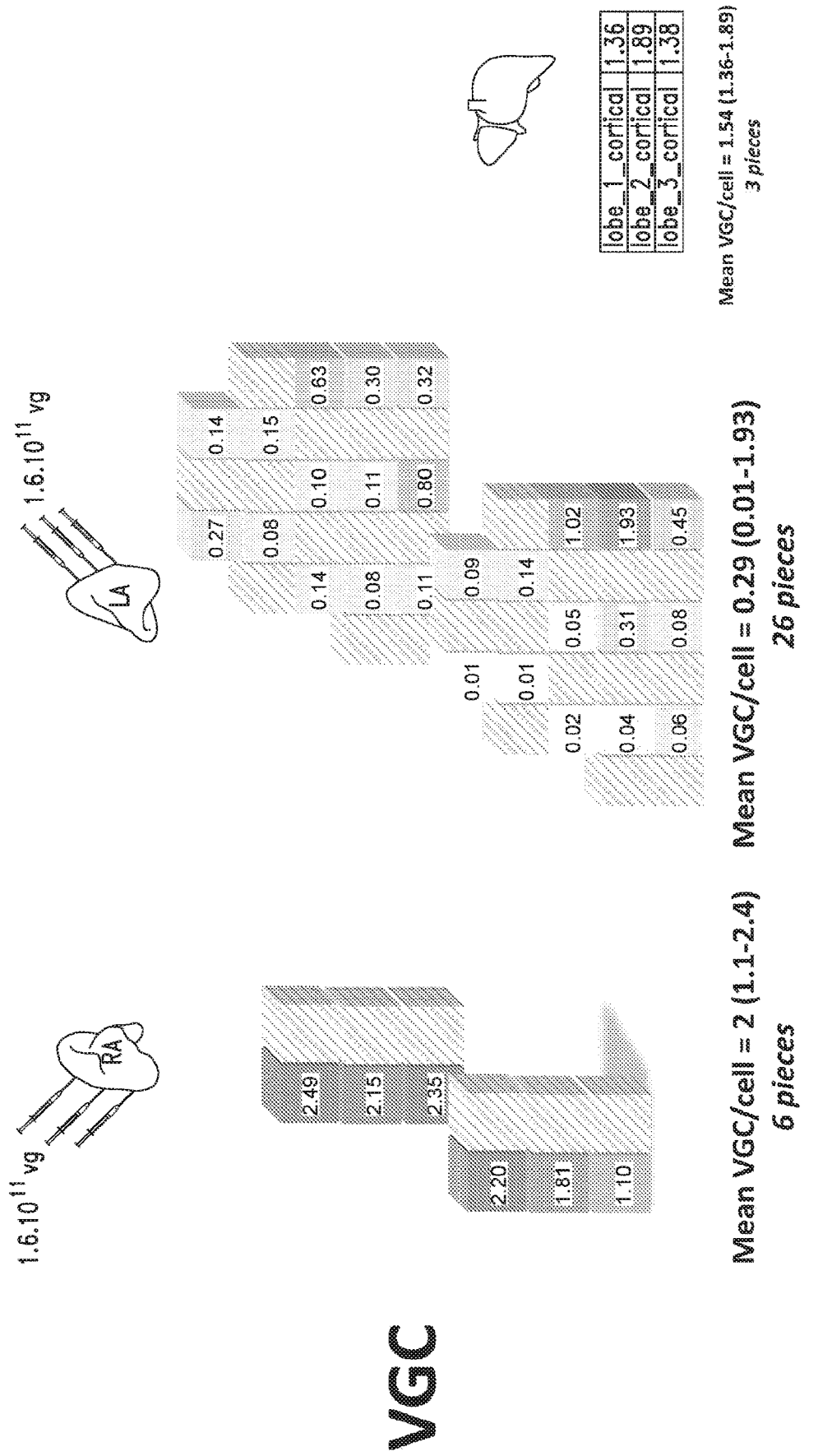
FIG. 56A-FIG. 56C show results obtained after intra-adrenal administration of AAV6-CAG-hCYP21HA to non-human primate number 7 (NP07), a 28-month-old female weighing 2.85 kg. The animal screened negative for neutralizing antibodies for AAV1, AAV5 and AAV6 about two months before the rAAV administration. The animal screened positive for neutralizing antibodies for AAV1 (1/5), AAV5 (1/5) and AAV6 (1/5) about two weeks before the rAAV administration.
Figure 56B:
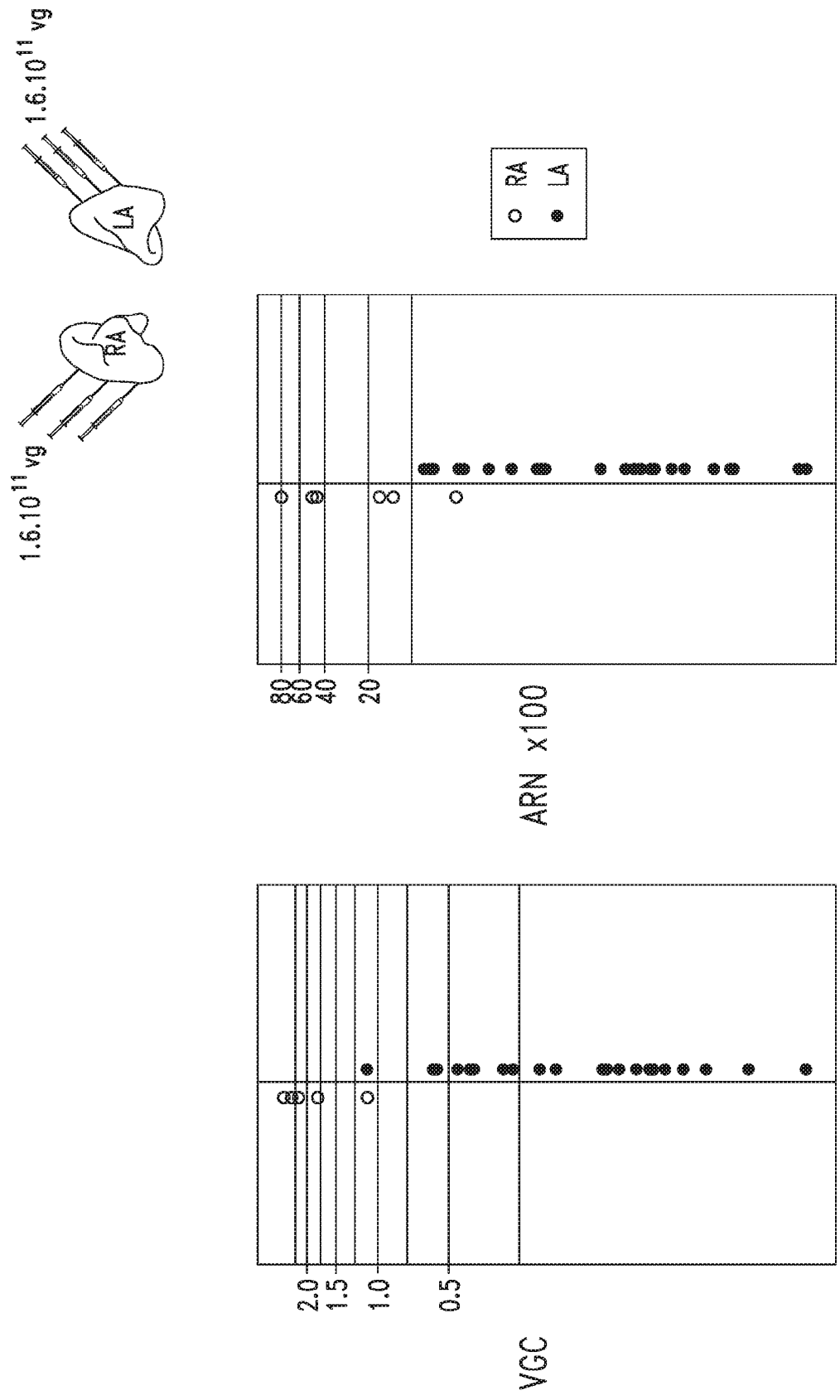
Figure 56C:
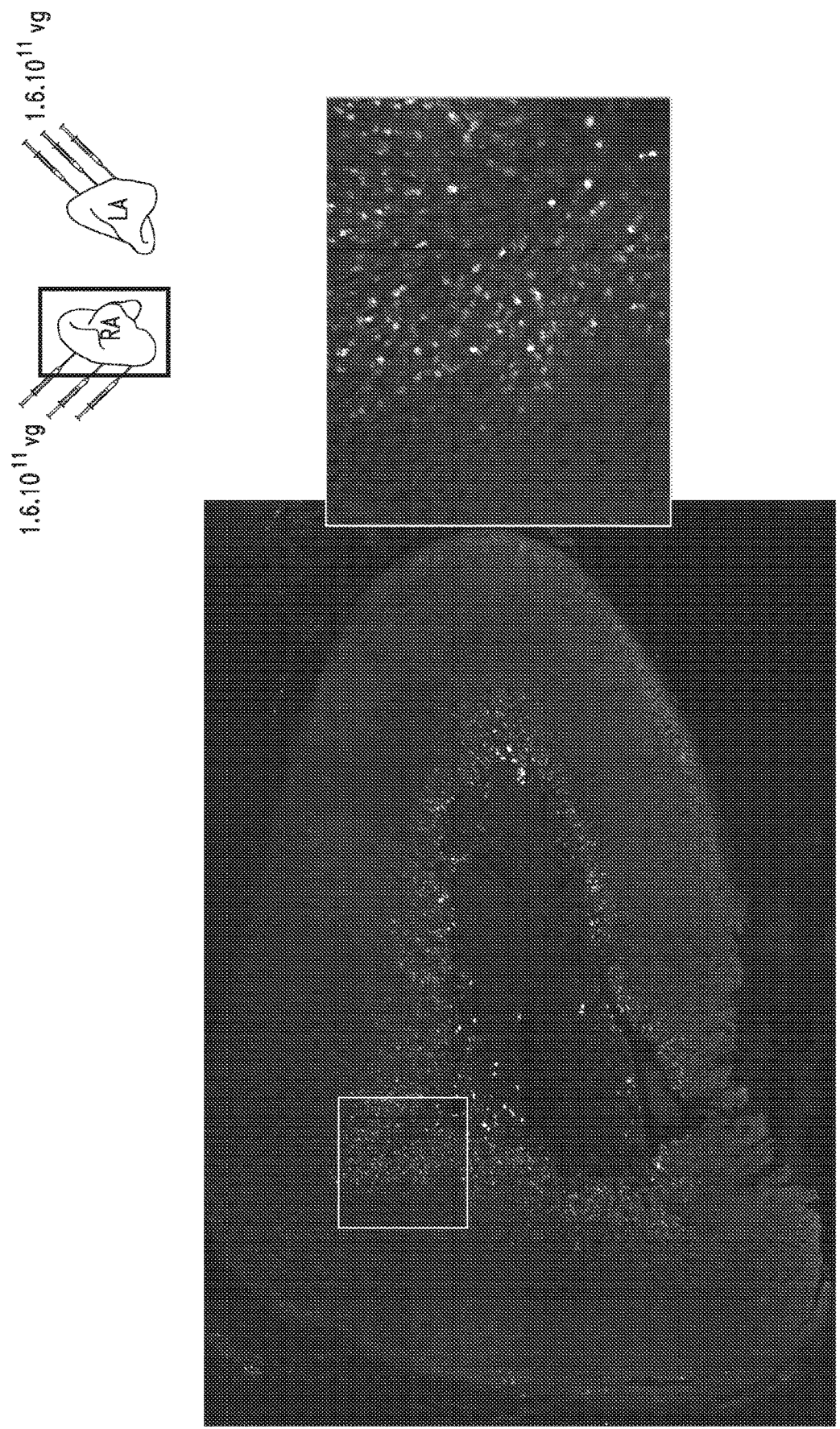
Figure 57A:
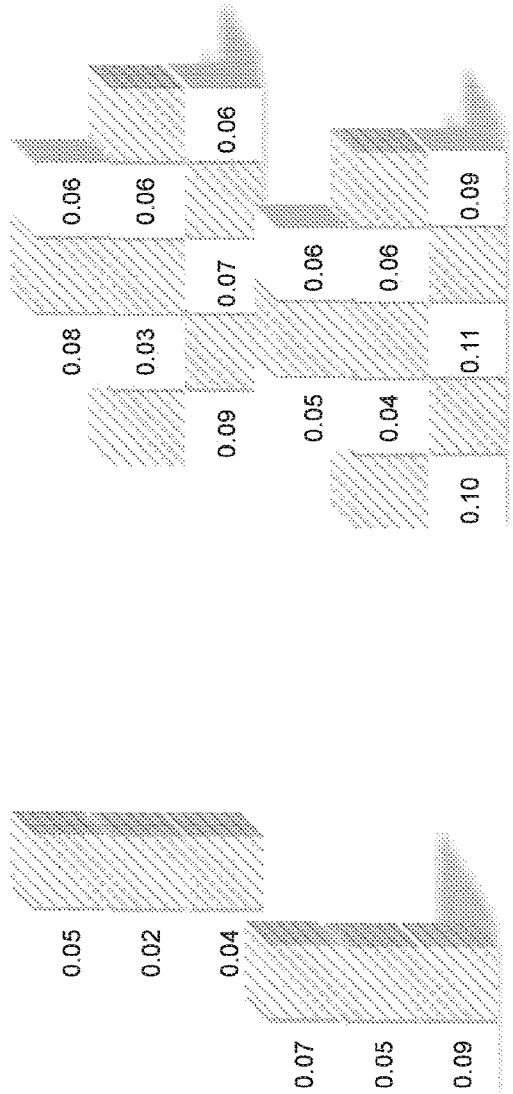
FIG. 57A-FIG. 57C show results obtained after intravenous administration of AAV6-CAG-hCYP21HA to non-human primate number 10 (NHP10), a 28-month-old female weighing 2.35 kg. The animal screened negative for neutralizing antibodies for AAV1, AAV5 and AAV6 about two months before the rAAV administration. The animal screened negative for neutralizing antibodies for AAV5 and AAV6 and positive for AAV1 (1/5) about two weeks before the rAAV administration.
Figure 57B:
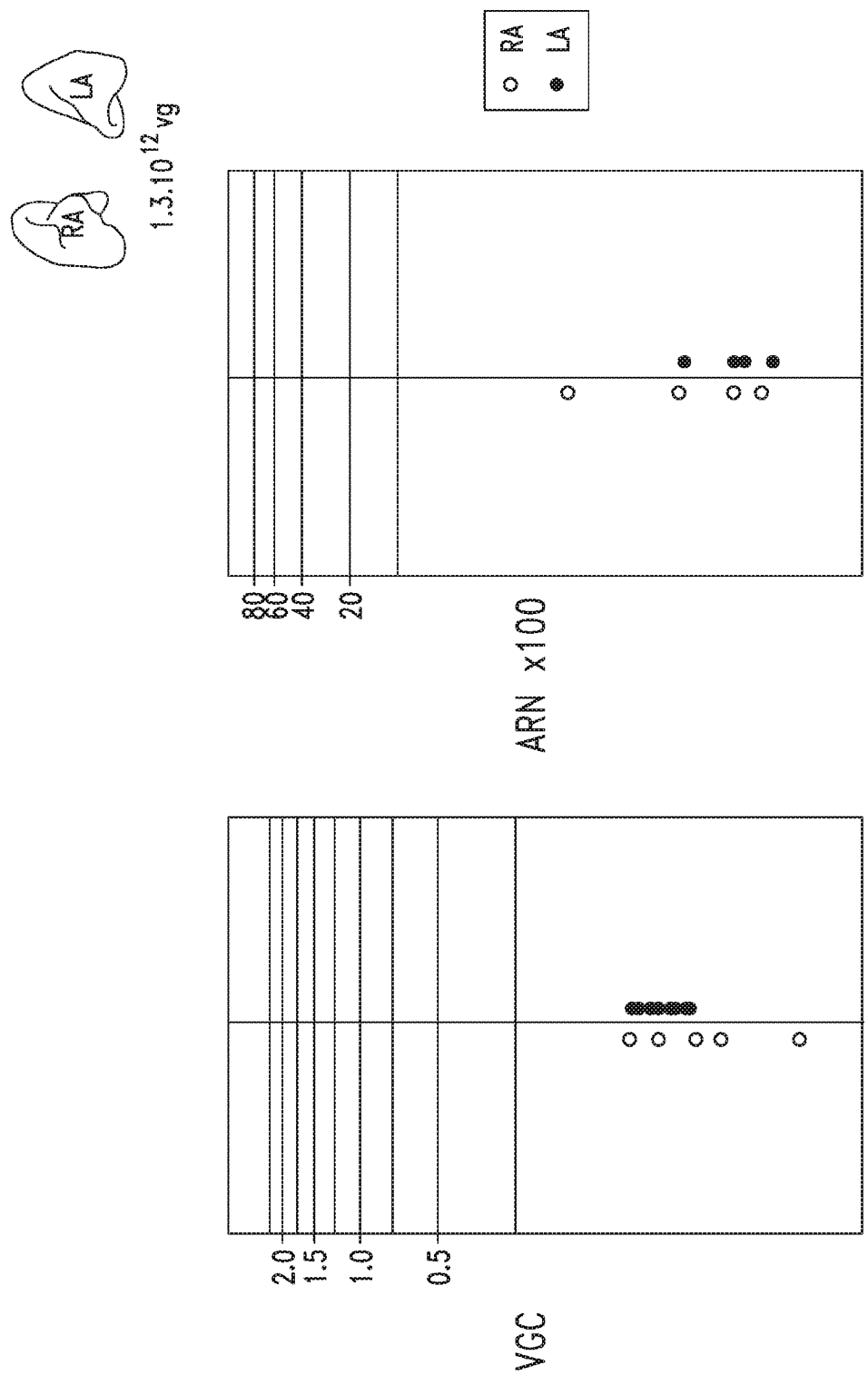
Figure 57C:

Various parameters were measured in mice at 15-18 weeks post-treatment. Change in body weight between the time of treatment and 15 weeks post-treatment was determined for treated and untreated animals (FIG. 47). CYP21HA vector genome copy (VGC) values were determined for the animals treated with the rAAV 18 weeks post-treatment (FIG. 48). HA expression in the adrenals was visualized by immunofluorescence (IF) (FIGS. 48, 50 and 51). Urinary progesterone (ng/mg creatinine) was measured in 13 treated animals and all untreated animals over the course of 15 weeks (FIGS. 49A-49B and Table 12).

TABLE 12

Urinary progesterone levels in 2-3-month-old Cyp21$^{-/-}$ mice treated with ssAAVrh10-CAG-CYP21HA at 2 × 10$^{10}$ vg/g body weight or 1 × 10$^{10}$ vg/g body weight.

| | 2 × 10$^{10}$ vg/g body weight | 1 × 10$^{10}$ vg/g body weight |
|---|---|---|
| Mean progesterone (T0) | 439.6 | 666.4 |
| Mean lowest progesterone value observed during the 15-week period | 114.9 | 84.3 |
| Mean progesterone at euthanasia (15 weeks post-treatment) | 222.9 | 165.1 |

At 15 weeks post-treatment of 2-3-month-old Cyp21 mice, urinary progesterone levels were halved in 4/13 treated mice and divided by approximately 8 in 6/13 treated mice. Therapeutic results (e.g., progesterone levels, weight, steroidogenesis mRNA and response to stress) were apparent at 15 weeks even with a low persisting VGC level (<0.5).

Example 12: Studies Comparing AAV1, AAV5 and AAV6 rAAV Vectors

We compared the efficacy of recombinant vectors having an AAV1, AAV5 or AAV6 serotype in delivering the human wild-type CYP21 transgene (hCYP21) or GFP to non-human primates (NHP) (*Macaca fascicularis*). The treatments and selected results are summarized in Table 13. The promoters used in the vectors were CAG, PGK or CB6. The hCYP21 transgene was fused to a hemagglutinin (HA) tag. The non-human primate identifiers are provided in the column labeled "NHP ID". The route of administration was intra-adrenal (IA) injection or intravenous injection (IV). The "Gland injected" column indicates whether the right adrenal or left adrenal was injected. In some cases, vector escaped from IA injection into the circulation and transduced the non-injected gland. Table 13 also provides the injected dose for the vectors. Vector genome copy (VGC) measurements were made after organs were dissected and processed. mRNA levels of either CYP21 or GFP were measured by quantitative reverse transcription PCR (qRT-PCR) after organs were dissected and processed. The mRNA values are expression of hCYP21 relative to GAPDH. HA or GFP expression was also visualized by immunofluorescence (IF). The levels of expression are provided in the column labeled "IF".

Figure 59:
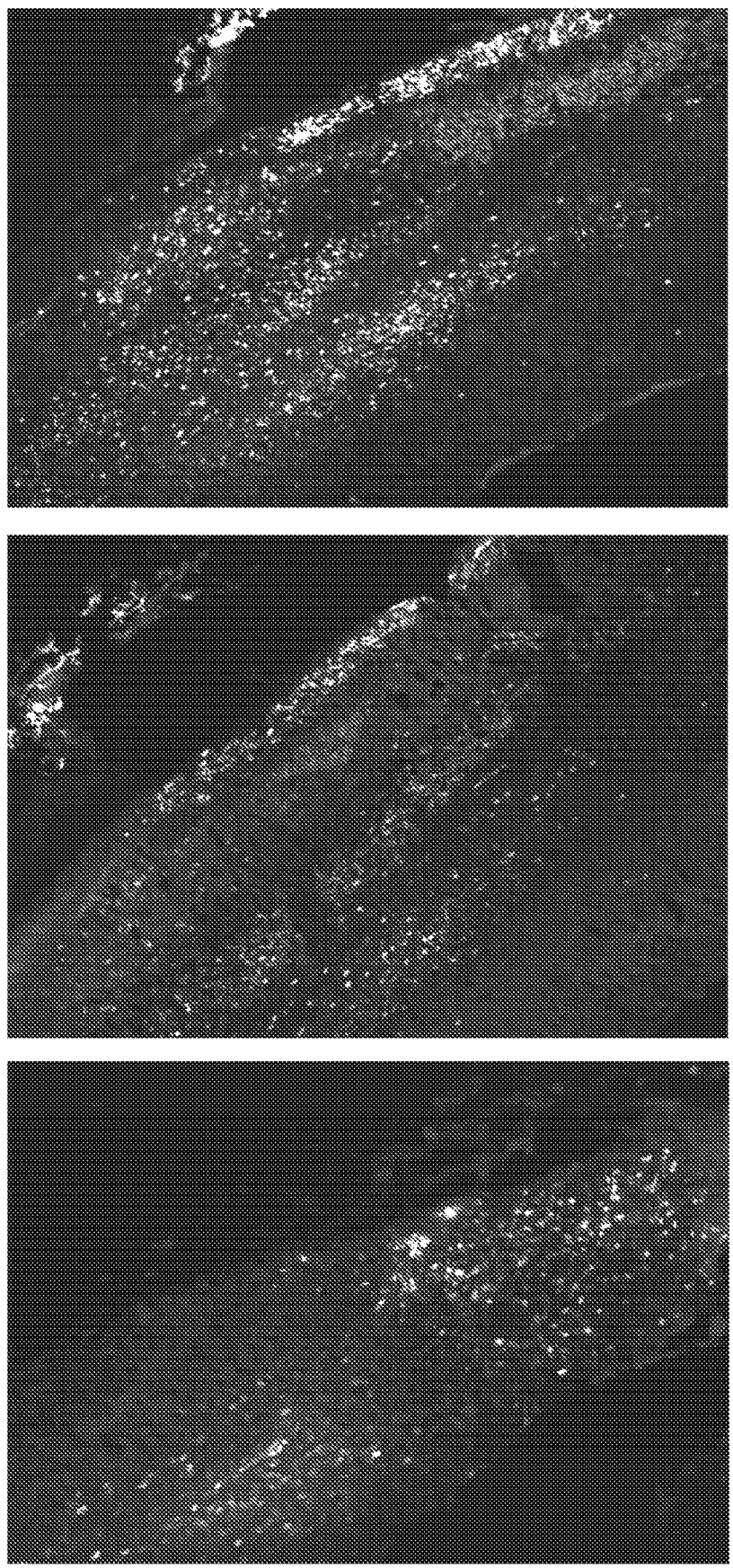
FIG. 59 shows GFP immunofluorescence images of the left adrenal of non-human primate number 2 (NHP02) treated with AAV6-CAG-GFP.
Figure 60:
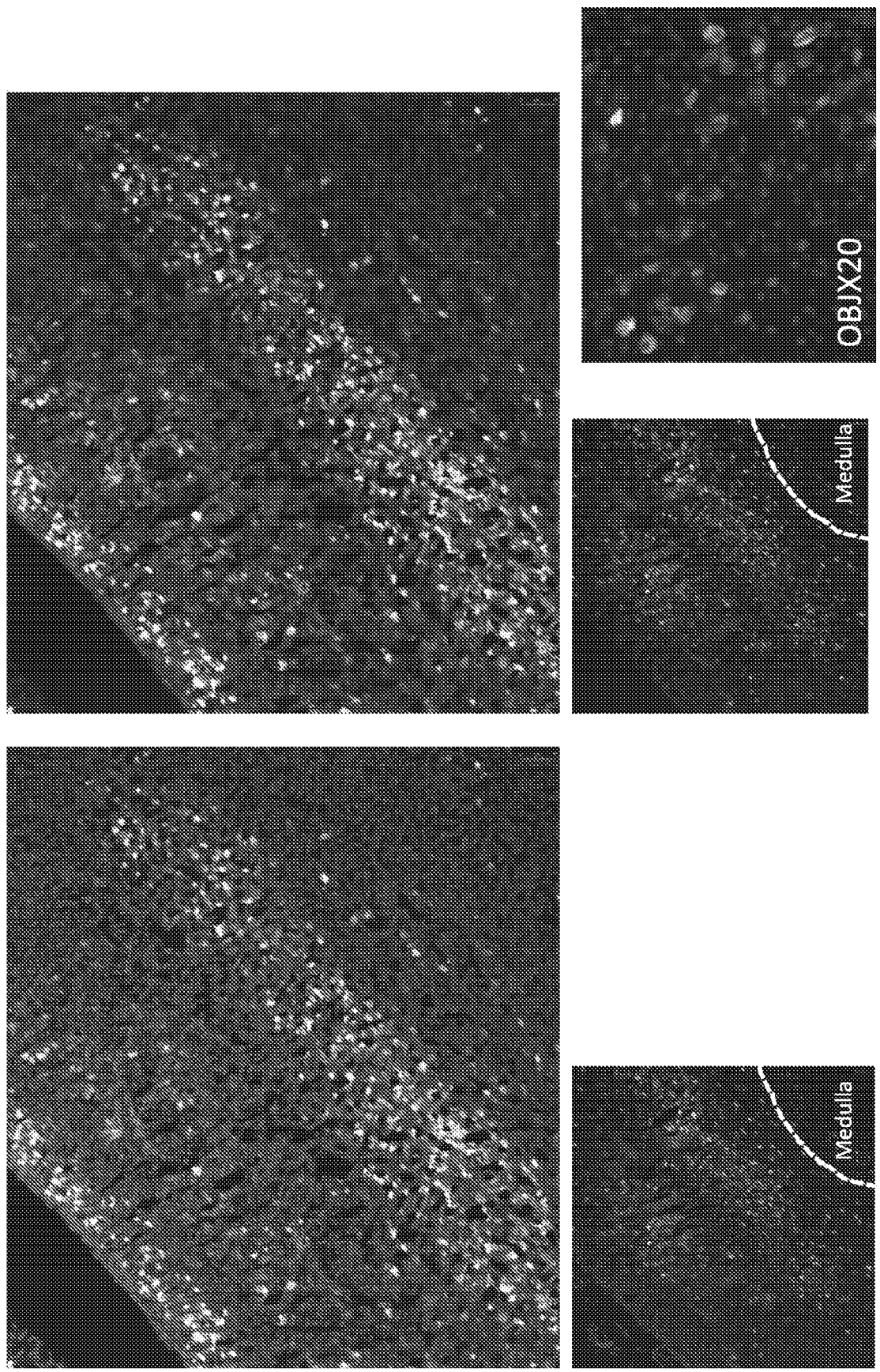
FIG. 60 shows GFP immunofluorescence images of AAV6-CAG-GFP in the left adrenal gland following intra-adrenal injection of vector. The dose applied to the gland was $6.0 \times 10^{11}$ vg. Low (top panel) and high (bottom panel) magnification showing the widespread distribution of GFP-positive cells. In the bottom right is a high-power magnification×20 (OBJX20) view of a small segment of the adrenal cortex showing the cytoplasmic localization of GFP in single cells. Nuclei are stained blue with DAPI.
Figure 61:
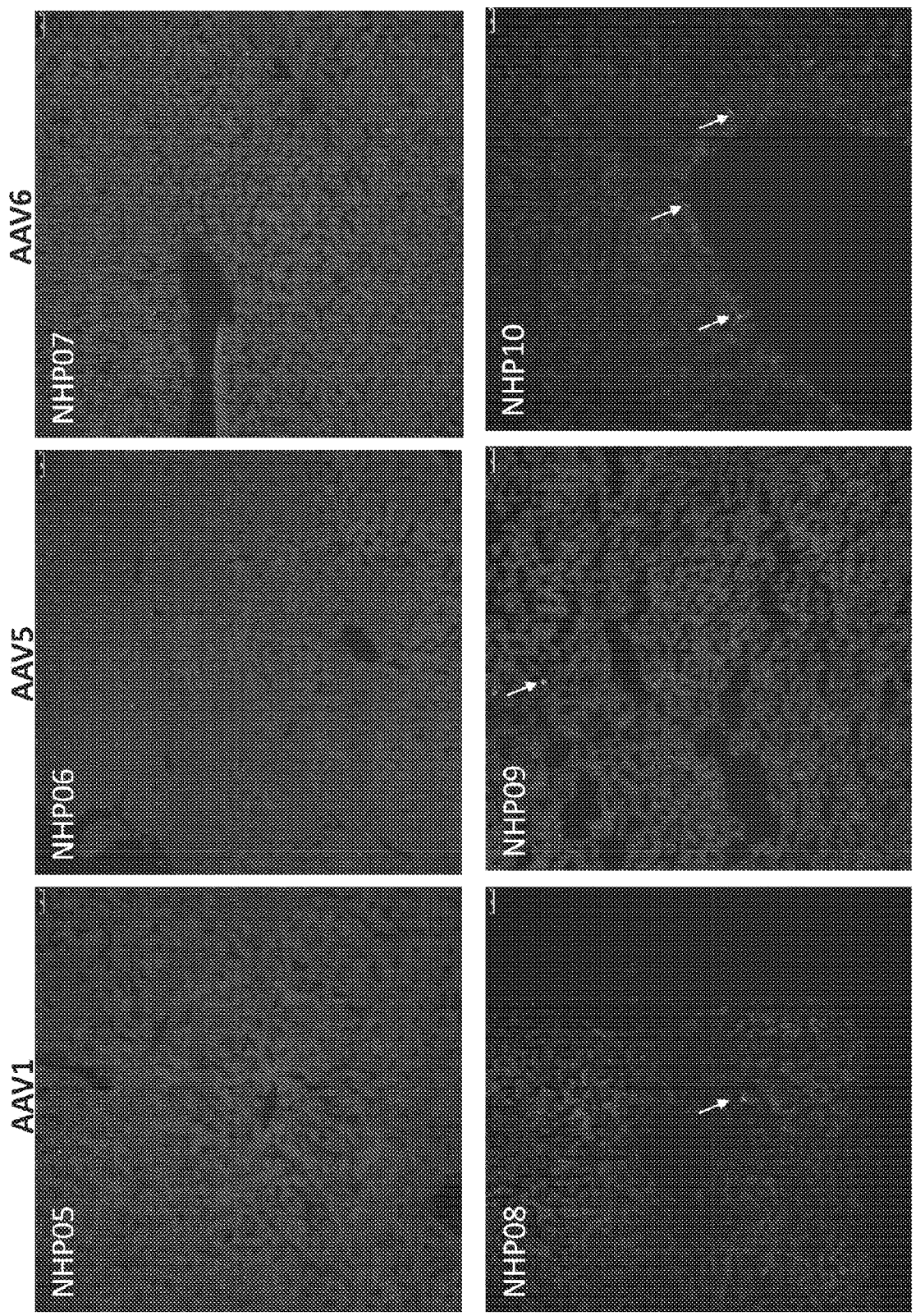
FIG. 61 shows CYP21HA immunofluorescence images of the livers of non-human primates (NHP) after intra-adrenal (IA) or intravenous (IV) administration of the indicated rAAV serotypes. White arrows indicate CYP21HA expressing cells (green).

FIGS. 52A-52C, 53A-53C, 54A-54C, 55A-55C, 56A-56C and 57A-57C show schematic view of CYP21HA vector genome copy (VGC) measurement spatial distribution in the adrenal glands and liver, scatter plots of the VGC and CYP21 mRNA measurement distributions and CYP21HA immunofluorescence images of selected NHPs treated as shown in Table 13. FIGS. 59-61 show immunofluorescence images of adrenals of NHPs treated with AAV1, AAV5 or AAV6 vectors. Cells expressing vector are in green and indicated by arrows.

The results of these studies suggest all three serotypes achieve adrenal expression, with the AAV5 serotype achieving superior adrenal expression in NHPs.

Example 13: Comparison of Efficacy of Wild-Type CYP21 Transgene and Codon-Optimized CYP21 Transgene Recombinant serotype AAV5 vectors were produced containing either a wild-type (WT) human CYP21 transgene or a codon-optimized (CO) human CYP21 transgene (SEQ ID NO:50). Each of these rAAV vectors included a CBA promoter, a Kozak sequence and the miR-122 miRNA binding site (Thakral and Ghoshal, Curr Gene Ther. 2015; 15(2): 142-150) for detargeting. The vector containing the wild-type transgene is referred to as AAV5-CBA-Kozak-hCYP21-miR122. The vector containing the codon-optimized transgene is referred to as AAV5-CBA-Kozak-COhCYP21-miR122. A control AAV5 vector was produced containing a wild-type cynomolgus CYP21 transgene (AAV5-CBA-Kozak-cynoCYP21).

Non-human primates (NHP) (*Macaca fascicularis*) were treated with vectors at the doses shown in FIG. 62. The vector preparations were administered to the NHPs intravenously (IV) for 10 minutes. The NHPs were euthanized 1.5 months after treatment.

CYP21 vector genome copy (VGC) measurements and mRNA measurements for each treatment group are shown in FIG. 63. mRNA levels were measured by quantitative reverse transcription PCR (qRT-PCR). The mRNA values show relative expression of two mRNAs, as indicated in FIG. 63. Cynomolgus-specific primers were used to measure the amount of cynomolgus CYP21 mRNA. For the VGC and mRNA rows in FIG. 63, the top number in each row is the mean, and the two bottom numbers are the range for the mean. FIG. 63 also shows a mean Sal-human to Sal-cynomolgus peptide ratio.

The results of this study suggest comparable expression of WT and CO human CYP21 transgenes in the adrenal glands of NHPs after intravenous delivery of AAV5-CBA-hCYP21 vectors.

TABLE 13

Effects of administration to non-human primates of rAAV vectors expressing human CYP21 or GFP.

| Serotype | Vector | NHP ID | Route | Gland injected | Injected dose (vg/kg) | Administration of dose to adrenal gland (no. of injections and volume) | Organ assessed for transduction levels | VGC (per cell) Mean | Range | RNA $10^{-2}$ (hCYP21/GAPDH) Mean | Range | IF |
|---|---|---|---|---|---|---|---|---|---|---|---|---|
| AAV1 | AAV1-CAG-hCYP21HA | NHP05 | Intra-adrenal | Left | 1.50E+11 | 3 × 50 μl | Left adrenal gland | 0.58 | 0.05-2.49 | 1.6 | 0-33.6 | NA |
| | | | | Right | 1.00E+11 | 2 × 50 μl | Right adrenal gland | 0.05 | 0.02-0.07 | 0.8 | 0-4.2 | − |
| | | | | | | | Liver | 0.15 | 0.09-0.21 | | | − |
| | | NHP08 | Intra-venous | N/A | 1.20E+12 | N/A | Left adrenal gland | 0.49 | 0.28-1 | 0.6 | 0.2-1.1 | NA |
| | | | | | | | Right adrenal gland | 0.99 | 0.40-2.38 | 0.6 | 0.3-1 | + |
| | | | | | | | Liver | 6.28 | 4.38-7.31 | | | + |
| | AAV1-PGK-hCYP21HA | NHP03 | Intra-adrenal | Right | 5.63E+11 | 1 × 80 μL + 1 × 70 μL | Right adrenal gland | 1.05 | 0.14-6.52 | | | + |
| | | | | | | | Left adrenal gland | 0.48 | 0.14-1.88 | | | 0 |
| | | | | | | | Liver | 1.9 | | | | 0 |
| | AAV1-CB6-eGFP | NHP03 | Intra-adrenal | Left | 3.00E+12 | 4 × 50 μL | Left adrenal gland | 0.56 | 0.14-2.6 | | | + |
| | | | | | | | Right adrenal gland | 0.09 | 0.03-0.15 | | | 0 |
| | | | | | | | Liver | 0.9 | | | | + |
| AAV5 | AAV5-CAG-hCYP21HA | NHP06 | Intra-adrenal | Left | 1.80E+11 | 3 × 50 μl | Left adrenal gland | 21.3 | 0.35-183.5 | 3.1 | 0-15.7 | NA |
| | | | | Right | 1.80E+11 | 3 × 50 μl | Right adrenal gland | 39.53 | 1.55-160.3 | 4.5 | 0.2-19.4 | + |
| | | | | | | | Liver | 1.35 | 1.01-1.78 | | | 0 |
| | | NHP09 | Intra-venous | N/A | 1.50E+12 | N/A | Left adrenal gland | 3.31 | 1.24-6.54 | 0.9 | 0.2-1.4 | NA |
| | | | | | | | Right adrenal gland | 1.4 | 1.05-2.02 | 1.2 | 0.7-1.6 | +++ |
| | | | | | | | Liver | 10.53 | 9.19-12.08 | | | + |
| | AAV5-PGK-hCYP21HA | NHP01 | Intra-adrenal | Right | 7.50E+11 | 3 × 50 μl | Right adrenal gland | 81.6 | 0.3-795 | | | +++ |
| | | | | | | | Left adrenal gland | 0.31 | 0.08-0.72 | | | NA |
| | | | | | | | Liver | 0.3 | | | | 0 |
| | | NHP02 | Intra-adrenal | Right | 1.13E+11 | 3 × 50 μl | Right adrenal gland | 1.9 | 0.08-5.64 | | | +++ |
| | | | | | | | Left adrenal gland | 0.043 | 0.02-0.07 | | | NA |
| | | | | | | | Liver | 0.1 | | | | 0 |
| | | NHP04 | Intra-adrenal | Right | 2.25E+12 | 4 × 50 ul | Right adrenal gland | 60 | 1.6-584 | | | NA |
| | | | | | | | Left adrenal gland | 2.26 | 0.47-11.39 | | | NA |
| | | | | | | | Liver | 2 | | | | 0 |
| | AAV5-PGK-GFP | NHP01 | Intra-adrenal | Left | 7.50E+11 | 3 × 50 μl | Left adrenalgland | 1.2 | 0.15-5.5 | | | +++ |
| | | | | | | | Right adrenal gland | 0.2 | 0.04-0.29 | | | ++ |
| | | | | | | | Liver | 0.4 | | | | ++ |
| AAV6 | AAV6-CAG-hCYP21HA | NHP07 | Intra-adrenal | Left | 1.60E+11 | 3 × 50 μl | Left adrenal gland | 0.29 | 0.01-1.93 | 1.8 | 0-8.2 | NA |
| | | | | Right | 1.60E+11 | 3 × 50 μl | Right adrenal gland | 2 | 1.1-2.4 | 34.8 | 4.8-80.1 | ++ |
| | | | | | | | Liver | 1.54 | 1.36-1.89 | | | 0 |
| | | NHP10 | Intra-venous | N/A | 1.30E+12 | N/A | Left adrenal gland | 0.07 | 0.03-0.11 | 0.1 | 0-0.2 | NA |
| | | | | | | | Right adrenal gland | 0.05 | 0.02-0.09 | 0.3 | 0-0.8 | 0 |
| | | | | | | | Liver | 9.61 | 7.73-11.63 | | | + |
| | AAV6-CAG-GFP | NHP02 | Intra-adrenal | Left | 1.50E+11 | 3 × 50 μl | Left adrenal gland | 0.065 | 0-0.22 | | | ++++ |
| | | | | | | | Right adrenal gland | 0.01 | 0-0.02 | | | +++ |
| | | | | | | | Liver | 0.8 | | | | +++ |
| | | NHP04 | Intra-adrenal | Left | 5.63E+11 | 1 × 50 μL + 1 × 60 μL + 1 × 70 μL | Left adrenal gland | 0.84 | 0.03-8.6 | | | NA |
| | | | | | | | Right adrenal gland | 0.06 | 0.01-0.42 | | | NA |
| | | | | | | | Liver | 0.1 | | | | +++ |

Acronyms:
Adeno-associated Virus (AAV),
Vector Genome (vg),
Vector Genome Copies (VGC),
Non-Human Primate (NHP),
Immunofluorescence (IF),
NA (not applicable)

What is claimed is:

1. A recombinant adeno-associated virus (rAAV) particle, comprising: an rAAV vector, wherein the rAAV vector comprises a nucleic acid molecule, comprising (i) at least one AAV inverted terminal repeat (ITR) and (ii) a non-AAV nucleotide sequence encoding a 21-hydroxylase (21 OH) protein comprising an amino acid sequence having at least 95% identity to SEQ ID NO: 1, wherein the non-AAV nucleotide sequence is operably linked to a CAG promoter, and wherein the rAAV particle is an AAV5 serotype.

2. The rAAV particle of claim 1, wherein the 21OH protein is human 21OH protein.

3. The rAAV particle of claim 1, wherein the non-AAV nucleotide sequence encoding a 21OH protein comprises or consists of the human 21OH (CYP21A2) cDNA.

4. The rAAV particle of claim 3, wherein the non-AAV nucleotide sequence encoding a 21OH protein comprises or consists of a codon-optimized nucleotide sequence.

5. The rAAV particle of claim 1, wherein the non-AAV nucleotide sequence encoding a 21OH protein;
   (i) comprises or consists of SEQ ID NO:50, or
   (ii) encodes the amino acid sequence of SEQ ID NO:1, or
   (iii) encodes an amino acid sequence at least 96%, at least 97%, at least 98%, or at least 99% identical to SEQ ID NO:1.

6. The rAAV particle of claim 1, wherein the promoter comprises or consists of the nucleotide sequence of SEQ ID NO: 2.

7. The rAAV particle of claim 1, wherein the ITR is an AAV1, AAV2, AAV3, AAV4, AAV5, AAV6, AAV7, AAV8, AAV9, AAV10, AAV11, AAV12, rh10, or rh74 serotype ITR.

8. A recombinant adeno-associated virus (rAAV) particle, comprising: an rAAV vector, wherein the rAAV vector comprises a nucleic acid molecule comprising a non-AAV nucleotide sequence encoding a 21-hydroxylase (21OH) protein comprising an amino acid sequence having at least 95% identity to SEQ ID NO: 1, wherein:
   (i) the non-AAV nucleotide sequence is operably linked to a CAG promoter;
   (ii) the rAAV vector comprises at least one AAV inverted terminal repeat (ITR), wherein the ITR is from an AAV of serotype AAV1, AAV2, AAV3, AAV4, AAV5, AAV6, AAV7, AAV8, AAV9, AAV10, AAV11, AAV12, rh10, or rh74; and
   (iii) the rAAV particle is an AAV5 serotype.

9. A pharmaceutical composition comprising the rAAV particle of claim 1, and a pharmaceutically acceptable carrier, diluent or excipient.

10. A method of producing an rAAV particle, the method comprising culturing a host cell containing: (a) the rAAV vector comprising a nucleic acid molecule, comprising (i) at least one AAV inverted terminal repeat (ITR) and (ii) a non-AAV nucleotide sequence encoding a 21-hydroxylase (21OH) protein comprising an amino acid sequence having at least 95% identity to SEQ ID NO: 1, wherein the non-AAV nucleotide sequence is operably linked to a CAG promoter; (b) a nucleic acid molecule encoding an AAV rep protein; (c) a nucleic acid molecule encoding at least one AAV capsid protein and (d) sufficient helper functions for packaging the rAAV particle, wherein the rAAV particle is an AAV5 serotype.

11. A method of expressing 21-hydroxylase (21OH) in a subject in need thereof, comprising providing a therapeutically effective amount of the rAAV particle of claim 1 to the subject, thereby expressing 21OH in the subject.

12. The method of claim 11, wherein the 21OH is expressed in the subject's adrenal cortex, adrenal medulla, adrenal stem cells, adrenal progenitor cells, liver, or ovary.

13. A method of treating a subject with 21-hydroxylase deficiency (21OHD), comprising providing a therapeutically effective amount of the rAAV particle of claim 1 to the subject, thereby treating 21OHD in the subject.

14. The method of claim 13, wherein the rAAV particle or a composition comprising the rAAV particle, is administered to the subject intravenously, by direct injection into the adrenal gland via open surgery or laparoscopy, or by injection into an adrenal artery via catheterization.

15. The method of claim 13, wherein the subject is affected with congenital adrenal hyperplasia and/or the Prader stage IV or V form of 21OHD.

16. The rAAV particle of claim 1, wherein the rAAV vector further comprises a Kozak sequence.

17. The rAAV particle of claim 1, wherein the rAAV vector further comprises an miR-122 binding site.

18. The method of claim 11, wherein the rAAV article, or a composition comprising the rAAV particle, is administered to the subject intravenously, by direct injection into the adrenal gland via open surgery or laparoscopy or by injection into an adrenal artery via catheterization.

19. A recombinant adeno-associated virus (rAAV) particle, comprising: an rAAV vector, wherein the rAAV vector comprises a nucleic acid molecule, comprising a non-AAV nucleotide sequence encoding a human 21-hydroxylase (21OH) protein comprising an amino acid sequence having at least 95% identity to SEQ ID NO: 1 and an miR-122 binding site, wherein the non-AAV nucleotide sequence encoding a human 21-hydroxylase (21OH) protein is operably linked to a CAG promoter, and wherein the rAAV particle is an AAV5 serotype.

20. The rAAV vector of claim 19, wherein the non-AAV nucleotide sequence encoding a 21OH protein comprises or consists of a codon-optimized nucleotide sequence.

* * * * *